United States Patent
Bhavar et al.

(10) Patent No.: US 9,783,533 B2
(45) Date of Patent: Oct. 10, 2017

(54) GLUTAMINASE INHIBITORS

(71) Applicant: Rhizen Pharmaceuticals SA, La Chaux-de-Fonds (CH)

(72) Inventors: Prashant K. Bhavar, Hyderabad (IN); Swaroop K. Vakkalanka, La Chaux-de-Fonds (CH); Srikant Viswanadha, Hyderabad (IN); Merikapudi Gayatri Swaroop, Hyderabad (IN); Govindarajulu Babu, Hyderabad (IN)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 14/769,331

(22) PCT Filed: Jan. 5, 2015

(86) PCT No.: PCT/IB2015/050075
§ 371 (c)(1),
(2) Date: Aug. 20, 2015

(87) PCT Pub. No.: WO2015/101957
PCT Pub. Date: Jul. 9, 2015

(65) Prior Publication Data
US 2016/0318921 A1 Nov. 3, 2016

(30) Foreign Application Priority Data

| Jan. 6, 2014 | (IN) | ................ 36/CHE/2014 |
| Jan. 6, 2014 | (IN) | ................ 39/CHE/2014 |
| May 29, 2014 | (IN) | ............ 2639/CHE/2014 |
| May 29, 2014 | (IN) | ............ 2647/CHE/2014 |
| Jun. 6, 2014 | (IN) | ............ 2783/CHE/2014 |
| Jul. 18, 2014 | (IN) | ............ 3525/CHE/2014 |
| Jul. 24, 2014 | (IN) | ............ 3612/CHE/2014 |
| Jul. 24, 2014 | (IN) | ............ 3613/CHE/2014 |
| Oct. 31, 2014 | (IN) | ............ 5438/CHE/2014 |

(51) Int. Cl.

| *C07D 417/14* | (2006.01) |
| *A61K 31/433* | (2006.01) |
| *C07D 417/06* | (2006.01) |
| *C07D 285/135* | (2006.01) |
| *A61K 31/44* | (2006.01) |
| *A61K 31/4439* | (2006.01) |
| *A61K 31/444* | (2006.01) |
| *A61K 31/4965* | (2006.01) |
| *A61K 31/497* | (2006.01) |
| *A61K 31/501* | (2006.01) |
| *A61K 31/505* | (2006.01) |
| *A61K 31/506* | (2006.01) |
| *A61K 45/06* | (2006.01) |
| *C07D 213/75* | (2006.01) |
| *C07D 239/42* | (2006.01) |
| *C07D 241/20* | (2006.01) |
| *C07D 401/12* | (2006.01) |
| *C07D 417/08* | (2006.01) |
| *A61K 31/4545* | (2006.01) |
| *C07D 401/04* | (2006.01) |

(52) U.S. Cl.
CPC .......... *C07D 417/14* (2013.01); *A61K 31/433* (2013.01); *A61K 31/44* (2013.01); *A61K 31/444* (2013.01); *A61K 31/4439* (2013.01); *A61K 31/4545* (2013.01); *A61K 31/497* (2013.01); *A61K 31/4965* (2013.01); *A61K 31/501* (2013.01); *A61K 31/505* (2013.01); *A61K 31/506* (2013.01); *A61K 45/06* (2013.01); *C07D 213/75* (2013.01); *C07D 239/42* (2013.01); *C07D 241/20* (2013.01); *C07D 285/135* (2013.01); *C07D 401/04* (2013.01); *C07D 401/12* (2013.01); *C07D 417/06* (2013.01); *C07D 417/08* (2013.01)

(58) Field of Classification Search
CPC ........................... C07D 417/14; A61K 31/433
See application file for complete search history.

(56) References Cited

U.S. PATENT DOCUMENTS

| 5,552,427 A | 9/1996 | Matsutani et al. |
| 6,451,828 B1 | 9/2002 | Newcomb et al. |
| 8,465,736 B2 | 6/2013 | Bausch et al. |
| 8,604,016 B2 | 12/2013 | Li et al. |
| 8,865,718 B2 | 10/2014 | Li et al. |
| 2002/0115698 A1 | 8/2002 | Newcomb et al. |
| 2006/0276438 A1 | 12/2006 | Sethuraman et al. |
| 2012/0245344 A1 | 9/2012 | Endo et al. |
| 2013/0157998 A1 | 6/2013 | Li et al. |

(Continued)

FOREIGN PATENT DOCUMENTS

| EP | 656210 A1 | 6/1995 |
| WO | WO-9909825 A1 | 3/1999 |

(Continued)

OTHER PUBLICATIONS

Shukla et al. (J. Med. Chem. 2012, 55, 10551-10563).*

(Continued)

*Primary Examiner* — Robert Havlin
(74) *Attorney, Agent, or Firm* — Blank Rome LLP

(57) ABSTRACT

The present disclosure provides compounds of formula (I) to (III) as glutaminase inhibitors, methods of preparing them, pharmaceutical compositions containing them and methods of treatment, prevention and/or amelioration of diseases or disorders involving glutamine.

13 Claims, No Drawings

(56) References Cited

U.S. PATENT DOCUMENTS

| | | |
|---|---|---|
| 2014/0050699 A1 | 2/2014 | Li et al. |
| 2014/0142081 A1 | 5/2014 | Lemieux et al. |
| 2014/0142146 A1 | 5/2014 | Lemieux et al. |
| 2014/0194421 A1 | 7/2014 | Li et al. |
| 2014/0369961 A1 | 12/2014 | Li et al. |
| 2015/0004134 A1 | 1/2015 | Bennett et al. |

FOREIGN PATENT DOCUMENTS

| | | |
|---|---|---|
| WO | WO-0059533 A1 | 10/2000 |
| WO | WO-0302261 A1 | 1/2003 |
| WO | WO-2004108153 A1 | 12/2004 |
| WO | WO-2007128588 A2 | 11/2007 |
| WO | WO-2008083238 A2 | 7/2008 |
| WO | WO-2010033871 A2 | 3/2010 |
| WO | WO-2010111504 A2 | 9/2010 |
| WO | WO-2011076967 A1 | 6/2011 |
| WO | WO-2011143160 A2 | 11/2011 |
| WO | WO-2012006506 A1 | 1/2012 |
| WO | WO-2012034123 A1 | 3/2012 |
| WO | WO-2013044596 A1 | 4/2013 |
| WO | WO-2013078123 A1 | 5/2013 |
| WO | WO-2014043633 A1 | 3/2014 |
| WO | WO-2014078645 A1 | 5/2014 |
| WO | WO-2014079011 A1 | 5/2014 |
| WO | WO-2014079136 A1 | 5/2014 |
| WO | WO-2014079150 A1 | 5/2014 |
| WO | WO-2014081925 A1 | 5/2014 |
| WO | WO-2014089048 A1 | 6/2014 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*

Wermuth, The Practice of Medicinal Chemsitry, 2d ed. (2003), 768 pages. Chs. 9-10 provided.*

International Search Report issued in PCT/IB2015/050075 on Jul. 13, 2015.

* cited by examiner

GLUTAMINASE INHIBITORS

This application is the national stage of International Patent Application No. PCT/IB2015/050075, filed Jan. 5, 2015, which claims the benefit of Indian Patent Application Nos. 36/CHE/2014, filed Jan. 6, 2014, 39/CHE/2014, filed Jan. 6, 2014, 2639/CHE/2014, filed May 29, 2014, 2647/CHE/2014, filed May 29, 2014, 2783/CHE/2014, filed Jun. 6 2014, 3525/CHE/2014 filed Jul. 18, 2014, 3612/CHE/2014, filed Jul. 24, 2014, 3613/CHE/2014, filed Jul. 24, 2014, and 5438/CHE/2014, filed Oct. 31, 2014, each of which is hereby incorporated by reference in its entirety.

FIELD OF THE INVENTION

The present invention provides compounds of formula (I) to (III) as glutaminase inhibitors, methods of preparing them, pharmaceutical compositions containing them and methods of treatment, prevention and/or amelioration of diseases or disorders involving glutamine.

BACKGROUND OF THE INVENTION

Glutaminase (glutaminase I,L-glutaminase, glutamine aminohydrolase) is an amido-hydrolase enzyme that generates glutamate from glutamine. Glutaminase has been reported to have tissue-specific isoenzymes. Glutaminase has an important role in glial cells. Glutamine is the most abundant free amino acid in the human body; it is essential for the growth of normal and neoplastic cells and for the culture of many cell types. Glutamine is an important source of energy for neoplastic tissues, and products of its metabolism include, among others, glutamate (Glu) and glutathione (GSH), the two molecules that play a key role in tumor proliferation, invasiveness and resistance to therapy. Glutamine hydrolysis in normal and transforming mammalian tissues alike is carried out by different isoforms of glutaminases, of which the two major types are liver-type glutaminase (LGA) and kidney-type glutaminase (KGA) (see *Neurochem Int.*, 2009 July-August; 55(1-3):71-5. doi: 10.1016/j.neuint.2009.01.008. Epub 2009 February).

Cancer cells require a robust supply of reduced nitrogen to produce nucleotides, non-essential amino acids and a high cellular redox activity. Glutamine provides a major substrate for respiration as well as nitrogen for the production of proteins, hexosamines, and macromolecules. Therefore, glutamine is one of key molecules in cancer metabolism during cell proliferation. The notion of targeting glutamine metabolism in cancer, originally rationalized by the number of pathways fed by this nutrient, has been reinforced by more recent studies demonstrating that its metabolism is regulated by oncogenes. Glutaminase (GA) is the first enzyme that converts glutamine to glutamate, which is in turn converted to alpha-ketoglutarate for further metabolism in the tricarboxylic acid cycle. Different GA isoforms in mammals are encoded by two genes, Gls and Gls2. As each enzymatic form of GA has distinct kinetic and molecular characteristics, it has been speculated that the differential regulation of GA isoforms may reflect distinct functions or requirements in different tissues or cell states. GA encoded by the Gls gene (GLS) has been demonstrated to be regulated by oncogenes and to support tumor cell growth. GA encoded by the Gls2 gene (GLS2) reduces cellular sensitivity to reactive oxygen species associated apoptosis possibly through glutathione-dependent antioxidant defense, and therefore to behave more like a tumor suppressor. Thus, modulation of GA function may be a new therapeutic target for cancer treatment (see Matés et al., *Curr. Mol. Med.*, 2013 May; 13(4), 514-534).

One hallmark of cancer cells is their adaptation to rely upon an altered metabolic scheme that includes changes in the glycolytic pathway, known as the Warburg effect, and elevated glutamine metabolism. Glutaminase, a mitochondrial enzyme, plays a key role in the metabolism of glutamine in cancer cells, and its inhibition could significantly impact malignant transformation (see Katt et al., *Mol. Cancer Ther.*, 11(6); 1269-78, 2012). Feeding off the breakdown of glutamine, cancer cells are able to grow and divide into a tumour. Glutaminase therefore makes a promising therapeutic target for the prevention of tumour progression. Inhibition of this enzyme could effectively starve the cancer cells of their energy source. See Medina et al., *J. Nutr.*, Sep. 1, 2001, Vol. 131, No. 9 2539S-2542S.

Glutaminase plays a crucial role in the mechanisms of cancer, such as cell survival, proliferation and growth. There are two reported glutaminase inhibitors namely 6-diazo-5-oxo-L-norleucine (DON) which was isolated originally from *Streptomyces* in a sample of Peruvian soil and was characterized in 1956 by Henry W Dion (see Dion et al., *Antibiotics and Chemotherapy*, 1954, 78, 3075-3077) and suggested as a cancer therapy and bis-2-(5-phenylacetamido-1,3,4-thiadiazol-2-yl)ethyl sulfide (BPTES) disclosed by Elan Pharmaceuticals. There is an ongoing research effort reported by other groups working at Cornell University and Calithera Biosciencesis to discover and identify small molecule inhibitors of glutaminase. DON has also been reported to be evaluated in combination with PEG-PGA by New Medical Enzymes AG. In addition to BPTES and DON, other reported glutaminase inhibitors are as summarised in the table below.

| Agent | Company | Clinical status |
|---|---|---|
| BPTES | — | Discovery |
| CB-839 | Calithera Biosciences | Phase-I |
| Compound 968 | Cornell University | Preclinical |
| GlutaDON (PEG-PGA + DON) | New Medical Enzymes AG | Phase-2 |
| GlutaChemo (PEG-PGA + an ideal candidate) | New Medical Enzymes AG | Preclinical |

Reviews and studies regarding Glutamine and Glutaminase in cancer and other diseases have been given by Medina et al., *J. Nutr.*, Sep. 1, 2001, Vol. 131, No. 9, 2539S-2542S; Ajit G. Thmas et al., *Biochemical and Biophysical Research Communications*, 443, 2014, 32-36; Monica Szeliga et al., *Neurochemistrt Intermationa*, 55, 2009, 71-77; and Curthoys et al., *Annu. Rev. Nutr.*, 1995, 15, 133-159. All of these literature disclosures are incorporated herein by reference in their entirety for all purposes.

Patent literature related to glutaminase inhibitors includes International Publication Nos. WO 99/09825, WO 00/59533, WO 03/022261, WO 04/108153, WO 07/128588, WO 10/033871, WO 10/111504, WO 11/076967, WO 11/143160, WO 12/006506, WO 12/034123, WO 13/044596, WO 13/078123, WO 14/078645, WO 14/089048, WO14/043633, WO14/079011, WO14/079136, WO14/079150, and WO14/081925, U.S. Publication Nos. 2002/0115698, 2006/0276438, 2013/0157998, 2014/0050699, 2014/0194421, 2014/0369961, 2015/0004134, 20140142081, and 20140142146, U.S. Pat. Nos. 5,552,427, 6,451,828, 8,465,736, 8,604,016, and 8,865,718 and European Publication No. 656210, each of which is incorporated herein by reference in its entirety for all purposes.

There still remains an unmet need for novel glutaminase inhibitors for the treatment of diseases and disorders associated with cell proliferation such as cancer and other immunological and neurological disorders.

SUMMARY OF THE INVENTION

The present invention relates to compounds of formula (I) to (III), methods for their preparation, pharmaceutical compositions containing them, and methods of treatment using them. In particular, the compounds of formula (I) to (III) and their pharmaceutically acceptable salts are useful in the treatment, prevention and/or amelioration of diseases or disorders involving glutamine.

In one aspect, the present invention relates to a compound of formula (I):

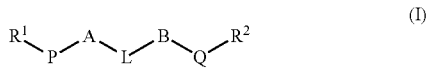

or a tautomer thereof, prodrug thereof, N-oxide thereof, stereoisomer thereof, pharmaceutically acceptable ester thereof or pharmaceutically acceptable salt thereof, wherein L is $-L_1-L_2-L_3-$; wherein $L_1$ is absent or independently selected from substituted or unsubstituted $C_{1-6}$ alkyl, substituted or unsubstituted $C_{2-6}$ alkenyl, substituted or unsubstituted $C_{2-6}$ alkynyl, O, S, $-S(=O)_q-$, $-C(=O)-$ and $-NR^x-$;

$L_2$ is substituted or unsubstituted 3 to 14 membered heterocyclyl;

$L_3$ is absent or independently selected from substituted or unsubstituted $C_{1-6}$ alkyl, substituted or unsubstituted $C_{2-6}$ alkenyl, substituted or unsubstituted $C_{2-6}$ alkynyl, O, S, $-S(=O)_q-$, $-C(=O)-$ and $-NR^x-$;

A and B are independently selected from

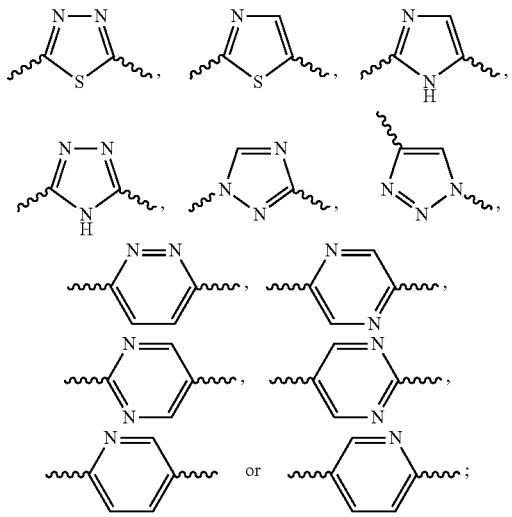

each of A and B are optionally substituted with one or more $R^3$;

each occurrence of $R^3$ is, independently, hydrogen, halogen, substituted or unsubstituted $C_{1-3}$ alkyl, nitro, amino, substituted or unsubstituted $C_{1-6}$ alkoxy, or substituted or unsubstituted $C_{1-6}$ alkylamino;

P and Q are independently selected from substituted or unsubstituted alkyl, substituted or unsubstituted alkenyl, substituted or unsubstituted alkynyl, substituted or unsubstituted alkoxy, $-NR^x-C(=O)-(CR^xR^y)_r-$, $-NH-C(=O)-C(R^xR^y)-$, $-(CR^xR^y)_r-C(=O)-NR^x-$, $-(CR^xR^y)-C(=O)-NH-$, $-C(=O)NR^x-(CR^xR^y)_r-$, $-C(=O)NH-C(R^xR^y)-$, $-(CR^xR^y)_r-NR^x-C(=O)-$, $-(CR^xR^y)-NH-C(=O)-$, $-NR^x-$, $-NR^xC(=O)-$, $-NR^xC(=S)-$, $-NR^xS(=O)_q-$, $-C(=O)NR^x-$, $-C(=S)NR^x-$, $-S(=O)_qNR^x-$, $NR^xC(=O)NR^x-$, $-NR^xC(=S)NR^x-$, $-C(=O)-$, $-C(=S)-$, $-C(=O)ONR^x-$, $=N-N(R^x)-$, $-N(R^x)-N=$ or $-NR^xC(=O)O-$;

$R^1$ and $R^2$ are independently selected from hydrogen, hydroxy, halogen, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, $-C(=O)OR^z$, $-C(=O)R^z$, $-C(=S)R^z$, $-C(=O)NR^zR^z$, $-C(=O)ONR^zR^z$, $-NR^zR^z$, $-NR^zC(=O)NR^zR^z$, $-NR^zS(=O)R^z$, $-NR^zS(=O)_2R^z$, $=N-N-R^zR^z$, $-NR^zC(=O)OR^z$, $-NR^zC(=O)R^z$, $-NR^xC(=S)R^y-$ $NR^zC(=S)NR^zR^z$, $-SONR^zR^z$, $-SO_2NR^zR^z$, $-OR^z$, $-OR^zC(=O)NR^zR^z$, $-OR^zC(=O)OR^z$, $-OC(=O)R^z$, $-OC(=O)NR^zR^z$, $-R^zNR^zC(=O)R^z$, $-R^zOR^z$, $-R^zC(=O)OR^z$, $-R^zC(=O)NR^zR^z$, $R^zC(=O)R^z$, $-R^zOC(=O)R^z$, $-SR^z$, $-SOR^z$, $-SO_2R^z$, $-CR^xR^yC(=O)R^z$ or $-CR^xR^yC(=S)R^z$;

each occurrence of $R^x$, $R^y$ and $R^z$ is independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of $R^x$ and $R^y$ when bound to a common atom may be joined to form (i) a substituted or unsubstituted saturated or unsaturated 3-14 membered ring, which may optionally include one or more heteroatoms which may be the same or different and are selected from O, $NR^z$ and S, or (ii) an oxo (=O), thio (=S) or imino (=$NR^z$) group;

each occurrence of q is independently 0, 1 or 2; and each occurrence of r is independently 0, 1 or 2.

For avoidance of doubt and unless indicated otherwise, formulas are to be read in the direction they are shown. For example, (a) if P is $-CH_2-C(=O)-NH-$ in formula (I) (i.e., $R^1-P-A-L-B-Q-R^2$) than the compound would have the formula $R^1-CH_2-C(O)-NH-A-L-B-Q-R^2$ or (b) if P is $-CH_2-C(=O)-NH-$ and Q is $-NH-C(=O)-CH_2-$ in formula (I) (i.e., $R^1-P-A-L-B-Q-R^2$) than the compound would have the formula $R^1-CH_2-C(O)-NH-A-L-B-NH-C(=O)-CH_2-R^2$.

Further preferred is a compound having the formula (I), wherein A and B are independently selected from

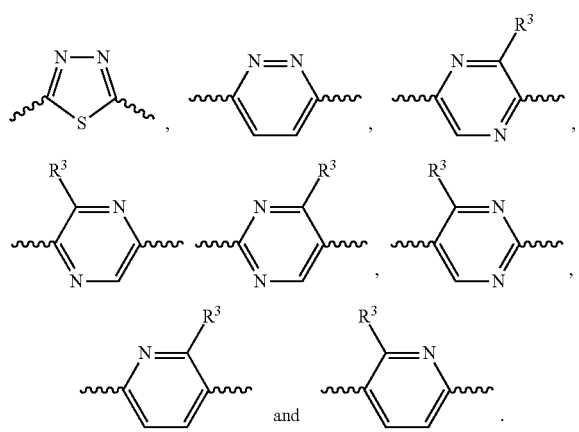

wherein R³ is hydrogen, halogen or substituted or unsubstituted C$_{1-3}$ alkyl (e.g., methyl).

Further preferred is a compound having the formula (I), wherein A and B are independently selected from

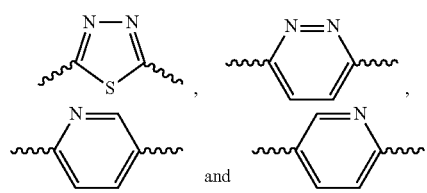

Further preferred is a compound having the formula (I), wherein A and B are independently selected from

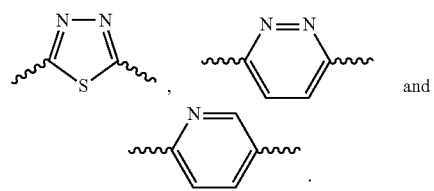

Further preferred is a compound having the formula (I), wherein A and B are independently selected from

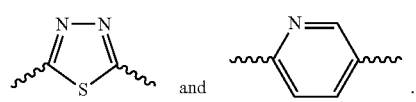

Further preferred is a compound having the formula (I), wherein A and B are independently selected from

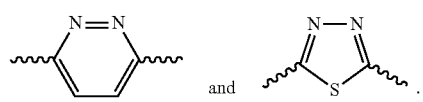

Further preferred is a compound having the formula (I), wherein

A is

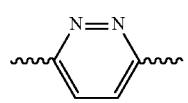

and B is

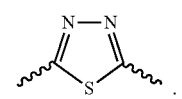

Further preferred is a compound having the formula (I), wherein

A is

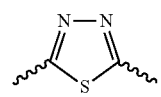

and B is

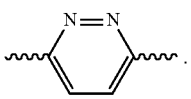

Further preferred is a compound having the formula (I), wherein each of P and Q are independently selected from —NR$^x$C(=O)—(CR$^x$R$^y$)$_r$—, —(CR$^x$R$^y$)$_r$—C(=O)—NR$^x$—, —C(=O)NR$^x$—(CR$^x$R$^y$)$_r$—, —(CR$^x$R$^y$)$_r$—NR$^x$—C(=O)—, —NH—C(=O)—C(R$^x$R$^y$)—, —(CR$^x$R$^y$)—C(=O)—NH—, —NR$^x$C(=O)—, —NR$^x$C(=S)—, —NR$^x$S(=O)$_q$—, —C(=O)NR$^z$—, —C(=S)NR$^z$—, or —NR$^x$—.

Further preferred is a compound having the formula (I), wherein each of P and Q are independently selected from —NR$^x$C(=O)—(CR$^x$R$^y$)—, —(CR$^x$R$^y$)—C(=O)—NR$^x$—, —NR$^x$C(=O)— or —NR$^x$—, wherein R$^x$ and R$^y$ are independently selected from hydrogen, substituted or unsubstituted C$_{1-3}$ alkyl, halogen, hydroxy and substituted or unsubstituted C$_{1-3}$ alkoxy.

Further preferred is a compound having the formula (I), wherein each of P and Q are independently —NH—C(=O)—(CR$^x$R$^y$)—, —(CR$^x$R$^y$)—C(=O)—NH—, —NH—C(=O)— or —NH—, wherein R$^x$ and R$^y$ are hydrogen.

Further preferred is a compound having the formula (I), wherein each of P and Q are independently —NH—C(=O)—(CH$_2$)—, —(CH$_2$)—C(=O)—NH—, —NH—C(=O)— or —NH—.

Further preferred is a compound having the formula (I), wherein P is —(CH$_2$)—C(=O)—NH— and Q is —NH—C(=O)—CH$_2$—, —NH—C(=O)— or —NH—.

Further preferred is a compound having the formula (I), wherein P is —(CH$_2$)—C(=O)—NH—, —NH—C(=O)— or —NH— and Q is —NH—C(=O)—CH$_2$—.

Further preferred is a compound having the formula (I), wherein P is —(CH$_2$)—C(=O)—NH— and Q is —NH—C(=O)—CH$_2$—.

Yet another embodiment is a compound having the formula (II) or (III):

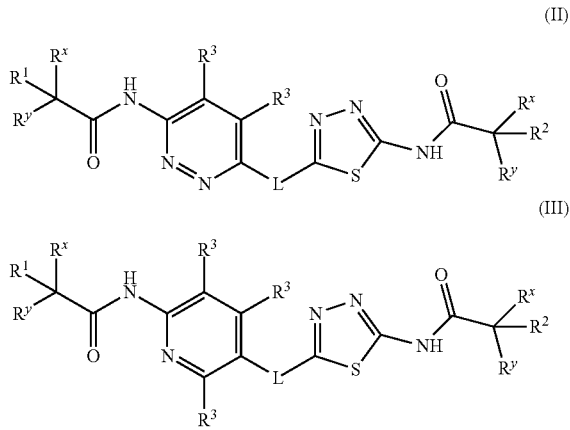

or a tautomer thereof, prodrug thereof, N-oxide thereof, stereoisomer thereof, pharmaceutically acceptable ester thereof or pharmaceutically acceptable salt thereof, wherein each of the variables L, $R^1$, $R^2$, $R^3$, $R^x$ and $R^y$ are as defined above in relation to formula (I).

Further preferred is a compound having the formula (I), (II) or (III), wherein
- $L_1$ is absent, substituted or unsubstituted $C_{1-6}$ alkyl or —$NR^x$—, wherein $R^x$ is hydrogen or $C_{1-3}$ alkyl;
- $L_2$ is substituted or unsubstituted 3 to 10 membered heterocyclyl; and
- $L_3$ is absent, substituted or unsubstituted $C_{1-6}$ alkyl or —$NR^x$—, wherein $R^x$ is hydrogen or $C_{1-3}$ alkyl.

Further preferred is a compound having the formula (I), (II) or (III), wherein
- $L_1$ is absent or substituted or unsubstituted $C_{1-6}$ alkyl;
- $L_2$ is substituted or unsubstituted 3 to 10 membered heterocyclyl; and
- $L_3$ is absent or substituted or unsubstituted $C_{1-6}$ alkyl.

Further preferred is a compound having the formula (I), (II) or (III), wherein
- $L_1$ is substituted or unsubstituted $C_{1-6}$ alkyl;
- $L_2$ is substituted or unsubstituted 3 to 10 membered heterocyclyl; and
- $L_3$ is substituted or unsubstituted $C_{1-6}$ alkyl.

Further preferred is a compound having the formula (I), (II) or (III), wherein
- $L_1$ is substituted or unsubstituted $C_{1-6}$ alkyl;
- $L_2$ is substituted or unsubstituted 3 to 10 membered heterocyclyl;
- $L_3$ is absent.

Further preferred is a compound having the formula (I), (II) or (III), wherein
- $L_1$ is absent.
- $L_2$ is substituted or unsubstituted 3 to 10 membered heterocyclyl; and
- $L_3$ is substituted or unsubstituted $C_{1-6}$ alkyl.

Further preferred is a compound having the formula (I), (II) or (III), wherein
- $L_1$ is absent.
- $L_2$ is substituted or unsubstituted 3 to 10 membered heterocyclyl;
- $L_3$ is absent.

Further preferred is a compound having the formula (I), (II) or (III), wherein $L_2$ is selected from

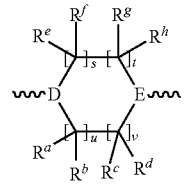

wherein
D and E are independently selected from CR" or N, wherein each occurrence of R" is independently hydrogen, hydroxyl, halogen or substituted or unsubstituted $C_{1-3}$ alkyl;

each occurrence of $R^a$, $R^b$, $R^c$, $R^d$, $R^e$, $R^f$, $R^g$ and $R^h$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl; or any two of $R^a$, $R^b$, $R^c$, $R^d$, $R^e$, $R^f$, $R^g$ and $R^h$ (such as two groups bound to a common atom or adjacent atoms or any two groups which when joined form a chemically stable structure) may be joined to form (i) a substituted or unsubstituted, saturated or unsaturated 3-14 membered ring, which may optionally include one or more heteroatoms which may be the same or different and are selected from O, NR' (where R' is H or $C_{1-3}$ alkyl) and S, or (ii) an oxo (=O), thio (=S) or imino (=NR') group; and each of s, t, u and v is 0, 1 or 2 with the proviso that the sum of s, t, u and v is not 0 (i.e., s+t+u+v≥1).

Further preferred is a compound having the formula (I), (II) or (III), wherein each occurrence of $R^a$, $R^b$, $R^c$, $R^d$, $R^e$, $R^f$, $R^g$ and $R^h$ is independently selected from hydrogen, hydroxy, and substituted or unsubstituted $C_{1-3}$ alkyl, or any two of $R^a$, $R^b$, $R^c$, $R^d$, $R^e$, $R^f$, $R^g$ and $R^h$ when bound to a common atom may form oxo (=O) or any two of $R^a$, $R^b$, $R^c$, $R^d$, $R^e$, $R^f$, $R^g$ and $R^h$ form a substituted or unsubstituted cycloalkyl group.

Further preferred is a compound having the formula (I), (II) or (III), wherein each of $R^a$, $R^b$, $R^c$, $R^d$, $R^e$, $R^f$, $R^g$ and $R^h$ is hydrogen and the sum of s, t, u and v is 1-4, such as 1, 2, 3 or 4.

Further preferred is a compound having the formula (I), (II) or (III), wherein $R^a$, $R^b$, $R^c$, $R^d$, $R^e$, $R^f$, $R^g$ and $R^h$ is hydrogen, s is 0, t is 1 and the sum of u and v is 3.

Further preferred is a compound having the formula (I), (II) or (III), wherein
(i) $R^a$, $R^b$, $R^c$, $R^d$, $R^e$, $R^f$, $R^g$ and $R^h$ is hydrogen, and each of s, t, u and v is 1;
(ii) $R^a$, $R^b$, $R^c$, $R^d$, $R^e$, $R^f$, $R^g$ and $R^h$ is hydrogen, s is 0, and each of t, u and v is 1;
(iii) $R^a$, $R^b$, $R^c$, $R^d$, $R^e$, $R^f$, $R^g$ and $R^h$ is hydrogen, s is 0, each of t and v is 1 and u is 2; or
(iv) $R^a$, $R^b$, $R^c$, $R^d$, $R^e$, $R^f$, $R^g$ and $R^h$ is hydrogen, s is 0, t is 1 and the sum of u and v is 1, 2 or 3.

Further preferred is a compound having the formula (I), (II) or (III), wherein
(i) each of $R^a$, $R^b$, $R^c$, $R^d$, $R^e$, $R^f$, $R^g$ and $R^h$ is hydrogen, s is 0, t is 1 and u+v=3;
(ii) each of $R^a$, $R^b$, $R^c$, $R^d$, $R^e$, $R^f$, $R^g$ and $R^h$ is hydrogen and s, t, u and v are each 1;
(iii) each of $R^a$, $R^b$, $R^c$, $R^d$, $R^e$, $R^f$, $R^g$ and $R^h$ is hydrogen, s is 0 and t, u and v are each 1;
(iv) each of $R^a$, $R^b$, $R^c$, $R^d$, $R^e$, $R^f$, $R^g$ and $R^h$ is hydrogen and the sum of s, t, u and v is 2; or (v) each of $R^a$, $R^b$, $R^c$, $R^d$, $R^e$, $R^f$, $R^g$ and $R^h$ is hydrogen and the sum of s, t, u and v is 1.

Further preferred is a compound having the formula (I), (II) or (III), wherein D and E are independently selected from CH and N.

Further preferred is a compound having the formula (I), (II) or (III), wherein D is CH and E is N.

Further preferred is a compound having the formula (I), (II) or (III), wherein D is N and E is CH.

Further preferred is a compound having the formula (I), (II) or (III), wherein L (i.e., $L_1$-$L_2$-$L_3$) is selected from

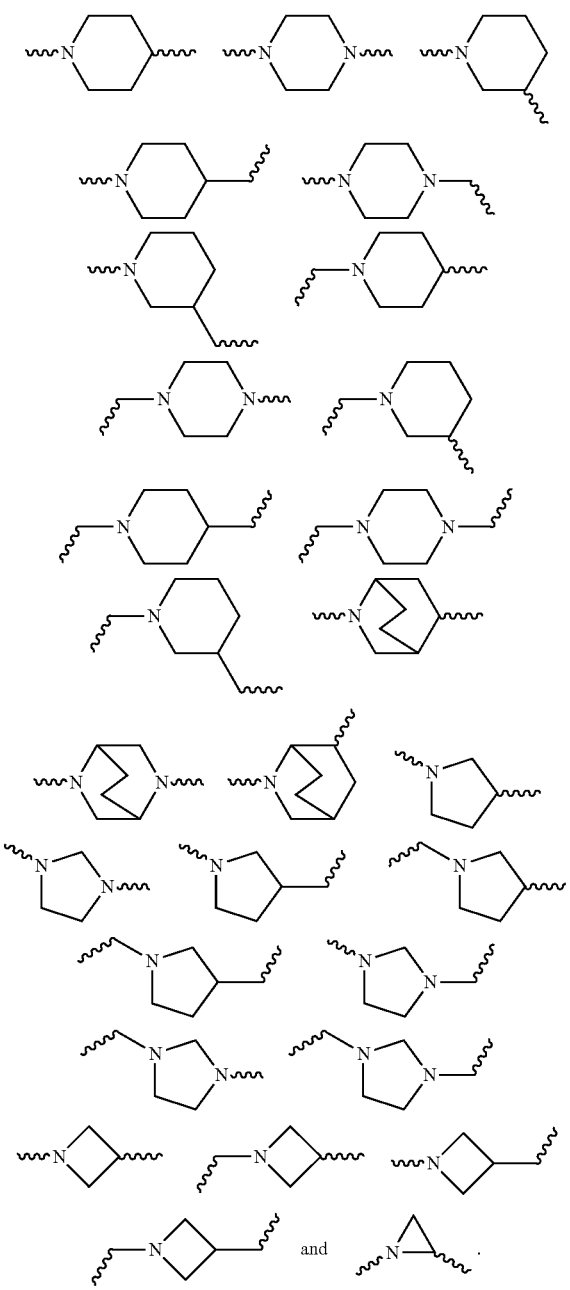

Further preferred is a compound having the formula (I), (II) or (III), wherein L (i.e., $L_1$-$L_2$-$L_3$) is selected from

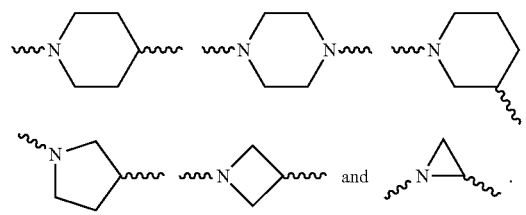

Further preferred is a compound having the formula (I), (II) or (III), wherein L (i.e., $L_1$-$L_2$-$L_3$) is selected from

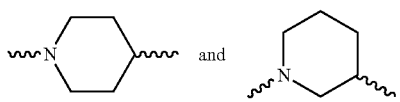

Further preferred is a compound having the formula (I), (II) or (III), wherein $L_2$ is selected from

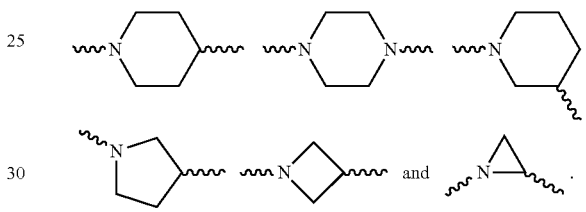

Further preferred is a compound having the formula (I), (II) or (III), wherein $L_2$ is selected from

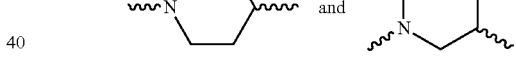

Further preferred is a compound having the formula (I), (II) or (III), wherein $L_1$ and $L_3$ are independently absent or —$CH_2$—.

Further preferred is a compound having the formula (I), (II) or (III), wherein
(i) $L_1$ and $L_3$ are absent;
(ii) $L_1$ and $L_3$ are —$CH_2$—;
(iii) $L_1$ is absent and $L_3$ is —$CH_2$—; or
(iv) $L_1$ is —$CH_2$— and $L_3$ is absent.

Further preferred is a compound having the formula (I), (II) or (III), wherein each occurrence of $R^3$ is independently hydrogen, halogen or substituted or unsubstituted $C_{1-3}$ alkyl.

Further preferred is a compound having the formula (I), (II) or (III), wherein each occurrence of $R^3$ is independently hydrogen, fluorine or methyl.

Further preferred is a compound having the formula (I), (II) or (III), wherein at least one of $R^1$ or $R^2$ is hydrogen.

Further preferred is a compound having the formula (I), (II) or (III), wherein each of $R^1$ and $R^2$ are independently selected from halogen, substituted or unsubstituted alkyl, —$NR^zR^z$, substituted or unsubstituted heterocyclyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl.

Further preferred is a compound having the formula (I), (II) or (III), wherein each of $R^1$ and $R^2$ is independently selected from —$NR^zR^z$, substituted or unsubstituted aryl and substituted or unsubstituted heteroaryl.

Further preferred is a compound having the formula (I), (II) or (III), wherein each of $R^1$ and $R^2$ is independently substituted or unsubstituted aryl.

Further preferred is a compound having the formula (I), (II) or (III), wherein each of $R^1$ and $R^2$ is independently substituted or unsubstituted heteroaryl.

Further preferred is a compound having the formula (I), (II) or (III), wherein
  (i) $R^1$ is substituted or unsubstituted aryl and $R^2$ is substituted or unsubstituted heteroaryl;
  (ii) $R^1$ is substituted or unsubstituted heteroaryl and $R^2$ is substituted or unsubstituted aryl;
  (iii) both $R^1$ and $R^2$ are, independently, substituted or unsubstituted aryl; or
  (iv) both $R^1$ and $R^2$ are, independently, substituted or unsubstituted heteroaryl.

Further preferred is a compound having the formula (I), (II) or (III), wherein each of $R^1$ and $R^2$ is independently selected from

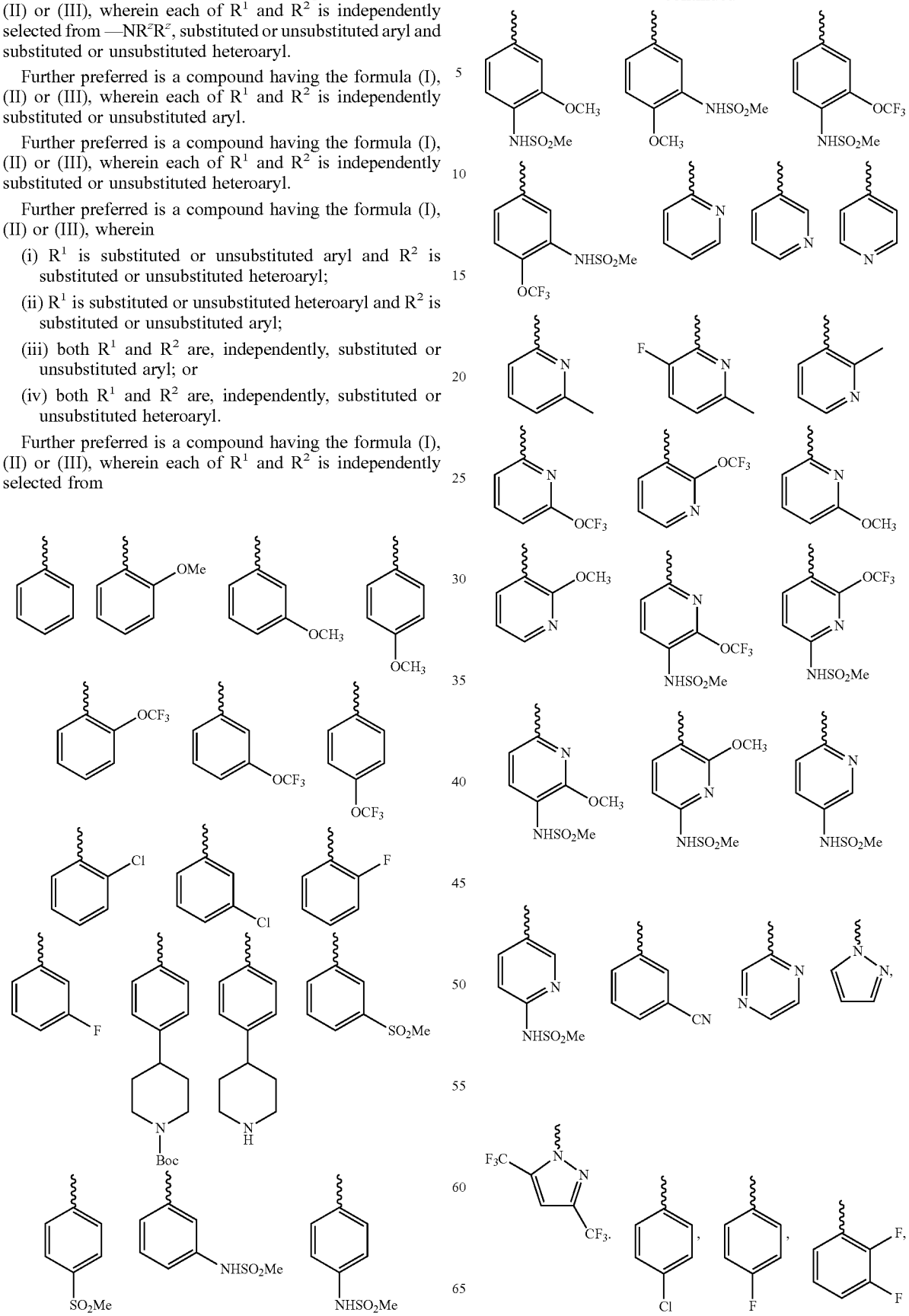

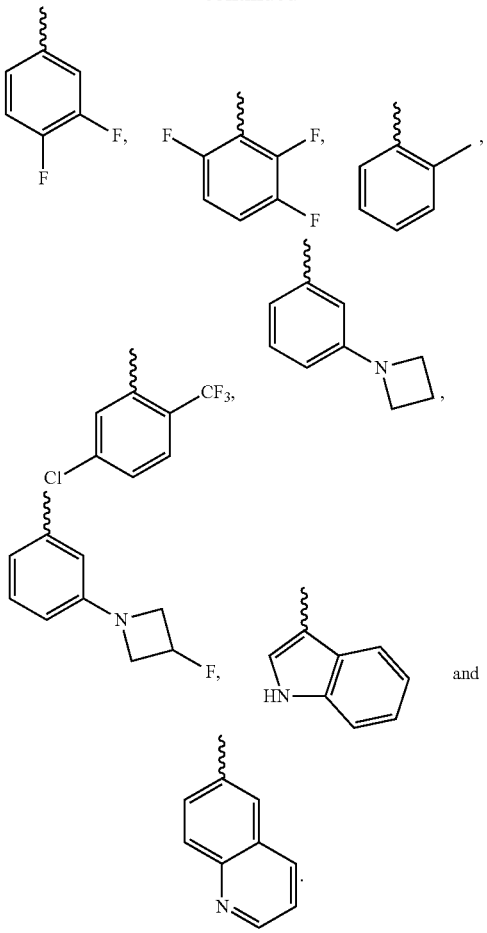

Further preferred is a compound having the formula (I), (II) or (III), wherein each of $R^x$ and $R^y$ is independently selected from hydrogen, hydroxyl or —CH$_2$OH.

Further preferred is a compound having the formula (I), (II) or (III), wherein each of $R^x$ and $R^y$ is hydrogen.

Representative compounds of the present invention include those listed below (see also Table 1) and pharmaceutically acceptable salts thereof. The present invention should not be construed to be limited to these compounds.

1. 2-(Pyridin-2-yl)-N-(5-(1-(6-(2-(3-(trifluoromethoxy)phenyl)acetamido)pyridin-3-yl) piperidin-4-yl)-1,3,4-thiadiazol-2-yl)acetamide;
2. 2-(Pyridin-2-yl)-N-(5-(1-(6-(2-(3-(trifluoromethoxy)phenyl)acetamido)pyridin-3-yl) piperidin-3-yl)-1,3,4-thiadiazol-2-yl)acetamide;
2A. (R) or (S) 2-(Pyridin-2-yl)-N-(5-(1-(6-(2-(3-(trifluoromethoxy)phenyl)acetamido) pyridin-3-yl)piperidin-3-yl)-1,3,4-thiadiazol-2-yl)acetamide;
2B. (S) or (R) 2-(Pyridin-2-yl)-N-(5-(1-(6-(2-(3-(trifluoromethoxy)phenyl)acetamido) pyridin-3-yl)piperidin-3-yl)-1,3,4-thiadiazol-2-yl)acetamide;
3. 2-(Pyridin-3-yl)-N-(5-(1-(6-(2-(3-(trifluoromethoxy)phenyl)acetamido)pyridin-3-yl) piperidin-3-yl)-1,3,4-thiadiazol-2-yl)acetamide;
3A. (R) or (S) 2-(Pyridin-3-yl)-N-(5-(1-(6-(2-(3-(trifluoromethoxy)phenyl)acetamido) pyridin-3-yl)piperidin-3-yl)-1,3,4-thiadiazol-2-yl)acetamide;
3B. (S) or (R) 2-(Pyridin-3-yl)-N-(5-(1-(6-(2-(3-(trifluoromethoxy)phenyl)acetamido) pyridin-3-yl)piperidin-3-yl)-1,3,4-thiadiazol-2-yl)acetamide;
4. 2-(Pyridin-3-yl)-N-(5-(1-(6-(2-(3-(trifluoromethoxy)phenyl)acetamido)pyridin-3-yl) piperidin-4-yl)-1,3,4-thiadiazol-2-yl)acetamide;
5. 2-(3-Cyanophenyl)-N-(5-(1-(6-(2-(3-(trifluoromethoxy)phenyl)acetamido)pyridin-3-yl)piperidin-4-yl)-1,3,4-thiadiazol-2-yl)acetamide;
6. 2-(Pyridin-2-yl)-N-(5-(4-(5-(2-(3-(trifluoromethoxy)phenyl)acetamido)-1,3,4-thiadiazol-2-yl)piperidin-1-yl)pyridin-2-yl)acetamide;
7. 2-(Pyridin-2-yl)-N-(5-(3-(5-(2-(3-(trifluoromethoxy)phenyl)acetamido)-1,3,4-thiadiazol-2-yl)piperidin-1-yl)pyridin-2-yl)acetamide;
8. 2-(pyridin-2-yl)-N-(5-(1-(6-(2-(3-(trifluoromethoxy)phenyl)acetamido)pyridazin-3-yl) piperidin-4-yl)-1,3,4-thiadiazol-2-yl) acetamide;
9. 2-(Pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide;
10. 2-(Pyridin-3-yl)-N-(5-(1-(6-(2-(3-(trifluoromethoxy) phenyl)acetamido)pyridazin-3-yl)piperidin-4-yl)-1,3,4-thiadiazol-2-yl)acetamide;
11. 2-(3-(Methylsulfonamido)phenyl)-N-(5-(1-(6-(2-(3-(trifluoromethoxy)phenyl) acetamido)pyridazin-3-yl)piperidin-4-yl)-1,3,4-thiadiazol-2-yl)acetamide;
12. 2-(2-Chlorophenyl)-N-(6-(4-(5-(2-(pyridin-2-yl)acetamido)-1,3,4-thiadiazol-2-yl) piperidin-1-yl)pyridazin-3-yl)acetamide;
13. 2-(2-Chlorophenyl)-N-(5-(1-(6-(2-(3-(trifluoromethoxy) phenyl)acetamido)pyridazin-3-yl)piperidin-3-yl)-1,3,4-thiadiazol-2-yl)acetamide;
14. 2-(2-Fluorophenyl)-N-(6-(4-(5-(2-(pyridin-2-yl)acetamido)-1,3,4-thiadiazol-2-yl) piperidin-1-yl)pyridazin-3-yl)acetamide;
15. 2-(Pyrazin-2-yl)-N-(5-(1-(6-(2-(3-(trifluoromethoxy) phenyl)acetamido)pyridazin-3-yl)piperidin-4-yl)-1,3,4-thiadiazol-2-yl)acetamide;
16. 2-(Pyridin-2-yl)-N-(5-(1-(6-(2-(3-(trifluoromethoxy) phenyl)acetamido)pyridazin-3-yl)piperidin-4-yl)-1,3,4-thiadiazol-2-yl)acetamide dihydrochloride;
17. 2-(Pyridin-2-yl)-N-(6-(4-(5-(2-(3-(trifluoromethoxy) phenyl)acetamido)-1,3,4-thiadiazol-2-yl)piperidin-1-yl) pyridazin-3-yl)acetamide;
18. 2-(Pyridin-3-yl)-N-(6-(4-(5-(2-(3-(trifluoromethoxy) phenyl)acetamido)-1,3,4-thiadiazol-2-yl)piperidin-1-yl) pyridazin-3-yl)acetamide;
19. 2-(Pyridin-3-yl)-N-(6-(4-(5-(2-(2,3,6-trifluorophenyl) acetamido)-1,3,4-thiadiazol-2-yl)piperidin-1-yl) pyridazin-3-yl)acetamide;
20. 2-(Pyridin-2-yl)-N-(6-(4-(5-(2-(2,3,6-trifluorophenyl) acetamido)-1,3,4-thiadiazol-2-yl)piperidin-1-yl) pyridazin-3-yl)acetamide;
21. 2-(2,3-Difluorophenyl)-N-(5-(1-(6-(2-(pyridin-2-yl)acetamido)pyridazin-3-yl)piperidin-4-yl)-1,3,4-thiadiazol-2-yl)acetamide;
22. 2-(3,4-Difluorophenyl)-N-(5-(1-(6-(2-(pyridin-2-yl)acetamido)pyridazin-3-yl)piperidin-4-yl)-1,3,4-thiadiazol-2-yl)acetamide;
23. 2-(2-Fluorophenyl)-N-(5-(1-(6-(2-(pyridin-2-yl)acetamido)pyridazin-3-yl)piperidin-4-yl)-1,3,4-thiadiazol-2-yl)acetamide;
24. 2-(3-Fluorophenyl)-N-(5-(1-(6-(2-(pyridin-2-yl)acetamido)pyridazin-3-yl)piperidin-4-yl)-1,3,4-thiadiazol-2-yl)acetamide;
25. 2-(4-Fluorophenyl)-N-(5-(1-(6-(2-(pyridin-2-yl)acetamido)pyridazin-3-yl)piperidin-4-yl)-1,3,4-thiadiazol-2-yl)acetamide;

26. 2-(2-Methoxyphenyl)-N-(5-(1-(6-(2-(pyridin-2-yl)acetamido)pyridazin-3-yl)piperidin-4-yl)-1,3,4-thiadiazol-2-yl)acetamide;
27. 2-(2-Chlorophenyl)-N-(5-(1-(6-(2-(pyridin-2-yl)acetamido)pyridazin-3-yl)piperidin-4-yl)-1,3,4-thiadiazol-2-yl)acetamide;
28. 2-(5-Chloro-2-(trifluoromethyl)phenyl)-N-(5-(1-(6-(2-(pyridin-2-yl)acetamido) pyridazin-3-yl)piperidin-4-yl)-1,3,4-thiadiazol-2-yl)acetamide;
29. 2-(4-Chlorophenyl)-N-(5-(1-(6-(2-(pyridin-2-yl)acetamido)pyridazin-3-yl)piperidin-4-yl)-1,3,4-thiadiazol-2-yl)acetamide;
30. 2-(Quinolin-6-yl)-N-(5-(1-(6-(2-(3-(trifluoromethoxy)phenyl)acetamido)pyridazin-3-yl)piperidin-4-yl)-1,3,4-thiadiazol-2-yl)acetamide;
31. 2-o-Tolyl-N-(5-(1-(6-(2-(3-(trifluoromethoxy)phenyl)acetamido)pyridazin-3-yl) piperidin-4-yl)-1,3,4-thiadiazol-2-yl)acetamide;
32. N-(6-(4-(5-(2-(1H-indol-3-yl)acetamido)-1,3,4-thiadiazol-2-yl)piperidin-1-yl) pyridazin-3-yl)-2-(3-(trifluoromethoxy)phenyl)acetamide;
33. 2-(2-Fluorophenyl)-N-(6-(4-(5-(2-(pyrazin-2-yl)acetamido)-1,3,4-thiadiazol-2-yl) piperidin-1-yl)pyridazin-3-yl)acetamide;
34. 2-(3-(Azetidin-1-yl)phenyl)-N-(5-(1-(6-(2-(3-(trifluoromethoxy)phenyl)acetamido) pyridazin-3-yl)piperidin-4-yl)-1,3,4-thiadiazol-2-yl)acetamide;
35. 2-(3-Chlorophenyl)-N-(5-(1-(6-(2-(pyridin-2-yl)acetamido)pyridazin-3-yl)piperidin-4-yl)-1,3,4-thiadiazol-2-yl)acetamide;
36. 3-Hydroxy-2-phenyl-N-(5-(1-(6-(2-(3-(trifluoromethoxy)phenyl)acetamido) pyridazin-3-yl)piperidin-4-yl)-1,3,4-thiadiazol-2-yl)propanamide;
37. (R)-2-hydroxy-2-phenyl-N-(5-(1-(6-(2-(3-(trifluoromethoxy)phenyl)acetamido) pyridazin-3-yl)piperidin-4-yl)-1,3,4-thiadiazol-2-yl)acetamide;
38. 2-(3-(3-Fluoroazetidin-1-yl)phenyl)-N-(5-(1-(6-(2-(3-(trifluoromethoxy)phenyl) acetamido)pyridazin-3-yl)piperidin-4-yl)-1,3,4-thiadiazol-2-yl)acetamide;
39. 2-(Pyridin-2-yl)-N-(5-((1-(6-(2-(3-(trifluoromethoxy)phenyl)acetamido)pyridazin-3-yl) piperidin-4-yl) methyl)-1,3,4-thiadiazol-2-yl)acetamide;

or a pharmaceutically acceptable salt thereof.

TABLE 1

| Ex. | Structure |
| --- | --- |
| 1 | 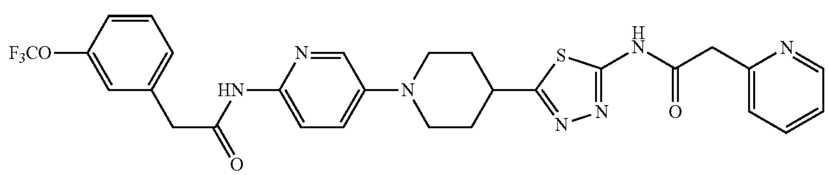 [SMILES: O=C(Cc1cccc(OC(F)(F)F)c1)Nc1ccc(N2CCC(c3nnc(NC(=O)Cc4ccccn4)s3)CC2)cn1] |
| 2 | 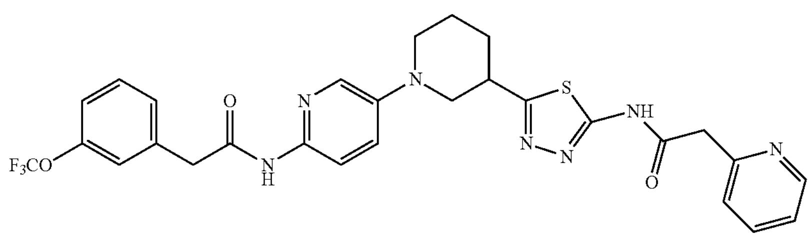 [SMILES: O=C(Cc1cccc(OC(F)(F)F)c1)Nc1ccc(N2CCCC(c3nnc(NC(=O)Cc4ccccn4)s3)C2)cn1] |
| 2A | 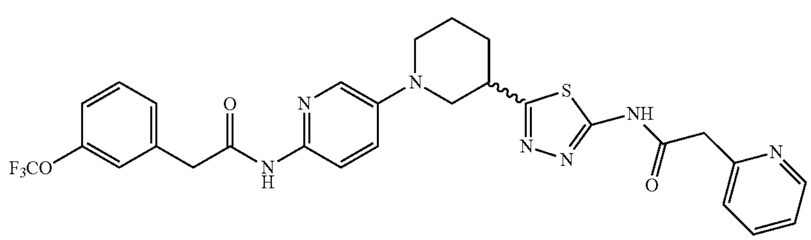 [SMILES: O=C(Cc1cccc(OC(F)(F)F)c1)Nc1ccc(N2CCCC(c3nnc(NC(=O)Cc4ccccn4)s3)C2)cn1] |
| 2B | 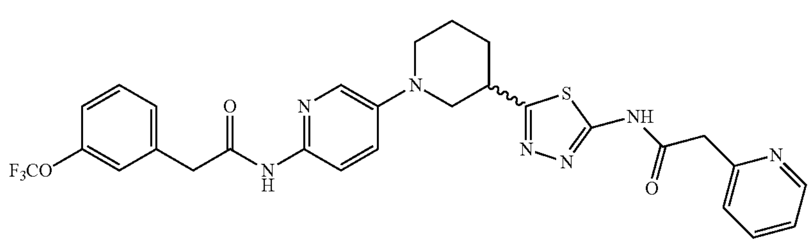 [SMILES: O=C(Cc1cccc(OC(F)(F)F)c1)Nc1ccc(N2CCCC(c3nnc(NC(=O)Cc4ccccn4)s3)C2)cn1] |

TABLE 1-continued
| Ex. | Structure |
|---|---|
| 3 | 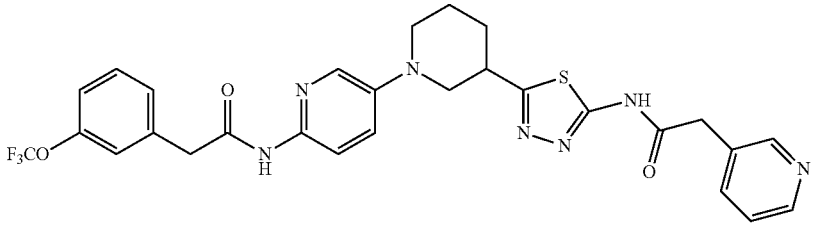 [SMILES: O=C(Cc1cccc(OC(F)(F)F)c1)Nc1ccc(N2CCCC(c3nnc(NC(=O)Cc4cccnc4)s3)C2)cn1] |
| 3A | 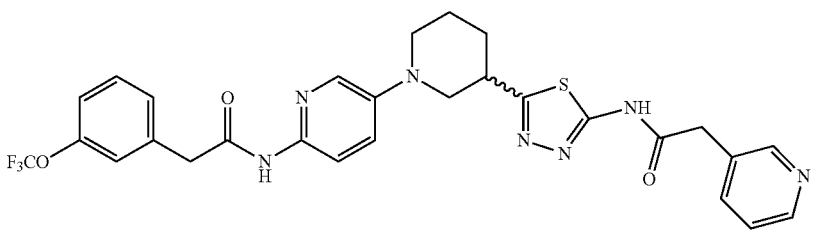 [SMILES: O=C(Cc1cccc(OC(F)(F)F)c1)Nc1ccc(N2CCCC(c3nnc(NC(=O)Cc4cccnc4)s3)C2)cn1] |
| 3B | 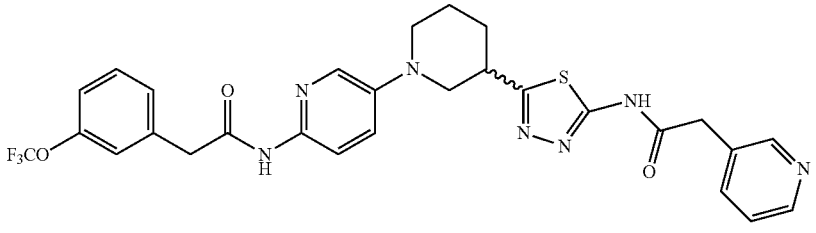 [SMILES: O=C(Cc1cccc(OC(F)(F)F)c1)Nc1ccc(N2CCCC(c3nnc(NC(=O)Cc4cccnc4)s3)C2)cn1] |
| 4 | 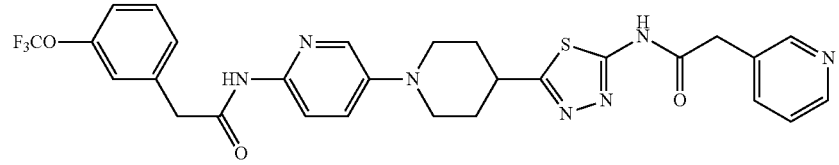 [SMILES: O=C(Cc1cccc(OC(F)(F)F)c1)Nc1ccc(N2CCC(c3nnc(NC(=O)Cc4cccnc4)s3)CC2)cn1] |
| 5 | 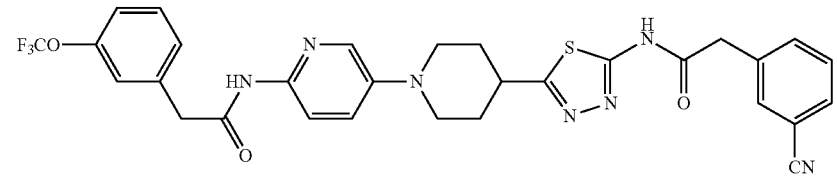 [SMILES: N#Cc1cccc(CC(=O)Nc2nnc(C3CCN(c4ccc(NC(=O)Cc5cccc(OC(F)(F)F)c5)nc4)CC3)s2)c1] |
| 6 | 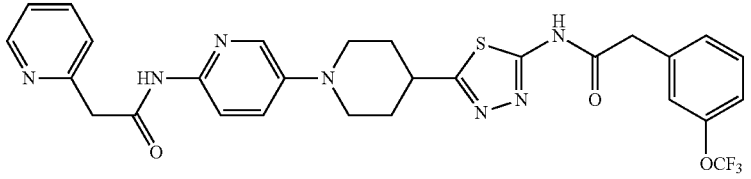 |
| 7 | 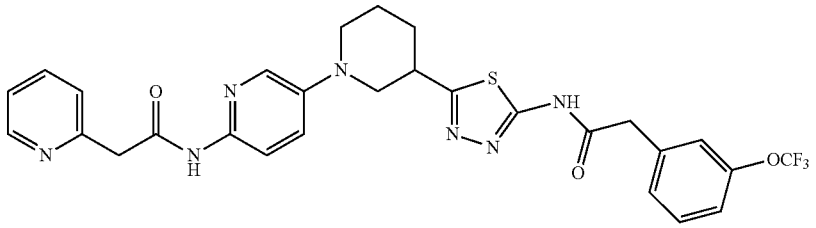 [SMILES: O=C(Cc1ccccn1)Nc1ccc(N2CCCC(c3nnc(NC(=O)Cc4cccc(OC(F)(F)F)c4)s3)C2)cn1] |

TABLE 1-continued

| Ex. | Structure |
|---|---|
| 8 | (chemical structure) |
| 9 | (chemical structure) |
| 10 | (chemical structure) |
| 11 | (chemical structure) |
| 12 | (chemical structure) |
| 13 | (chemical structure) |
| 14 | (chemical structure) |
| 15 | (chemical structure) |

TABLE 1-continued
| Ex. | Structure |
|---|---|
| 16 | 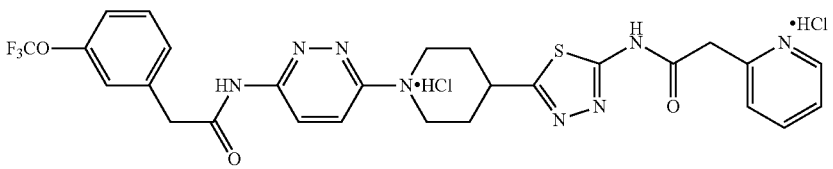 |
| 17 | 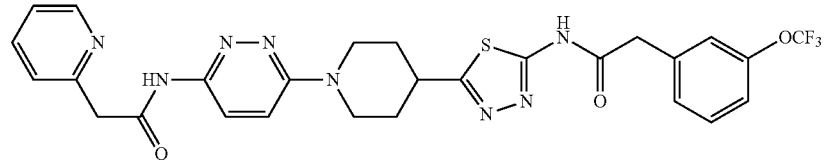 [SMILES: O=C(Cc1ccccn1)Nc1ccc(N2CCC(c3nnc(NC(=O)Cc4cccc(OC(F)(F)F)c4)s3)CC2)nn1] |
| 18 | 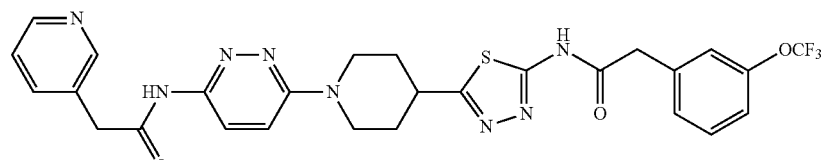 |
| 19 | 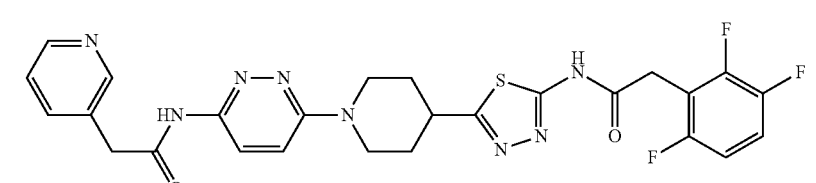 |
| 20 | 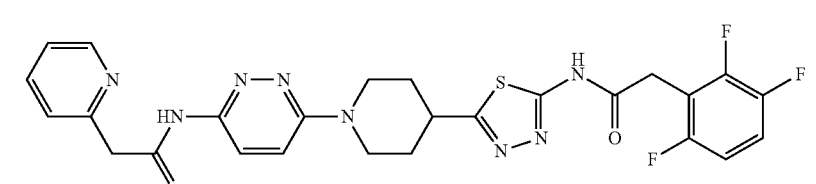 |
| 21 | 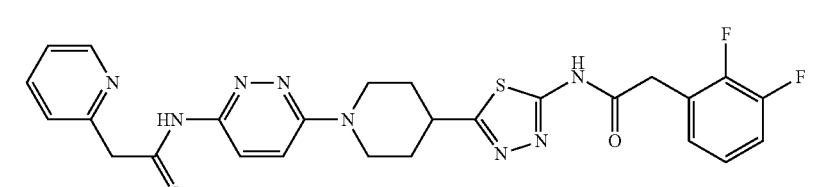 |
| 22 | 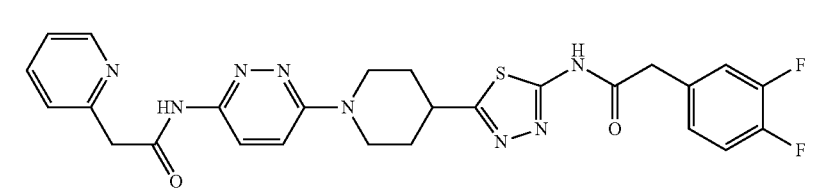 [SMILES: O=C(Cc1ccccn1)Nc1ccc(N2CCC(c3nnc(NC(=O)Cc4ccc(F)c(F)c4)s3)CC2)nn1] |
| 23 | 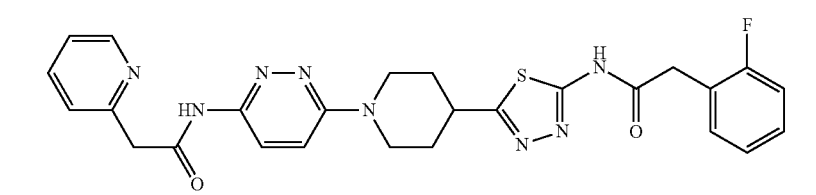 [SMILES: O=C(Cc1ccccn1)Nc1ccc(N2CCC(c3nnc(NC(=O)Cc4ccccc4Cl)s3)CC2)nn1] |

TABLE 1-continued
| Ex. | Structure |
|---|---|
| 24 | 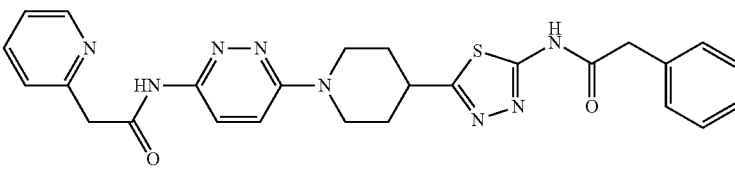 |
| 25 | 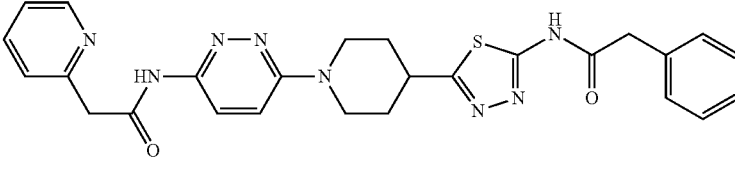 |
| 26 | 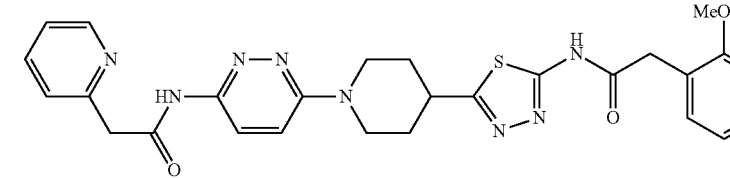 |
| 27 | 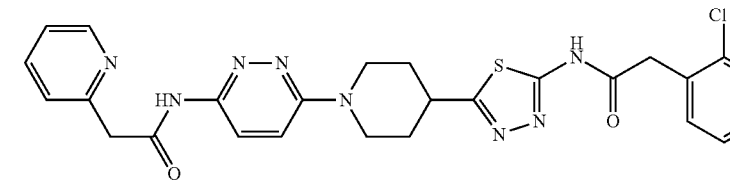 |
| 28 | 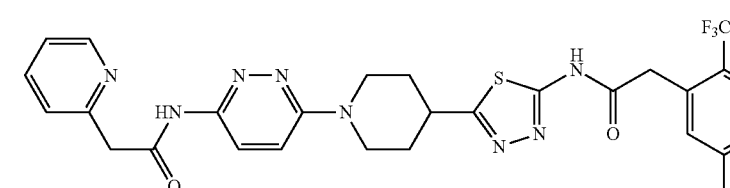 |
| 29 | 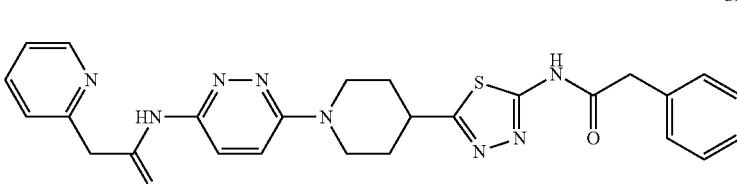 |
| 30 | 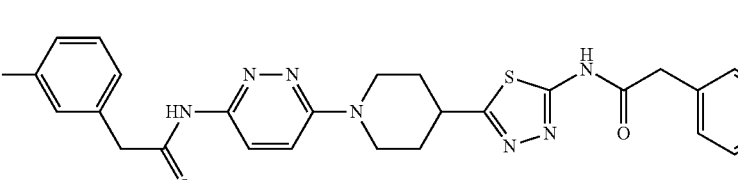 |
| 31 | 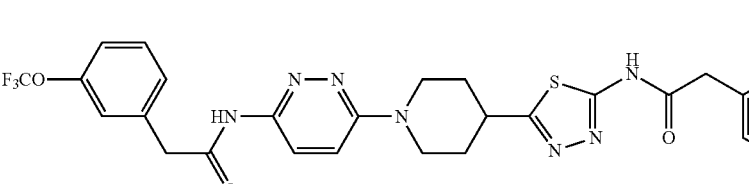 |

TABLE 1-continued

| Ex. | Structure |
|---|---|
| 32 | (structure) |
| 33 | (structure) |
| 34 | (structure) |
| 35 | (structure) |
| 36 | (structure) |
| 37 | (structure) |
| 38 | (structure) |

TABLE 1-continued

| Ex. | Structure |
|---|---|
| 39 | 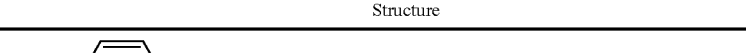 |

Yet another embodiment of the present invention is a method for inhibiting glutaminase in a patient by administering to the patient an effective amount of at least one compound of the present invention (for example, a compound of formula (I), (II) or (III) as defined above).

Yet another embodiment of the present invention is a method for treating an inflammatory, autoimmune or proliferative disease (e.g., via inhibition of glutaminase) by administering to a patient in need of such treatment an effective amount of at least one compound of the present invention. In one embodiment, the compound of the present invention inhibits glutaminase (i.e., an effective amount of the compound is administered to inhibit glutaminase).

Yet another embodiment of the present invention is a method for treating a inflammatory, autoimmune or proliferative disease (e.g., via inhibition of glutaminase) by administering to a patient in need of such treatment an effective amount of at least one compound of the present invention, in combination (simultaneously or sequentially) with at least one other anti-inflammatory, immunomodulator or anti-cancer agent. In one embodiment, the compound of the present invention inhibits glutaminase.

More particularly, the compounds of formula (I) to (III) and pharmaceutically acceptable esters or salts thereof can be administered for the treatment, prevention and/or amelioration of diseases or disorders associated with glutamine, in particular the amelioration of diseases or disorders mediated by glutamine, including, but not limited to, inflammatory diseases or disorders, autoimmune diseases or disorders, and cancer and other proliferative diseases or disorders.

The compounds of the present invention are useful in the treatment of a variety of cancers, including, but not limited to:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of glutaminase and glutamine in the regulation of cellular proliferation, the glutaminase inhibitors of the present invention may act as reversible cytostatic agents and therefore may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritic disease (e.g., arthritis), psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including but not limited to HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds described herein are also useful in inhibiting tumor angiogenesis and metastasis. One embodiment of the invention is a method of inhibiting tumor angiogenesis or metastasis in a patient in need thereof by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of one or more compounds of the present invention.

Examples of immune disorders include, but are not limited to, psoriasis, rheumatoid arthritis, vasculitis, inflammatory bowel disease, dermatitis, osteoarthritis, asthma, inflammatory muscle disease, allergic disease (e.g., allergic rhinitis), vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease by administering an effective amount of one or more compounds of the present invention.

The compounds of the present invention are also useful in combination (administered together or sequentially) with known anti-cancer treatments, such as radiation therapy or with cytostatic, cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The compounds of the present invention are also useful in combination (administered together or sequentially) with one or more steroidal anti-inflammatory drugs, non-steroidal anti-inflammatory drugs (NSAIDs) or immune selective anti-inflammatory derivatives (ImSAIDs).

The invention further provides a pharmaceutical composition comprising one or more compounds of the present invention (such as a compound having formula (I), (II) or (III)) together with a pharmaceutically acceptable carrier. The pharmaceutical composition may further comprise one or more of the active ingredients identified above, such as other steroidal anti-inflammatory drugs, non-steroidal anti-inflammatory drugs (NSAIDs), immune selective anti-inflammatory derivatives (ImSAIDs) or anti-cancer agents.

In one embodiment, the pharmaceutical composition includes a therapeutically effective amount of one or more compounds of formula (I), (II) or (III).

Yet another embodiment is a method of treating autoimmune disorders in a patient in need thereof by administering a therapeutically effective amount of a compound of the present invention. For example, the compounds of the present invention are effective for treating asthma, chronic obstructive pulmonary disease (COPD), rheumatoid arthritis, psoriasis, lupus and experimental autoimmune encephalomyelitis (EAE).

Yet another embodiment is a method of treating allergic rhinitis in a patient in need thereof by administering a therapeutically effective amount of a compound of the present invention.

Yet another embodiment is a method of treating cancer in a patient in need thereof by administering a therapeutically effective amount of a compound of the present invention. For example, the compounds of the present invention are effective for treating hematopoietic tumors of lymphoid lineage, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, acute myelogenous leukemias, chronic myelogenous leukemias, myelodysplastic syndrome and promyelocytic leukemia. The compounds of the present invention are also effective for treating carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma, tumors of mesenchymal origin, fibrosarcoma, rhabdomyosarcoma, tumors of the central and peripheral nervous system, astrocytoma, neuroblastoma, glioma, schwannoma, melanoma, seminoma, teratocarcinoma, osteosarcoma, xenoderoma pigmentosum, keratoctanthoma, thyroid follicular cancer and Kaposi's sarcoma.

Yet another embodiment is a method of treating leukemia in a patient in need thereof by administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), acute lymphoblastic leukemia (ALL), multiple myeloma (MM), small lymphocytic lymphoma (SLL), and indolent non-Hodgkin's lymphoma (I-NHL).

DETAILED DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl group as defined above having up to 6 carbon atoms. The term "$C_{1-3}$ alkyl" refers to an alkyl group as defined above having up to 3 carbon atoms. In appropriate circumstances, the term "alkyl" refers to a hydrocarbon chain radical as mentioned above which is bivalent.

The term "alkenyl", unless otherwise specified, refers to an aliphatic hydrocarbon group containing one or more carbon-carbon double bonds and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl. The term "$C_{2-6}$ alkenyl" refers to an alkenyl group as defined above having up to 6 carbon atoms. In appropriate circumstances, the term "alkenyl" refers to a hydrocarbon group as mentioned above which is bivalent.

The term "alkynyl", unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butnyl. The term "$C_{2-6}$ alkynyl" refers to an alkynyl group as defined above having up to 6 carbon atoms. In appropriate circumstances, the term "alkynyl" refers to a hydrocarbyl radical as mentioned above which is bivalent.

The term "alkoxy" unless otherwise specified, denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O-(substituted alkyl). For example "alkoxy" refers to the group —O-alkyl, including from 1 to 8 carbon atoms of a straight, branched, cyclic configuration and combinations thereof attached to the parent structure through an oxygen atom. Examples include methoxy, ethoxy, propoxy, isopropoxy, cyclopropyloxy, and cyclohexyloxy. In appropriate circumstances, the term "alkoxy" refers to a group as mentioned above which is bivalent.

The term "cycloalkyl", unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl. The term "$C_{3-6}$ cycloalkyl" refers to a cycloalkyl group as defined above having up to 6 carbon atoms.

The term "cycloalkylalkyl", unless otherwise specified, refers to a cyclic ring-containing radical containing in the range of about 3 up to 8 carbon atoms directly attached to an alkyl group which is then attached to the main structure at any carbon from the alkyl group, such as cyclopropylmethyl, cyclobutylethyl, and cyclopentylethyl.

The term "cycloalkenyl", unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which is then attached to the main structure at any carbon from the alkyl group.

The term "aryl", unless otherwise specified, refers to aromatic radicals having in the range of 6 up to 20 carbon atoms such as phenyl, naphthyl, tetrahydronaphthyl, indanyl, and biphenyl.

The term "arylalkyl", unless otherwise specified, refers to an aryl group as defined above directly bonded to an alkyl group as defined above, e.g., —$CH_2C_6H_5$ and —$C_2H_5C_6H_5$.

The term "heterocyclic ring", unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom.

The term "heterocyclyl", unless otherwise specified, refers to a heterocylic ring radical as defined above. The heterocylcyl ring radical may be attached to the main structure at any heteroatom or carbon atom. In appropriate circumstances, the term "heterocyclyl" refers to a hydrocarbon chain radical as mentioned above which is bivalent.

The term "heterocyclylalkyl", unless otherwise specified, refers to a heterocylic ring radical as defined above directly bonded to an alkyl group. The heterocyclylalkyl radical may be attached to the main structure at any carbon atom in the alkyl group. Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl", unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl.

The heteroaryl ring radical may be attached to the main structure at any heteroatom or carbon atom. The term "substituted heteroaryl" also includes ring systems substituted with one or more oxide (—O—) substituents, such as pyridinyl N-oxides.

The term "heteroarylalkyl", unless otherwise specified, refers to a heteroaryl ring radical as defined above directly bonded to an alkyl group. The heteroarylalkyl radical may be attached to the main structure at any carbon atom from alkyl group.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, =N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^x$ (e.g., R$^x$ can be hydrogen or C$_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH$_2$CH$_2$SO$_2$Ph, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Non-limiting examples of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}$C- or $^{14}$C-enriched carbon.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and (Me)$_2$SO$_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides (e.g., hydrochlorides), acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: AIDS=Acquired Immuno Deficiency Syndrome; HIV=Human Immunodeficiency Virus; Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried. In one embodiment, the amount of compound administered ranges from about 0.1 mg to 5 g, from about 1 mg to 2.0 g, from about 100 mg to 1.5 g, from about 200 mg to 1.5 g, from about 400 mg to 1.5 g, and from about 400 mg to 1.0 g.

As used herein, "treatment," "treating," or "ameliorating" are used interchangeably. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications (e.g., dogs, cats, cows, sheep, pigs, horses, goats, chickens, turkeys, ducks, and geese).

In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including without limitation x-rays, gamma rays, and neutrons.

The term "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defence system as well as conditions associated with reactions of the non-specific defence system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents. "Transplant rejection" (or "transplantation rejection") as used herein refers to any immune response directed against grafted tissue (including organs or cells (e.g., bone marrow), characterized by a loss of function of the grafted and surrounding tissues, pain, swelling, leukocytosis, and thrombocytopenia). "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "In vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a glutaminase inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The invention provides a pharmaceutical composition comprising one or more compounds of the present invention. The pharmaceutical composition may include one or more additional active ingredients as described herein. The pharmaceutical composition may be administered for any of the disorders described herein.

The subject pharmaceutical compositions are typically formulated to provide a therapeutically effective amount of a compound of the present invention as the active ingredient.

Where desired, the pharmaceutical compositions contain a compound of the present invention as the active ingredient and one or more pharmaceutically acceptable carriers or excipients, such as inert solid diluents and fillers, diluents, including sterile aqueous solution and various organic solvents, permeation enhancers, solubilizers and adjuvants.

The pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

Methods include administration of a compound of the present invention by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, and combinations thereof.

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

The compounds or pharmaceutical composition of the present invention can be administered by any route that enables delivery of the compounds to the site of action, such as oral routes, intraduodenal routes, parenteral injection (including intravenous, intraarterial, subcutaneous, intramuscular, intravascular, intraperitoneal or infusion), topical administration (e.g. transdermal application), rectal administration, via local delivery by catheter or stent or through inhalation. The compounds can also be administered intraadiposally or intrathecally.

The compositions can be administered in solid, semisolid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, capsules, suppositories, pellets, pills, troches, and lozenges. The type of packaging will generally depend on the desired route of administration. Implantable sustained release formulations are also contemplated, as are transdermal formulations.

Method of Treatment

The invention also provides methods of using the compounds or pharmaceutical compositions of the present invention to treat disease conditions, including, but not limited to, diseases associated with overexpression of glutaminase and/or due to an excess of glutamine.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to the mammal a therapeutically effective amount of a compound of the present invention.

It will be appreciated that the treatment methods of the invention are useful in the fields of human medicine and veterinary medicine. Thus, the individual to be treated may be a mammal, preferably human, or other animal. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In some embodiments, the method of treating inflammatory or autoimmune diseases comprises administering to a subject (e.g. a mammal) a therapeutically effective amount of one or more compounds of the present invention that inhibits glutaminase. Such inhibition of glutaminase may be advantageous for treating any of the diseases or conditions described herein. For example, inhibition of glutaminase may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Inhibition of glutaminase may further provide for a reduction in the inflammatory or undesirable immune response without a concomittant reduction in the ability to reduce a bacterial, viral, and/or fungal infection.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. lymphoma and Kaposi's sarcoma) or viral-induced cancer. In some embodiments, said method relates to the treatment of a non-cancerous hyperproliferative disorder such as benign hyperplasia of the skin (e. g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more compounds or pharmaceutical compositions described herein to the eye of a subject.

The invention further provides methods of inhibiting glutaminase by contacting a glutaminase with an amount of a compound of the invention sufficient to inhibit the activity of the glutaminase enzyme. In some embodiments, the invention provides methods of inhibiting glutaminase enzyme activity by contacting a glutaminase enzyme with an amount of a compound of the invention sufficient to inhibit the activity of the glutaminase enzyme. In some embodiments, the invention provides methods of inhibiting glutaminase enzyme activity. Such inhibition can take place in solution, in a cell expressing one or more glutaminase enzyme, in a tissue comprising a cell expressing the glutaminase, or in an organism expressing glutaminase. In some embodiments, the invention provides methods of inhibiting glutaminase activity in an animal (including mammal such as humans) by contacting said animal with an amount of a compound of the invention sufficient to inhibit the activity of the glutaminase enzyme in said animal.

The following general methodology described herein provides the manner and process of making and using the compounds of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Illustrative compounds of the present invention include those specified above in Table 1 and pharmaceutically acceptable salts thereof. The present invention should not be construed to be limited to only these compounds.

General Methods of Preparation

The compounds of the present invention may be prepared by the following processes. Unless otherwise indicated, the variables (e.g. $R^1$, $R^2$, P, Q, A, B and L) when used in the below formulae are to be understood to represent those groups described above in relation to formula (I). These methods can similarly be applied to other compounds of formula (I) as provided herein above with or without modification.

Scheme 1:

This scheme provides a method for the preparation of compounds of formula (I) wherein $R^1$ and $R^2$ are independently substituted or unsubstituted aryl or substituted or unsubstituted heteroaryl, P and Q are independently —$NR^xC(O)$—$(CR^xR^y)_r$— or —$C(R^xR^y)_r$—$C(O)$—$NR^x$—, L is -$L_1$-$L_2$-$L_3$-, wherein $L_2$ is substituted or unsubstituted 3 to 14 membered heterocyclyl, $L_1$ and $L_3$ are absent or substituted or unsubstituted $C_{1-6}$ alkyl (such as methyl), A is

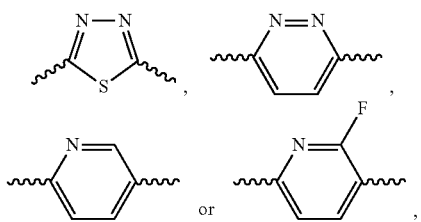

B is

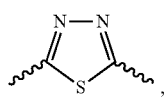

r is 0 or 1, and all the other variables (including $R^x$ and $R^y$) are as described above in relation to formula (I).

A compound of formula (1) (wherein s and v are 0 or 1 and R is alkyl) can be coupled with a compound of formula (2) to form a compound of formula (3). The compound of formula (3) can be reduced to form a compound of formula (4) using a suitable reducing agent such as, for example, Fe/NH$_4$Cl, EtOH and water. A compound of formula (4) can then be coupled with a compound of formula (5) to form a compound of formula (6), e.g., in the presence of HATU, DMF and DIPEA. The compound of formula (6) can then be hydrolysed to give a compound of formula (7), which can then be reacted with a compound of formula (8) in the presence of POCl$_3$ to form a compound of formula (9), The compound of formula (9) can then be coupled with a compound of formula (10), e.g., in the presence of HATU, DMF and DIPEA to form the compound of formula (I). This scheme is illustrated in Illustrations 1 and 2 below.

Illustration 1

Scheme 1

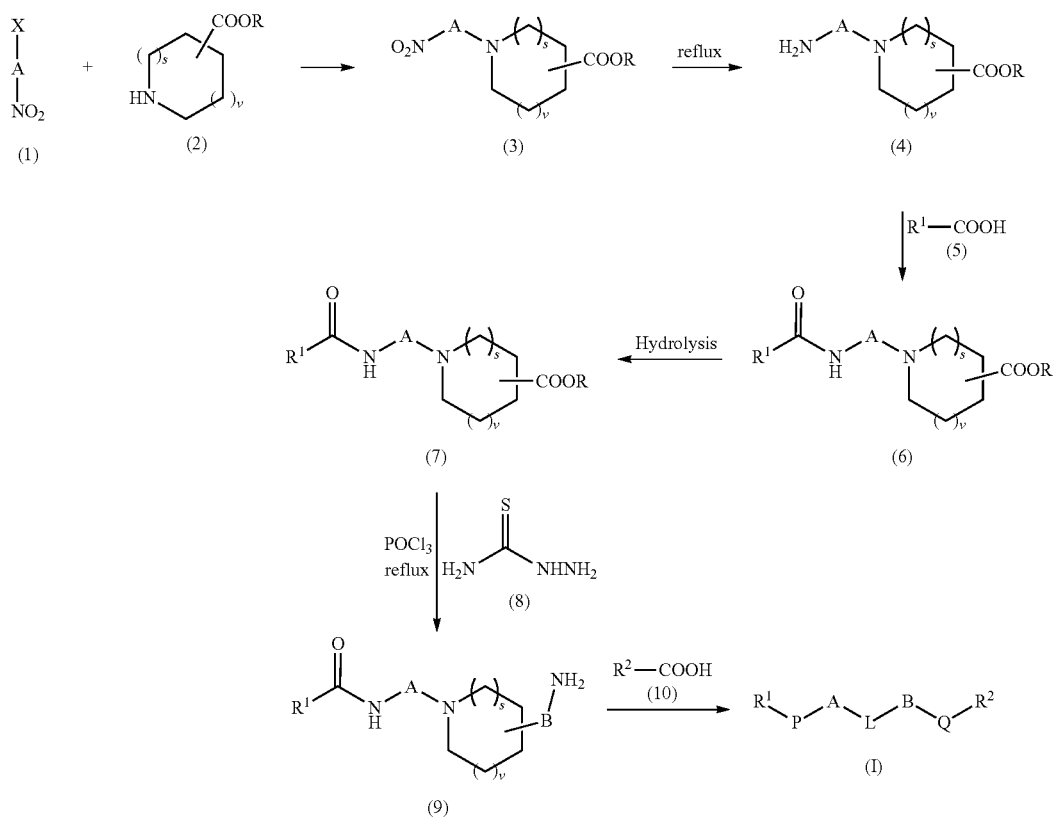

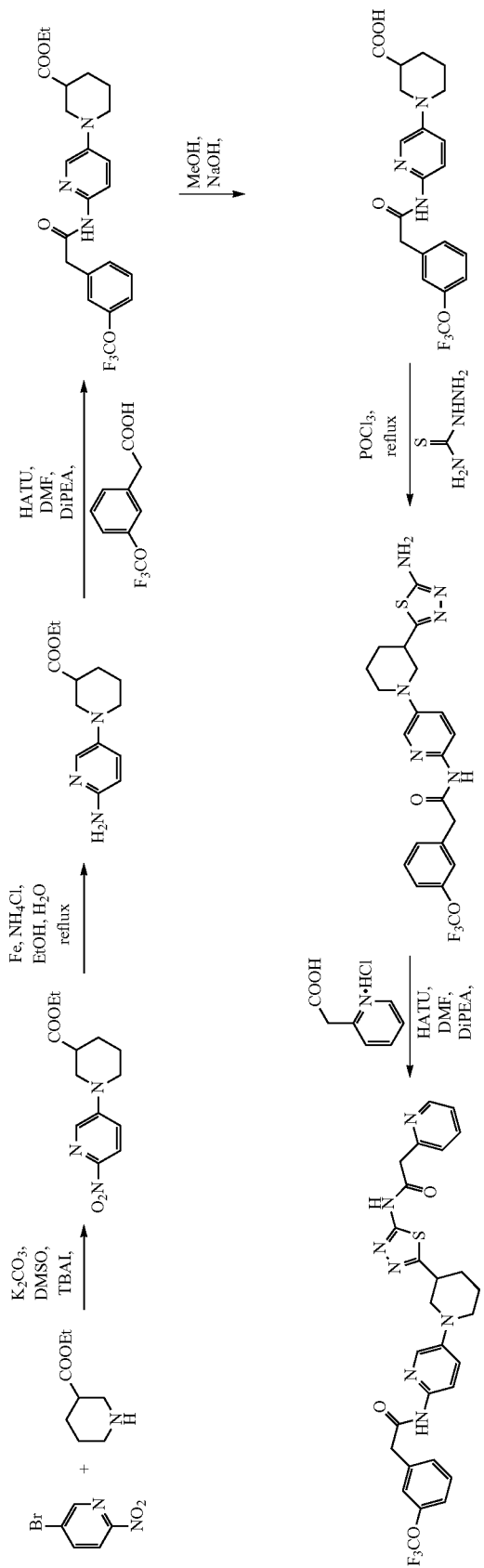

Illustration 2

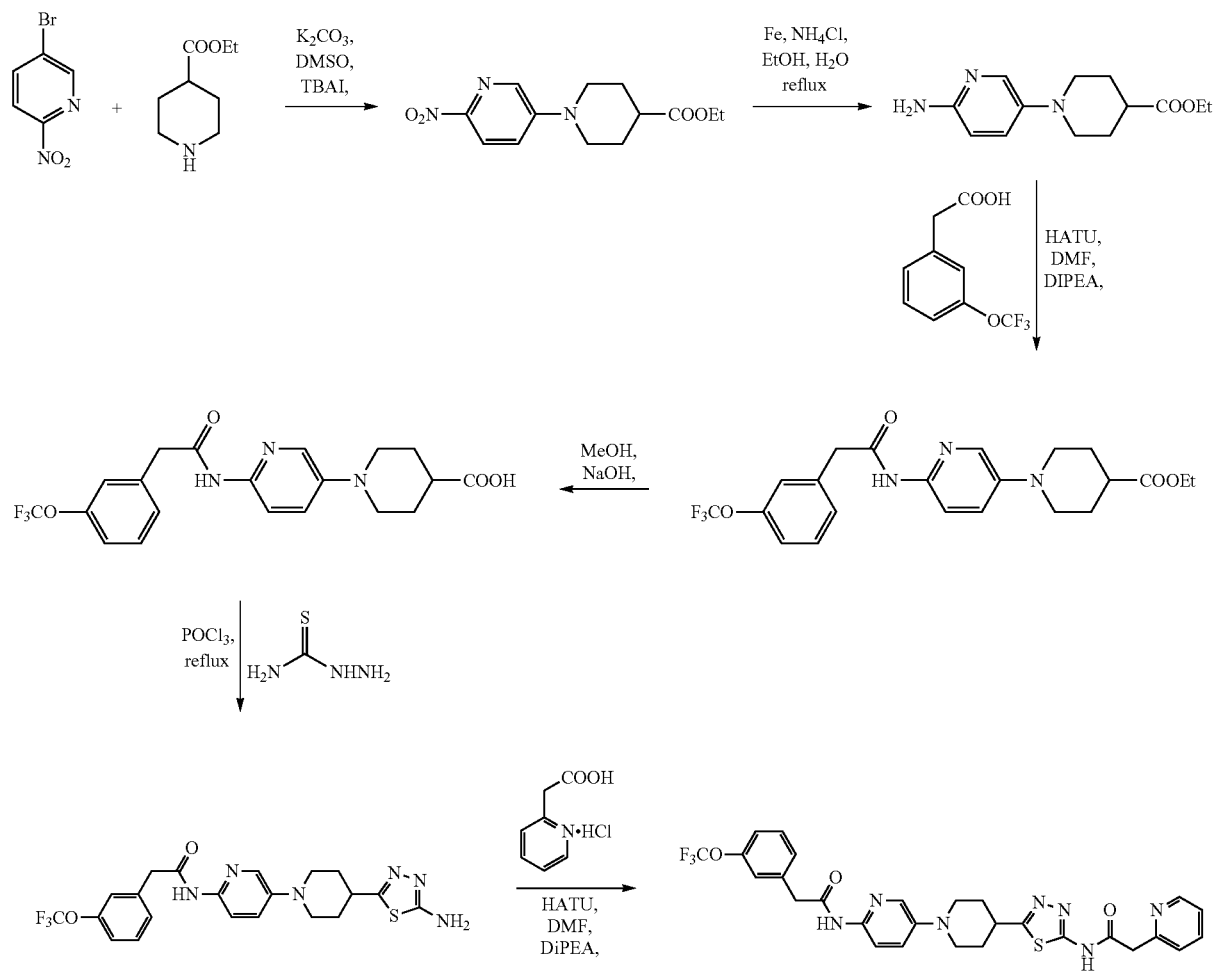

Scheme 2:

This scheme provides a method for the preparation of compounds of formula (I) wherein $R^1$ and $R^2$ are independently substituted or unsubstituted aryl or substituted or unsubstituted heteroaryl, P and Q are independently $-NR^xC(O)-(CR^xR^y)_r-$ or $-C(R^xR^y)_r-C(O)-NR^x-$, L is $-L_1-L_2-L_3-$, wherein $L_2$ is substituted or unsubstituted 3 to 14 membered heterocyclyl, $L_1$ and $L_3$ are absent or substituted or unsubstituted $C_{1-6}$ alkyl (such as methyl), A is

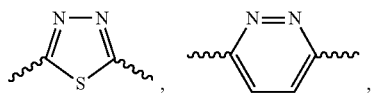

B is

-continued

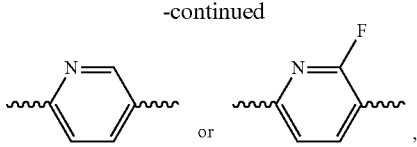

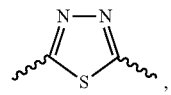

r is 0 or 1, and all the other variables (including $R^x$ and $R^y$) are as described above in relation to formula (I).

Scheme 2

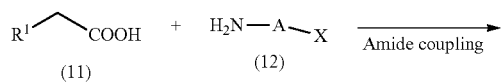

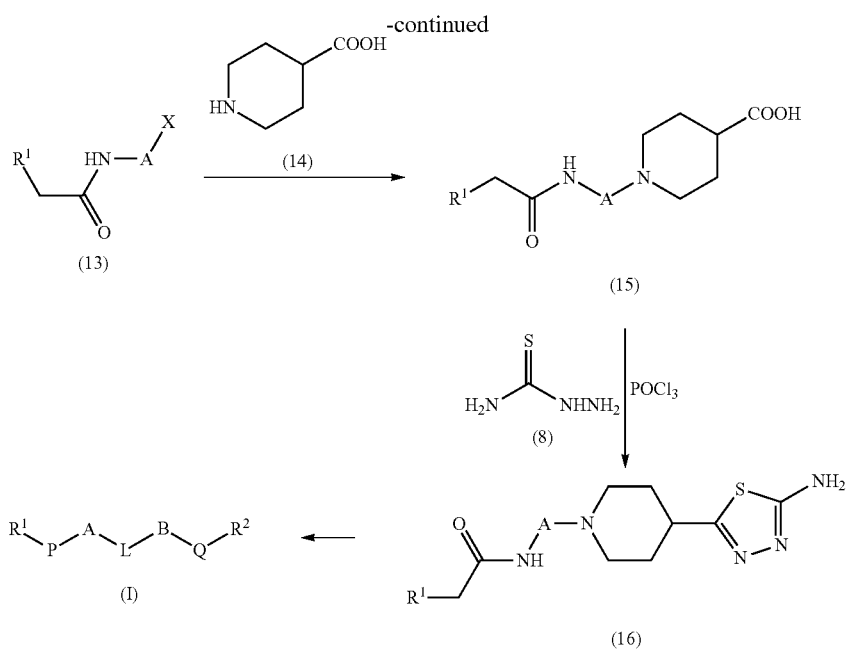

A compound of formula (11) can be coupled with a compound of formula (12) wherein X is a leaving group to form a compound of formula (13). The compound of formula (13) can be reacted with a compound of formula (14) to form a compound of formula (15), which can then be reacted with a compound of formula (8), for example, in the presence of $POCl_3$, to form a compound of formula (16). The compound of formula (16) can be coupled with a compound of formula $R^2$—$CH_2$—COOH to afford the compound of formula (I), wherein the variables are as defined above.

A compound of formula (12) can be coupled with a compound of formula (14a) to form a compound of formula (17). The compound of formula (17) can be reacted with a compound of formula $R^1$—$CH_2$—COOH followed by ester hydrolysis to form a compound of formula (15). The compound of formula (15) can then be reacted with a compound of formula (8), for example, in the presence of $POCl_3$, to form a compound of formula (16), which can be coupled with a compound of formula $R^2$—$CH_2$—COOH to give a

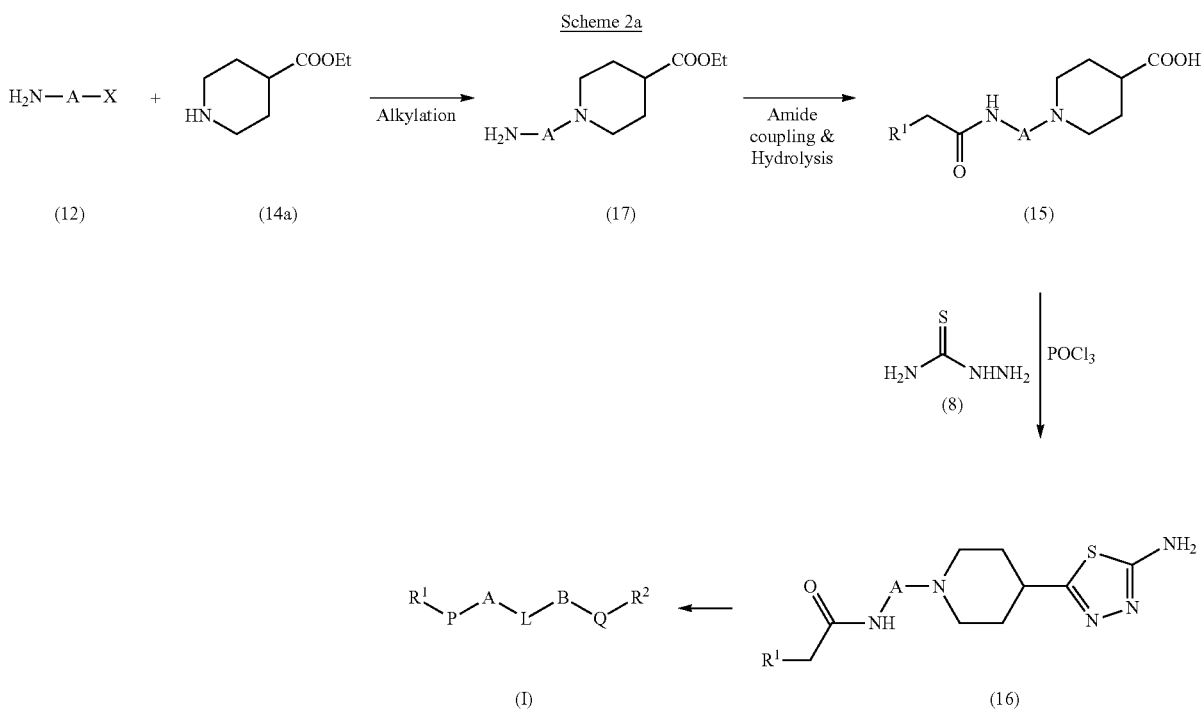

compound of formula (I), wherein the variables are as defined above. This scheme is illustrated in Illustrations 1 and 2 below.

Illustration 1

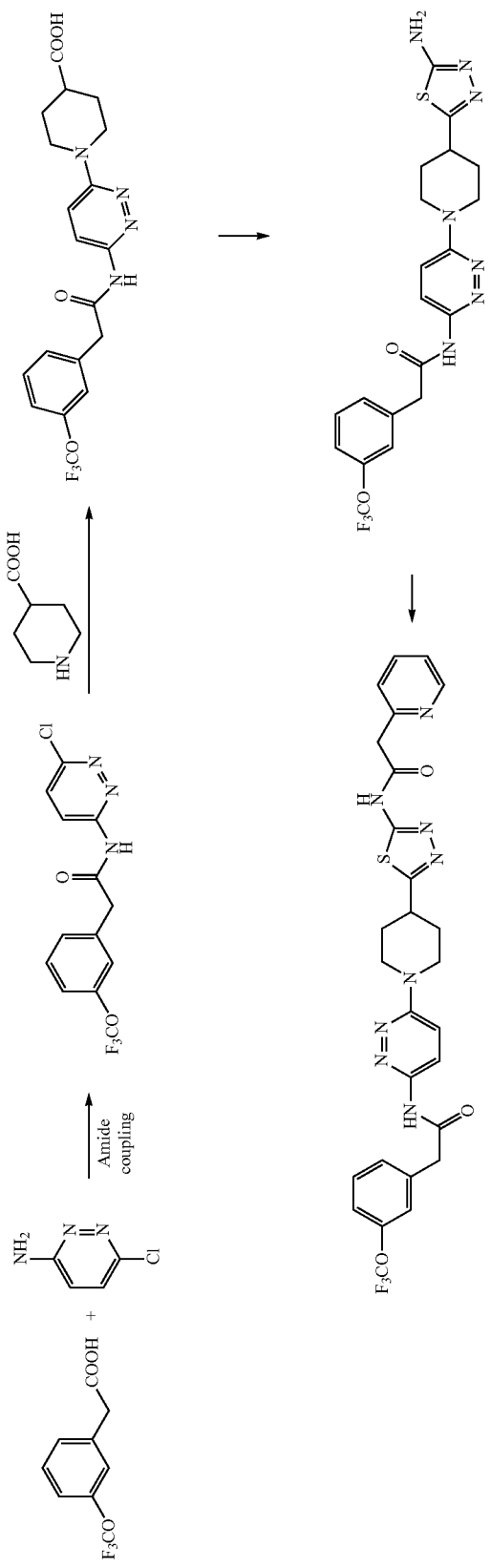

Illustration 2

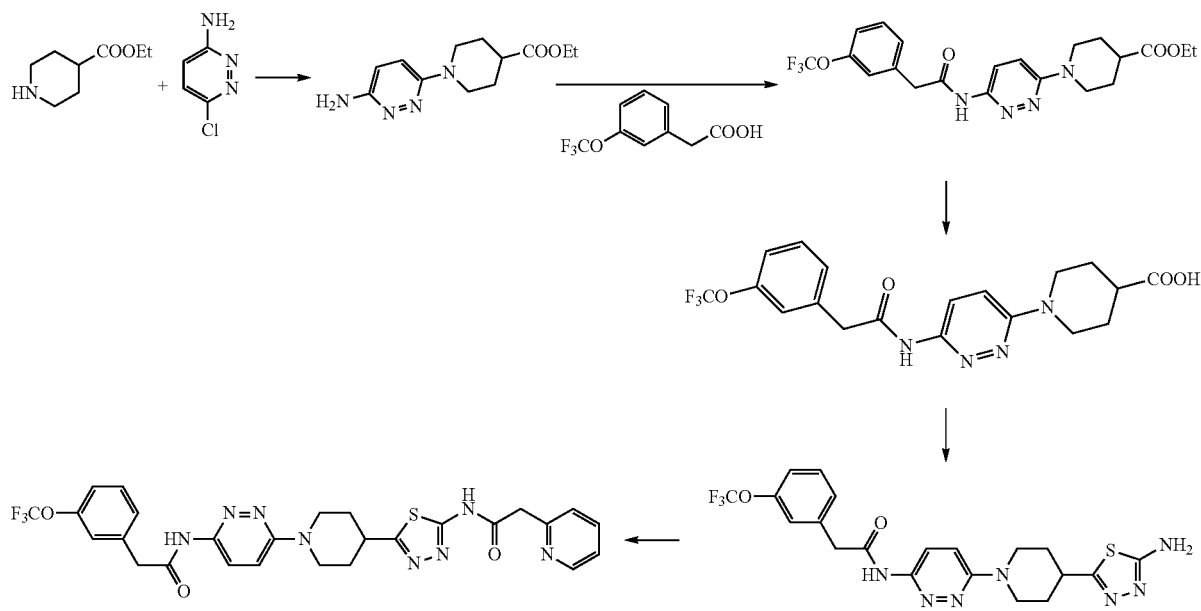

Scheme 3:

This scheme provides a method for the preparation of a compound of formula (I) wherein $R^1$ and $R^2$ are independently substituted or unsubstituted aryl or substituted or unsubstituted heteroaryl, P and Q are independently —$NR^xC(O)$—$(CR^xR^y)_r$— or —$C(R^xR^y)_r$—$C(O)$—$NR^x$—, L is -$L_1$-$L_2$-$L_3$-, wherein $L_2$ is substituted or unsubstituted 3 to 14 membered heterocyclyl, $L_1$ and $L_3$ are absent or substituted or unsubstituted $C_{1-6}$ alkyl (such as methyl), A is

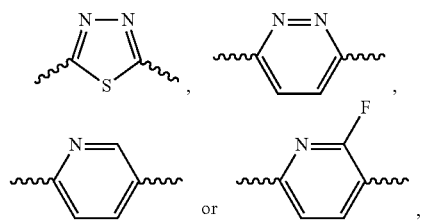

B is

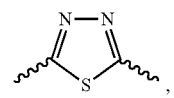

r is 0 or 1, s is 0 or 1, v is 0 or 1 and all the other variables (including $R^x$ and $R^y$) are as described above in relation to formula (I).

Step-1

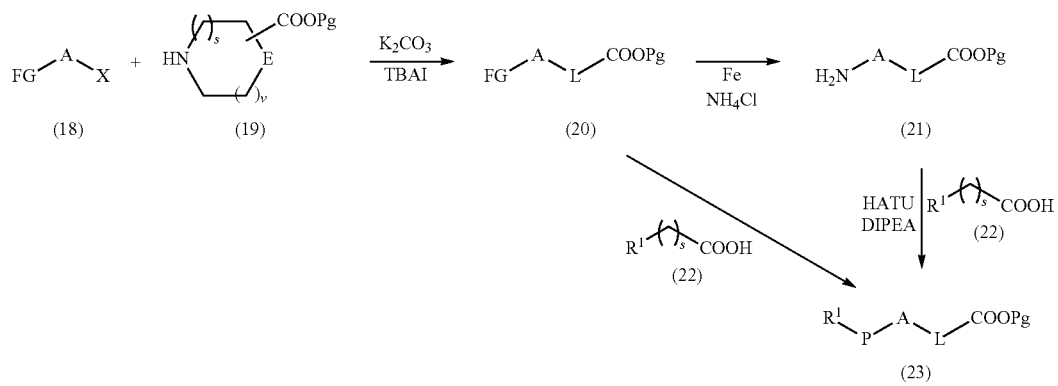

Step-2

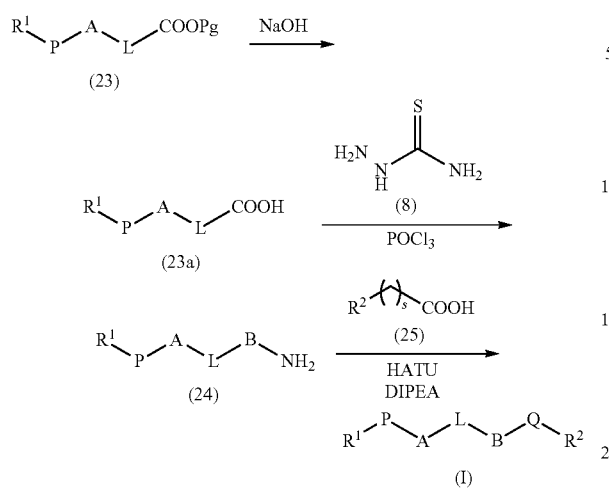

Step-1:

The compound of formula (18) wherein FG is nitro or amino and X is a leaving group such as bromine can be coupled with a compound of formula (19) wherein Pg is a protecting group optionally in the presence of tetrabutylammonium iodide (TBAI) and a suitable base such as $K_2CO_3$ to form a compound of formula (20). The compound of formula (20) (wherein $FG_1$ is nitro ($-NO_2$)) can be reduced to form a compound of formula (21), which can be coupled with a compound of formula (22) to form the compound of formula (23). Alternatively, the compound of formula (20) (wherein $FG_2$ is amino ($-NH_2$)) can be coupled with a compound of formula (22) to form compound of formula (23).

Step-2:

The compound of formula (23) can be deprotected to form a compound of formula (23a). The compound of formula (23a) can be reacted with a compound of formula (8), for example in the presence of $POCl_3$, to form a compound of formula (24), which can be coupled with a compound of formula (25) in the presence of suitable reagents such as HATU and DIPEA to form the compound of formula (I). This scheme is illustrated in Illustrations 1 and 2 below.

Illustration 1

Step-1:

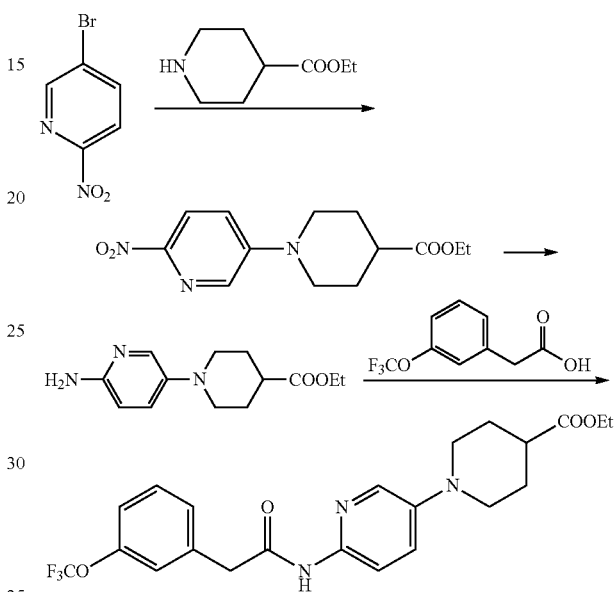

Step-2:

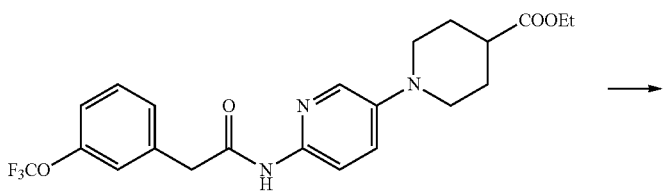

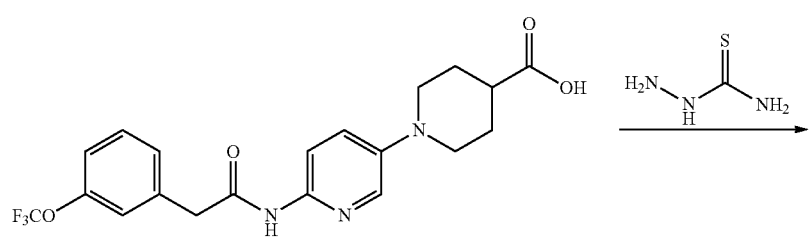

-continued
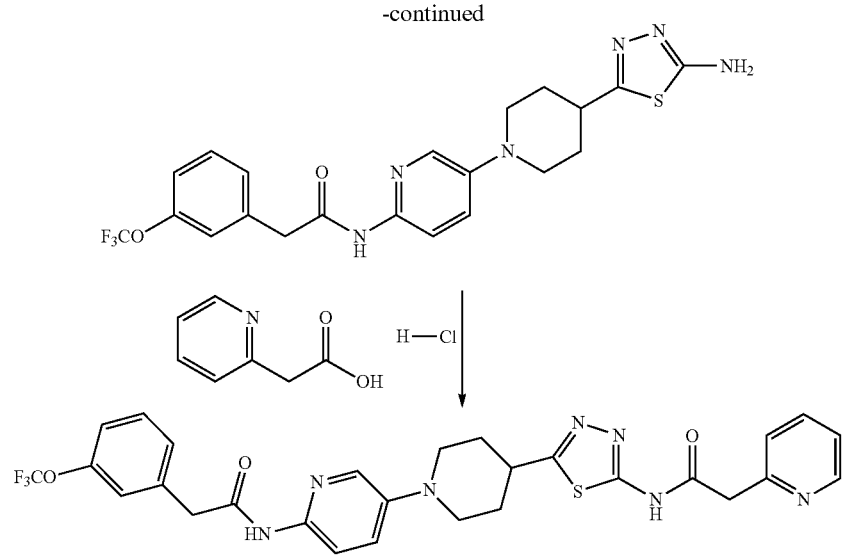
Illustration 2
Step-1:
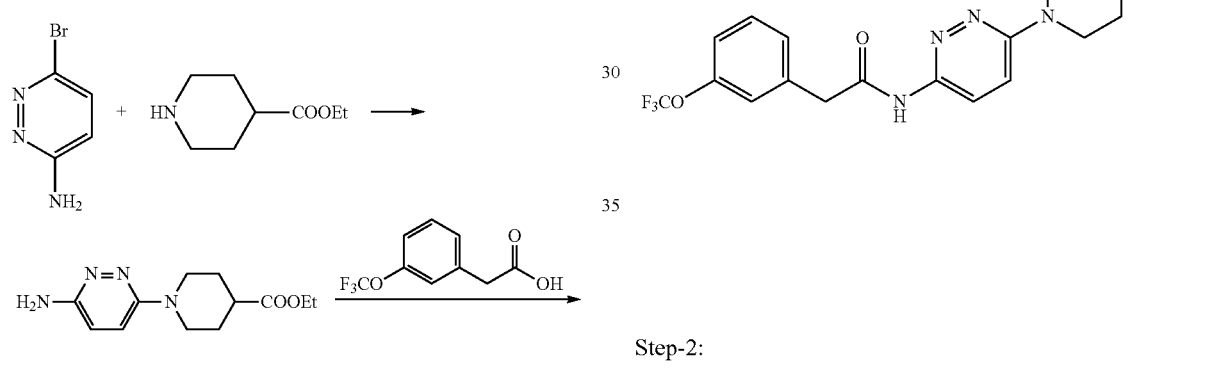
Step-2:
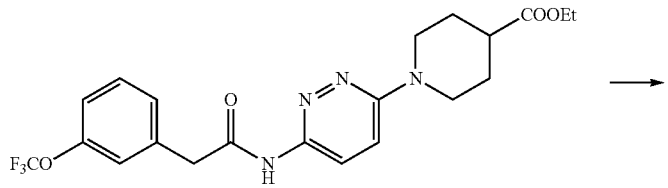
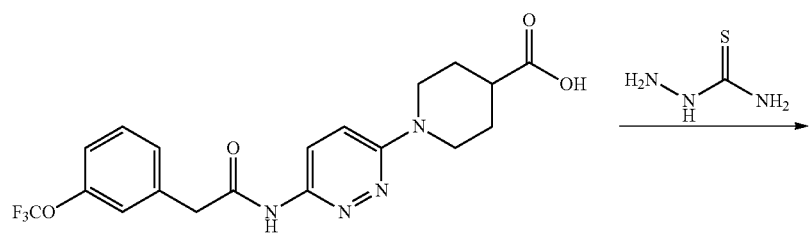

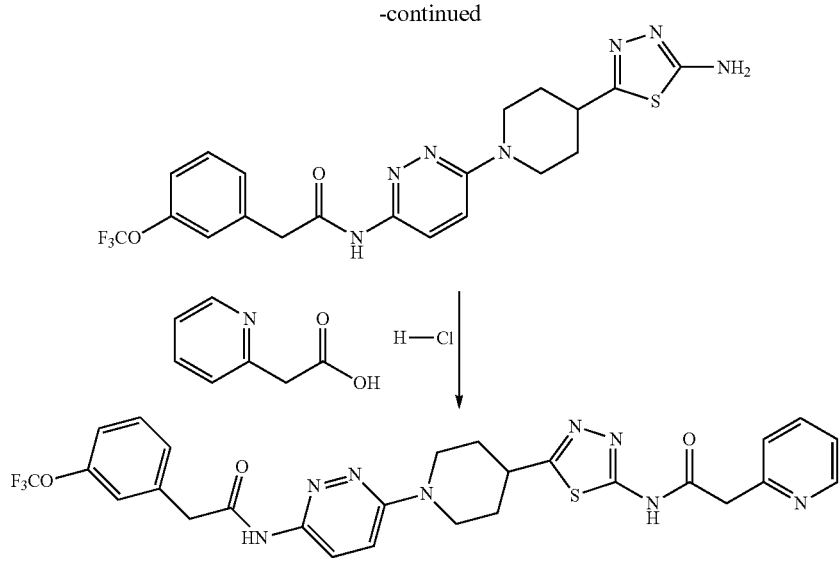

Scheme 4:

This scheme provides a method for the preparation of a compound of formula (I) wherein $R^1$ and $R^2$ are independently substituted or unsubstituted aryl or substituted or unsubstituted heteroaryl, P and Q are independently $-NR^xC(O)-(CR^xR^y)_r-$ or $-C(R^xR^y)_r-C(O)-NR^x-$, L is $-L_1-L_2-L_3-$ wherein $L_2$ is substituted or unsubstituted 3 to 14 membered heterocyclyl, $L_1$ and $L_3$ are absent or substituted or unsubstituted $C_{1-6}$ alkyl (such as methyl), A is

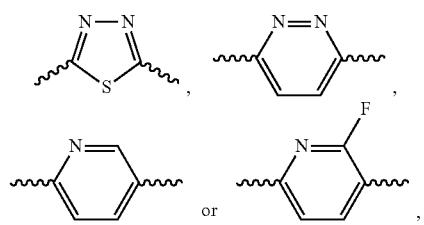

or

B is

r is 0 or 1, s is 0 or 1, v is 0 or 1 and all the other variables (including $R^x$ and $R^y$) are as described above in relation to formula (I).

Step-1:

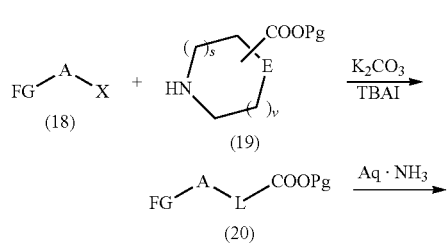

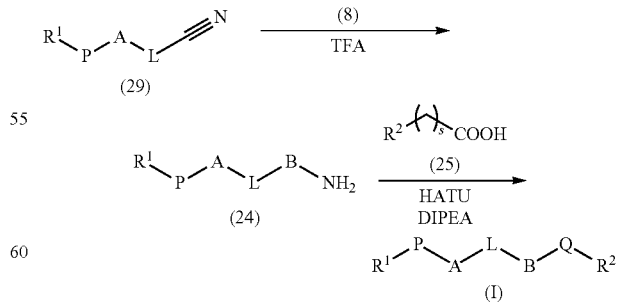

Step-2:

Step-1:

The compound of formula (18) wherein FG is nitro or amino and X is a leaving group such as bromine can be coupled with a compound of formula (19) wherein Pg is a protecting group, for example in the presence of tetrabutylammonium iodide (TBAI) and a suitable base such as K$_2$CO$_3$ to form a compound of formula (20). The compound of formula (20) can be converted using aqueous ammonia to form a compound of formula (26), which can be converted using, for example thionyl chloride, to form a compound of formula (27). The compound of formula (27) (wherein FG$_1$ is nitro (—NO$_2$)) can be reduced to form compound (28), which can be coupled with a compound of formula (22) in the presence of suitable reagents such as HATU and DIPEA to form a compound of formula (29). Alternatively, the compound of formula (27) (wherein FG$_2$ is amino (—NH$_2$)) can be coupled with a compound of formula (22) in the presence of suitable reagents such as HATU and DIPEA to form a compound of formula (29).

Step-2:

The compound of formula (29) can be reacted with a compound of formula (8) to form a compound of formula (24). The compound of formula (24) can be coupled with a compound of formula (25) in the presence of suitable reagents such as HATU and DIPEA to form the compound of formula (I). This scheme is illustrated in Illustrations 1 and 2 below.

Illustration

Step-1:

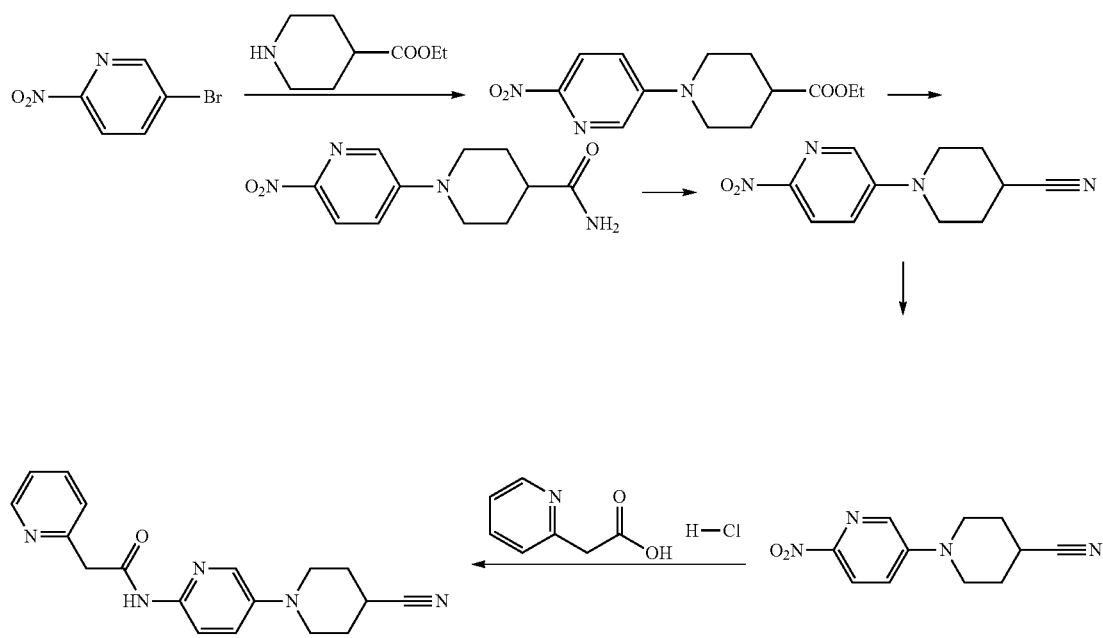

40

Step-2:

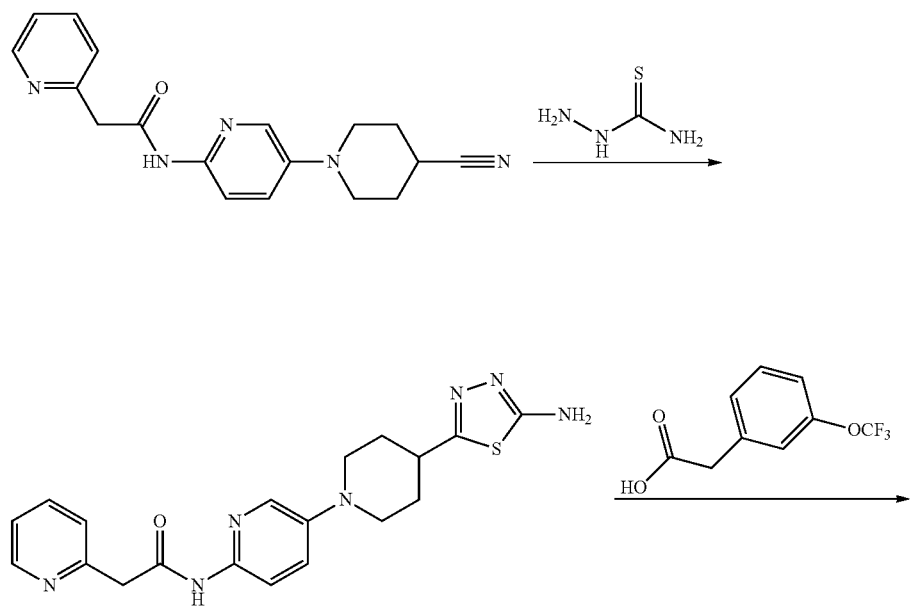

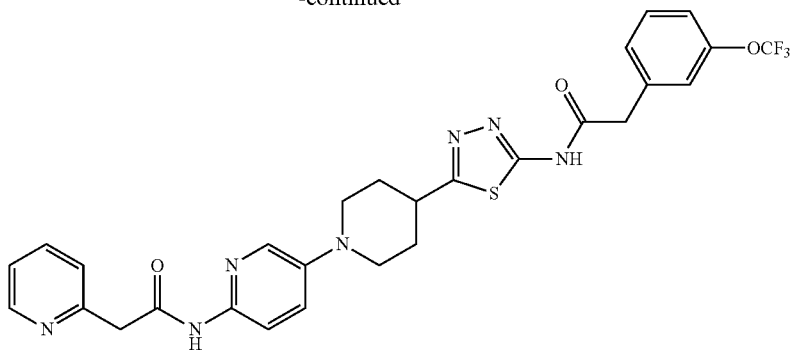

Scheme 5:

This scheme provides a method for the preparation of a compound of formula (I) wherein $R^1$ and $R^2$ are independently substituted or unsubstituted aryl or substituted or unsubstituted heteroaryl, P and Q are independently —$NR^xC(O)$—$(CR^xR^y)_r$— or —$C(R^xR^y)_r$—$C(O)$—$NR^x$—, L is -$L_1$-$L_2$-$L_3$- wherein $L_2$ is substituted or unsubstituted 3 to 14 membered heterocyclyl, $L_1$ and $L_3$ are absent or substituted or unsubstituted $C_{1-6}$ alkyl (such as methyl), A is

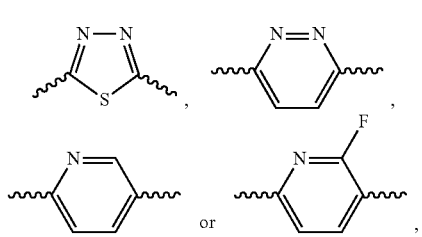

or

B is

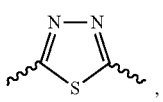

r is 0 or 1, s is 0 or 1, v is 0 or 1 and all the other variables (including $R^x$ and $R^y$) are as described above in relation to formula (I).

Step-1

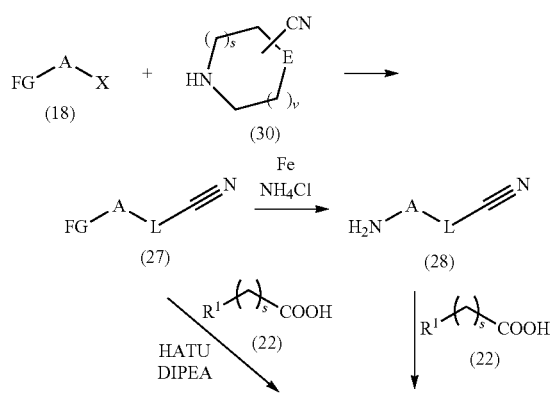

Step-2

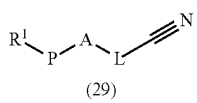

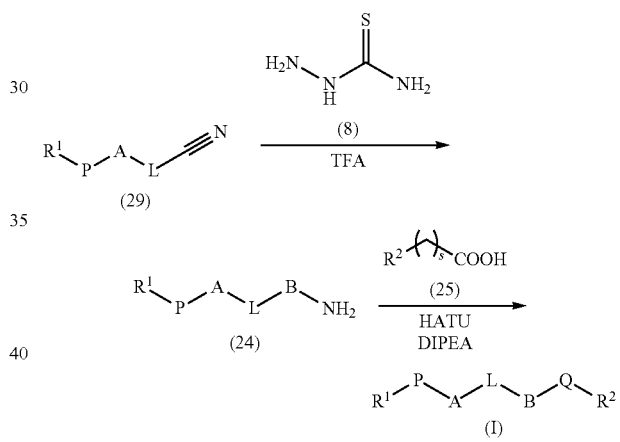

Step-1:

The compound of formula (18) wherein FG is nitro or amino and X is a leaving group such as bromine can be coupled with a compound of formula (30) to form a compound of formula (27). The compound of formula (27) (wherein $FG_1$ is nitro (—$NO_2$)) can be reduced to form compound (28), which can be coupled with a compound of formula (22) in the presence of suitable reagents such as HATU and DIPEA to form a compound of formula (29). Alternatively, a compound of formula (27) (wherein $FG_2$ is amino (—$NH_2$)) can be coupled with a compound of formula (22) in the presence of suitable reagents such as HATU and DIPEA to form a compound of formula (29).

Step-2:

The compound of formula (29) can be reacted with a compound of formula (8) to form a compound of formula (24), which can be coupled with a compound of formula (25) in the presence of suitable reagents such as HATU and DIPEA to form the compound of formula (I). This scheme is illustrated in Illustrations 1 and 2 below.

Illustration
Step-1

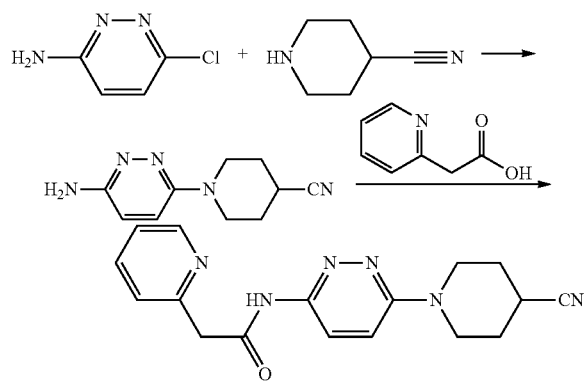

Step-2:

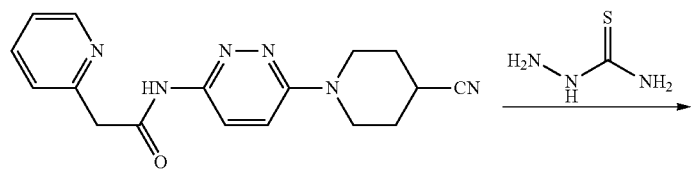

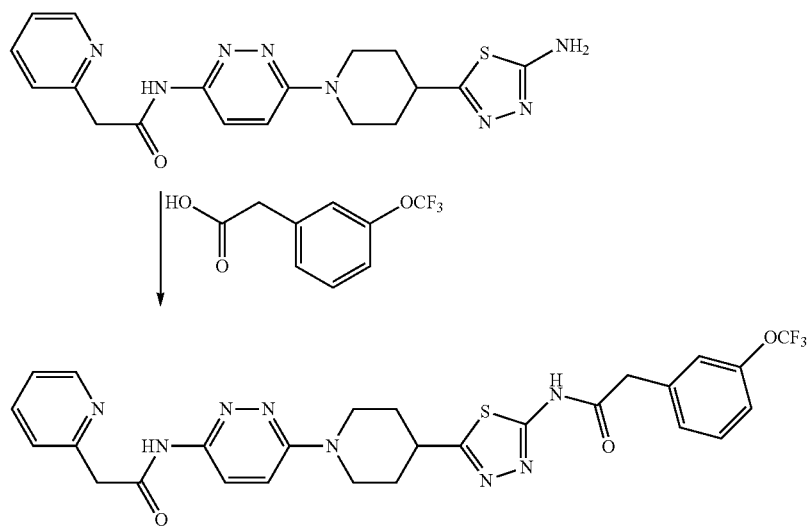

Similar methodologies with modifications known to those skilled in the art can be used to synthesize compounds of formula of (I), (II) and (III) wherein all the variables are to be understood to represent those groups described above using suitable intermediates and reagents.

EXPERIMENTAL

The examples and preparations provided below further illustrate and exemplify the compounds of the present invention and methods of preparing such compounds. It is to be understood that the scope of the present invention is not limited in any way by the scope of the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

| No. | TABLE OF INTERMEDIATES: Structure |
|---|---|
| 1 | O₂N–pyridine–N(piperidine)–COOEt |
| 2 | H₂N–pyridine–N(piperidine)–COOEt |
| 3 | F₃CO–C₆H₄–CH₂–C(O)–NH–pyridine–N(piperidine)–COOEt |
| 4 | F₃CO–C₆H₄–CH₂–C(O)–NH–pyridine–N(piperidine)–COOH |
| 5 | F₃CO–C₆H₄–CH₂–C(O)–NH–pyridine–N(piperidine)–(1,3,4-thiadiazol-2-yl)–NH₂ |
| 6 | O₂N–pyridine–N(piperidin-3-yl)–COOEt |
| 7 | H₂N–pyridine–N(piperidin-3-yl)–COOEt |
| 8 | F₃CO–C₆H₄–CH₂–C(O)–NH–pyridine–N(piperidin-3-yl)–COOEt |
| 9 | F₃CO–C₆H₄–CH₂–C(O)–NH–pyridine–N(piperidin-3-yl)–COOH |

-continued

TABLE OF INTERMEDIATES:

| No. | Structure |
|---|---|
| 10 | 2-[3-(trifluoromethoxy)phenyl]-N-[5-[3-(5-amino-1,3,4-thiadiazol-2-yl)piperidin-1-yl]pyridin-2-yl]acetamide |
| 11 | 1-(6-nitropyridin-3-yl)piperidine-4-carboxamide |
| 12 | 1-(6-nitropyridin-3-yl)piperidine-4-carbonitrile |
| 13 | 1-(6-aminopyridin-3-yl)piperidine-4-carbonitrile |
| 14 | N-[5-(4-cyanopiperidin-1-yl)pyridin-2-yl]-2-(pyridin-2-yl)acetamide |
| 15 | N-[5-[4-(5-amino-1,3,4-thiadiazol-2-yl)piperidin-1-yl]pyridin-2-yl]-2-(pyridin-2-yl)acetamide |
| 16 | 1-(6-nitropyridin-3-yl)piperidine-3-carboxamide |
| 17 | 1-(6-nitropyridin-3-yl)piperidine-3-carbonitrile |
| 18 | 1-(6-aminopyridin-3-yl)piperidine-3-carbonitrile |

-continued
TABLE OF INTERMEDIATES:
| No. | Structure |
|---|---|
| 19 | 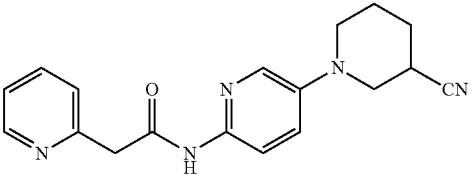 [SMILES: N#CC1CCCN(c2ccc(NC(=O)Cc3ccccn3)nc2)C1] |
| 20 | 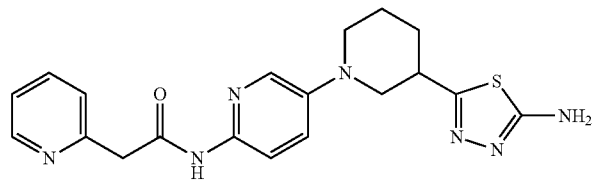 [SMILES: Nc1nnc(C2CCCN(c3ccc(NC(=O)Cc4ccccn4)nc3)C2)s1] |
| 21 | 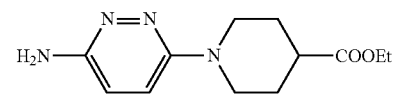 |
| 22 | 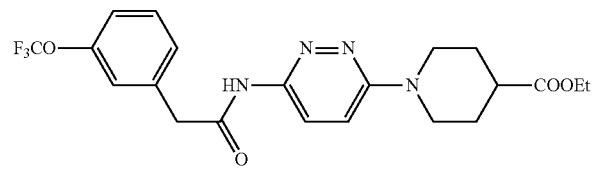 [SMILES: CCOC(=O)C1CCN(c2ccc(NC(=O)Cc3cccc(OC(F)(F)F)c3)nn2)CC1] |
| 23 | 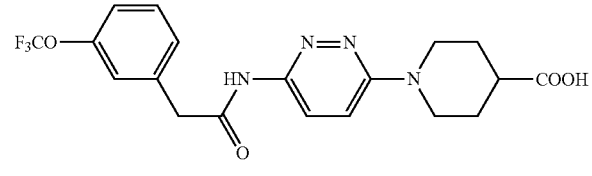 [SMILES: O=C(Cc1cccc(OC(F)(F)F)c1)Nc1ccc(N2CCC(C(=O)O)CC2)nn1] |
| 24 | 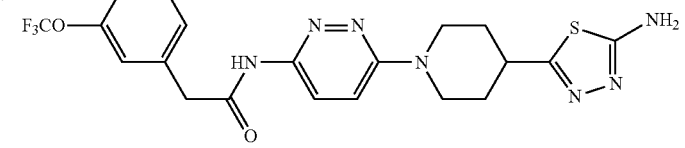 |
| 25 | 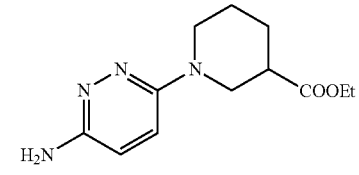 |
| 26 | 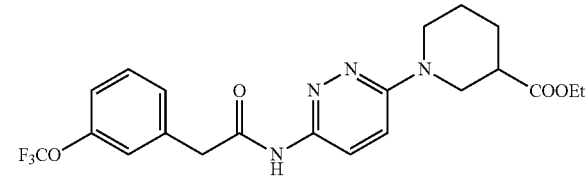 [SMILES: CCOC(=O)C1CCCN(c2ccc(NC(=O)Cc3cccc(OC(F)(F)F)c3)nn2)C1] |

TABLE OF INTERMEDIATES:

| No. | Structure |
|-----|-----------|
| 27 | 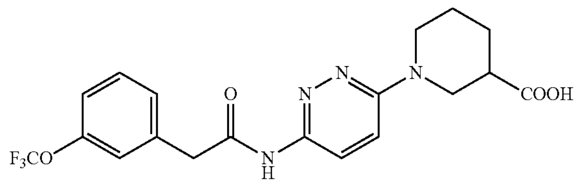 [SMILES: O=C(Cc1cccc(OC(F)(F)F)c1)Nc1ccc(N2CCCC(C(=O)O)C2)nn1] |
| 28 | 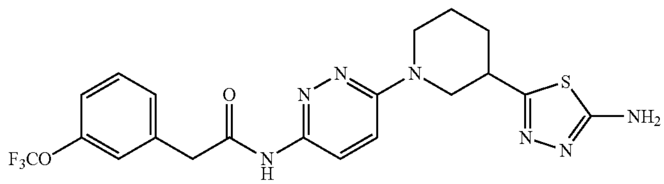 [SMILES: Nc1nnc(C2CCCN(c3ccc(NC(=O)Cc4cccc(OC(F)(F)F)c4)nn3)C2)s1] |
| 29 | 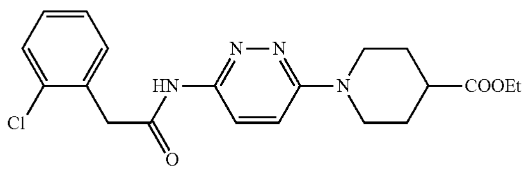 [SMILES: CCOC(=O)C1CCN(c2ccc(NC(=O)Cc3ccccc3Cl)nn2)CC1] |
| 30 | 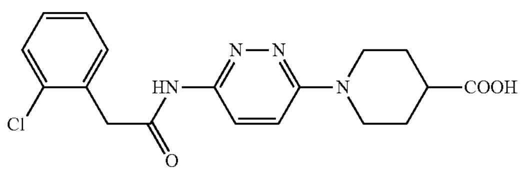 [SMILES: O=C(Cc1ccccc1Cl)Nc1ccc(N2CCC(C(=O)O)CC2)nn1] |
| 31 | 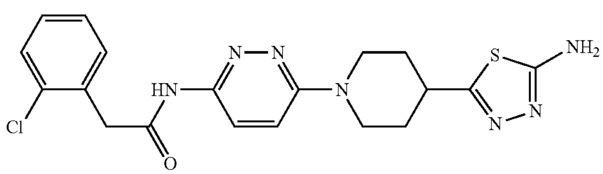 [SMILES: Nc1nnc(C2CCN(c3ccc(NC(=O)Cc4ccccc4Cl)nn3)CC2)s1] |
| 32 | 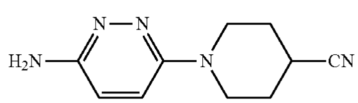 |
| 33 | 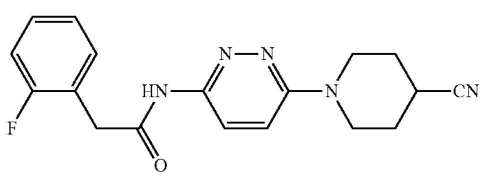 [SMILES: N#CC1CCN(c2ccc(NC(=O)Cc3ccccc3F)nn2)CC1] |
| 34 | 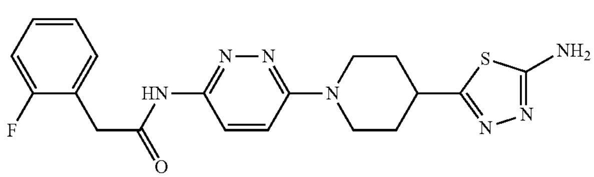 [SMILES: Nc1nnc(C2CCN(c3ccc(NC(=O)Cc4ccccc4F)nn3)CC2)s1] |
| 35 | 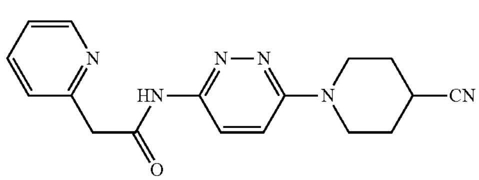 [SMILES: N#CC1CCN(c2ccc(NC(=O)Cc3ccccn3)nn2)CC1] |

TABLE OF INTERMEDIATES:

| No. | Structure |
|---|---|
| 36 | [Structure: pyridin-2-yl-CH2-C(O)-NH-pyridazine-N(piperidine)-1,3,4-thiadiazol-2-amine] |
| 37 | [Structure: pyridin-3-yl-CH2-C(O)-NH-pyridazine-N(piperidine)-CN] |
| 38 | [Structure: pyridin-3-yl-CH2-C(O)-NH-pyridazine-N(piperidine)-1,3,4-thiadiazol-2-amine] |
| 39 | [Structure: H2N-pyridazine-N(piperidine)-CH2-CN] |
| 40 | [Structure: F3CO-phenyl-CH2-C(O)-NH-pyridazine-N(piperidine)-CH2-CN] |
| 41 | [Structure: F3CO-phenyl-CH2-C(O)-NH-pyridazine-N(piperidine)-CH2-1,3,4-thiadiazol-2-amine] |

Intermediate 1: Ethyl 1-(6-nitropyridin-3-yl)piperidine-4-carboxylate

3-Bromo-6-nitropyridine (2 g, 9.85 mmol), Ethyl isonipecotate (1.7 g, 10.8 mmol), K$_2$CO$_3$ (1.36 g, 9.84 mmol) and tetrabutylammonium iodide were taken in DMSO (10 ml). This mixture was stirred at 100° C. under inert atmosphere for 16 hrs. After completion of the reaction, reaction was cooled to rt and diluted with water. Aqueous layer was extracted with EtOAc. Organic layer was dried on anhydrous Na$_2$SO$_4$. EtOAc was removed on rotavapour to obtain crude. Crude was purified on combi-flash using EtOAc and Petether (1:2) as eluent to afford the titled compound (2.2 g) as a yellow solid. $^1$H-NMR (δ ppm, DMSO-d$_6$, 400 MHz): 8.16-8.10 (m, 2H), 7.20 (dd, J 9.1, 2.8, 1H), 4.18 (q, J 7.1, 2H), 3.92-3.82 (m, 2H), 3.20-3.10 (m, 2H), 2.65-2.55 (m, 1H), 2.15-2.03 (m, 2H), 1.95-1.85 (m, 2H), 1.27 (t, J 7.1, 3H).

Intermediate 2: Ethyl 1-(6-aminopyridin-3-yl)piperidine-4-carboxylate

Intermediate 1 (2.2 g, 7.9 mmol) was dissolved in EtOH (25 ml) and H$_2$O (5 ml) mixture. To this mixture added Iron powder (2.2 g, 39.4 mmol) and NH$_4$Cl (850 mg, 15.9 mmol). This mixture was stirred at 90° C. for 16 h. After completion of the reaction, reaction mixture was filtered through celite bed. Cealite bed was washed with DCM. Filtrate was basified with aq NaHCO$_3$ solution. Aqueous layer was extracted with DCM. Combined DCM layers were dried on anhydrous Na$_2$SO$_4$. DCM was removed on rotavapour to obtain crude. Crude was purified by column on 60-120 mesh silica gel using MeOH and DCM (3:97) as eluent to afford the titled compound (1.7 g) as a brown solid. $^1$H-NMR (δ ppm, DMSO-d$_6$, 400 MHz): 7.59 (d, J 2.8, 1H), 7.13 (dd, J 8.8, 2.8, 1H), 6.38 (d, J 8.8, 1H), 5.32 (bs, 2H), 4.07 (q, J 7.1, 2H), 3.31-3.25 (m, 2H), 2.63-2.55 (m, 2H), 2.45-2.33 (m, 1H), 1.87 (d, J 12.6, 2H), 1.73-1.62 (m, 2H), 1.18 (t, J 7.1, 3H).

Intermediate 3: Ethyl 1-(6-(2-(3-(trifluoromethoxy)phenyl)acetamido)pyridin-3-yl)piperidine-4-carboxylate Intermediate 2 (1.0 g, 3.8 mmol), 3-(Trifluoromethoxy)phenylacetic acid (1.03 g, 4.7 mmol), HATU (1.82 g, 4.7 mmol), DIPEA (1.1 ml, 8.5 mmol) were taken in DMF (6 ml). This mixture was stirred at rt under inert atmosphere for 12 h. Reaction mass was diluted with water to obtain a solid. Solid was filtered and dried to obtain the titled compound as a grey solid. $^1$H-NMR (δ ppm, DMSO-d$_6$, 400 MHz): 10.43 (s, 1H), 7.99 (d, J 2.7, 1H), 7.86 (d, J 9, 1H), 7.47-7.41 (m, 1H), 7.39-7.31 (m, 3H), 7.22 (d, J 8, 1H), 4.07 (q, J 7.1, 2H), 3.73 (s, 2H), 3.56 (d, J 12.2, 2H), 2.75 (t, J 11.4, 2H), 2.50-2.41 (m, 1H), 1.90 (d, J 11.1, 2H), 1.72-1.60 (m, 2H), 1.18 (t, J 7, 3H).

Intermediate 4: 1-(6-(2-(3-(Trifluoromethoxy)phenyl)acetamido)pyridin-3-yl)piperidine-4-carboxylic acid Intermediate 3 (1.59 g, 3.5 mmol) was dissolved in MeOH and water. To this mixture added NaOH (590 mg, 14.7 mmol). This mixture was stirred at rt for 1 h. MeOH was removed on rotavapour and residue was acidified with 2N HCl up to pH-5. Above aqueous layer was extracted with MeOH and DCM (1:9) mixture. Organic layer was dried on anhydrous Na$_2$SO$_4$ and evaporated on rotavapour to obtain crude. Crude was triturated with Et$_2$O to obtain the titled compound as a brown solid (1.19 g). $^1$H-NMR (δ ppm, DMSO-d$_6$, 400 MHz): 12.14 (bs, 1H), 10.43 (s, 1H), 7.99 (s, 1H), 7.86 (d, J 7.9, 1H), 7.49-7.41 (m, 1H), 7.29-7.30 (m, 3H), 7.22 (d, J 8.2, 1H), 3.73 (s, 2H), 3.56 (d, J 11.8, 2H), 2.74 (t, J 11.1, 2H), 2.41-2.33 (m, 1H), 1.93-1.85 (m, 2H), 1.70-1.58 (m, 2H).

Intermediate 5: N-(5-(4-(5-amino-1,3,4-thiadiazol-2-yl)piperidin-1-yl)pyridin-2-yl)-2-(3-(trifluoromethoxy)phenyl)acetamide Intermediate 4 (290 mg, 0.45 mmol), Thiosemicarbazide (230 mg) and POCl$_3$ (12 ml) were mixed and heated to 90° C. for 16 h. After completion of reaction, reaction mass was cooled to rt and quenched into crushed ice (150 g). The resulting mixture was basified to pH 14 with saturated aq. NaOH. Aqueous layer was extracted with DCM and MeOH (9:1) mixture. Organic layer was dried on anhydrous Na$_2$SO$_4$ and evaporated on rotavapour to obtain crude (110 mg). Crude was used in the next step without further purification. $^1$H-NMR (δ ppm, DMSO-d$_6$, 400 MHz): 10.44 (s, 1H), 8.03 (s, 1H), 7.88 (d, J 9, 1H), 7.48-7.30 (m, 4H), 7.22 (d, J 7.8, 1H), 6.97 (s, 2H), 3.73 (s, 2H), 3.63 (d, 12.4, 2H), 3.19-3.09 (m, 1H), 2.88 (t, J 10.9, 2H), 2.8 (d, 13.3, 2H), 1.90-1.78 (m, 2H).

Intermediate 6: Ethyl 1-(6-nitropyridin-3-yl)piperidine-3-carboxylate

3-Bromo-6-nitropyridine (2 g, 9.85 mmol), Ethyl nipecotate (1.7 g, 10.8 mmol), K$_2$CO$_3$ (1.36 g, 9.84 mmol) and tetrabutylammonium iodide (360 mg, 0.98 mmol) were taken in DMSO (10 ml). This mixture was stirred at 100° C. under inert atmosphere for 16 hrs. After completion of the reaction, reaction was cooled to rt and diluted with water. Aqueous layer was extracted with EtOAc. Organic layer was dried on anhydrous Na$_2$SO$_4$. EtOAc was removed on rotavapour to obtain crude. Crude was purified on combi-flash using EtOAc and Petether (1:2) as eluent to afford the titled compound (2.3 g) as a yellow solid.

Intermediate 7: Ethyl 1-(6-aminopyridin-3-yl)piperidine-3-carboxylate

Intermediate 6 (2.2 g, 7.9 mmol) was dissolved in EtOH (25 ml) and H$_2$O (5 ml) mixture. To this mixture added Iron powder (2.2 g, 39.4 mmol) and NH$_4$Cl (850 mg, 15.9 mmol). This mixture was stirred at 90° C. for 16 h. After completion of the reaction, reaction mixture was filtered through celite bed. Cealite bed was washed with DCM. Filtrate was basified with aq NaHCO$_3$ solution. Aqueous layer was extracted with DCM. Combined DCM layers were dried on anhydrous Na$_2$SO$_4$. DCM was removed on rotavapour to obtain crude. Crude was purified by combi-flash using MeOH and DCM (4:96) as eluent to afford the titled compound (1.8 g) as a brown liquid. $^1$H-NMR (δ ppm, DMSO-d$_6$, 400 MHz): 7.60 (d, J 2.8, 1H), 7.13 (dd, J 8.8, 2.9, 1H), 6.38 (dd, J 8.8, 3, 1H), 5.35 (bs, 2H), 4.10 (q, J 6.8, 2H), 3.30-3.20 (m, 1H), 3.11-3.04 (m, 1H), 2.84-2.76 (m, 1H), 2.69-2.58 (m, 2H), 1.88-1.81 (m, 1H), 1.75-1.68 (m, 1H), 1.60-1.50 (m, 2H), 1.18 (t, J 7.1, 3H).

Intermediate 8: ethyl 1-(6-(2-(3-(trifluoromethoxy)phenyl)acetamido)pyridin-3-yl)piperidine-3-carboxylate Intermediate 7 (1.8 g, 7.2 mmol), 3-(Trifluoromethoxy)phenylacetic acid (1.9 g, 8.63 mmol), HATU (3.3 g, 8.7 mmol), DIPEA (3.8 ml, 21.6 mmol) were taken in DMF (5 ml). This mixture was stirred at rt under inert atmosphere for 12 h. Reaction mass was diluted with water and extracted with DCM. DCM layer was dried on anhydrous Na$_2$SO$_4$. DCM was removed on rotavapour to obtain the titled compound (3.2 g) which was used in the next step without further purification. $^1$H-NMR (δ ppm, DMSO-d$_6$, 400 MHz): 10.45 (s, 1H), 7.99 (d, J 2.6, 1H), 7.87 (d, J 9, 1H), 7.48-7.41 (m, 1H), 7.39-7.30 (m, 3H), 7.22 (d, J 8, 1H), 4.08 (q, J 7.1, 2H), 3.73 (s, 2H), 3.60-3.53 (m, 1H), 3.41-3.33 (m, 1H), 3.05-2.96 (m, 1H), 2.86-2.78 (m, 1H), 2.70-2.50 (m, 1H), 1.95-1.85 (m, 1H), 1.78-1.68 (m, 1H), 1.63-1.54 (m, 2H), 1.18 (t, J 7.1, 3H). MS (m/z): 452.6 [M+H]$^+$.

Intermediate 9: 1-(6-(2-(3-(trifluoromethoxy)phenyl)acetamido)pyridin-3-yl)piperidine-3-carboxylic acid Intermediate 8 (1.6 g, 3.5 mmol) was dissolved in MeOH and water. To this mixture added NaOH (430 mg, 10.5 mmol). This mixture was stirred at rt for 30 mins. MeOH was removed on rotavapour and residue was acidified with 2N HCl up to pH-5. After that above aqueous layer was extracted with MeOH and DCM (2:8) mixture. Organic layer was dried on anhydrous Na$_2$SO$_4$ and evaporated on rotavapour to obtain crude. Crude was triturated with Et$_2$O to obtain the titled compound as a brown solid (950 mg). $^1$H-NMR (δ ppm, DMSO-d$_6$, 400 MHz): 12.25 (s, 1H), 10.44 (s, 1H), 7.99 (d, J 2.7, 1H), 7.87 (d, J 8.8, 1H), 7.47-7.41 (m, 1H), 7.38-7.31 (m, 3H), 7.22 (d, J 7.2, 1H), 3.73 (s, 2H), 3.58 (d, J 12.4, 1H), 3.40 (d, J 11.4, 1H), 3.07-2.90 (m, 1H), 2.82-2.73 (m, 1H), 2.60-2.50 (m, 1H), 1.95-1.83 (m, 1H), 1.75-1.68 (m, 1H), 1.60-1.50 (m, 2H).

Intermediate 10: N-(5-(3-(5-amino-1,3,4-thiadiazol-2-yl)piperidin-1-yl)pyridin-2-yl)-2-(3-(trifluoromethoxy)phenyl)acetamide Intermediate 9 (950 mg, 2.24 mmol), Thiosemicarbazide (610 mg, 6.7 mmol) and $POCl_3$ (10 ml) were mixed and heated to 90° C. for 16 h. After completion of reaction, reaction mass was cooled to rt and quenched into crushed ice (150 g). The resulting mixture was basified to pH 14 with saturated aq. NaOH. Aqueous layer was extracted with DCM and MeOH (9:1) mixture. Organic layer was dried on anhydrous $Na_2SO_4$ and evaporated on rotavapour to obtain crude. Crude was triturated with EtOAc and Petether (1:1) mixture to obtain the titled compound (1 g) as a brown solid. MS (m/z): 479.4 [M+H]$^+$.

Intermediate 11: 1-(6-nitropyridin-3-yl)piperidine-4-carboxamide

Intermediate 1 (7.8 g, 27.9 mmol) was dissolved in MeOH (39 ml) and added aq ammonia (46.8 ml. This mixture was heated to 50° C. for 12 h. Solid that formed in the reaction mixture was filtered and dried under vacuum to obtain the titled compound (1.7 g) as a yellow solid. $^1$H-NMR (δ ppm, DMSO-$d_6$, 400 MHz): 8.23 (d, J 2.9, 1H), 8.11 (d, J 9.2, 1H), 7.45 (dd, J 3, 9.2, 1 H), 7.25 (bs, 1H), 6.74 (bs, 1H), 4.06 (d, J 12.3, 2H), 3.10-3.00 (m, 2H), 2.45-2.35 (m, 1H), 1.81 (d, J 10.8, 2H), 1.65-1.51 (m, 2H). MS (m/z): 250.9 [M+H]$^+$.

Intermediate 12: 1-(6-nitropyridin-3-yl)piperidine-4-carbonitrile

Intermediate 11 (1.7 g 6.79 mmol) was dissolved in Chloroform (25 ml) and added TEA (4.8 ml, 34 mmol). This mixture was cooled to −5° C. and added trifluoroacetic anhydride (2.23 ml, 17 mmol) drop-wise. Above mixture was stirred for 1 h at rt under $N_2$ atmosphere. Reaction mass was diluted with water and organic layer was separated. Organic layer dried on anhydrous $Na_2SO_4$. Organic layer was distilled on rotavapour to obtain the titled compound (1.36 g) as a yellow solid. It was used in the next step without further purification. $^1$H-NMR (δ ppm, DMSO-$d_6$, 400 MHz): 8.25 (d, J 3, 1H), 8.13 (d, J 9.2, 1H), 7.48 (dd, J 3, 9.2, 1H), 3.80-3.70 (m, 2H), 3.42-3.33 (m, 2H), 3.20-3.11 (m, 1H), 2.05-1.96 (m, 2H), 1.85-1.75 (m, 2H).

Intermediate 13: 1-(6-aminopyridin-3-yl)piperidine-4-carbonitrile

Intermediate 12 (1.36 g, 5.85 mmol) was dissolved in EtOH (40 ml) and $H_2O$ (8 ml) mixture. To this mixture added Iron powder (1.63 g, 29.3 mmol) and $NH_4Cl$ (624 mg, 11.7 mmol). This mixture was stirred at 90° C. for 16 h. After completion of the reaction, reaction mixture was filtered through celite bed. Cealite bed was washed with DCM. Filtrate was basified with aq $NaHCO_3$ solution. Aqueous layer was extracted with DCM. Combined DCM layers were dried on anhydrous $Na_2SO_4$. DCM was removed on rotavapour to obtain crude. Crude was triturated with $Et_2O$ to obtain the titled compound (1 g) as a brown solid. $^1$H-NMR (δ ppm, DMSO-$d_6$, 400 MHz): 7.61 (d, J 2.6, 1H), 7.15 (dd, J 3, 8.8, 1H), 6.39 (d, J 8.8, 1H), 5.38 (bs, 2H), 3.10-3.03 (m, 2H), 2.99-2.91 (m, 1H), 2.86-2.78 (m, 2H), 2.00-1.93 (m, 2H), 1.85-1.75 (m, 2H).

Intermediate 14: N-(5-(4-cyanopiperidin-1-yl)pyridin-2-yl)-2-(pyridin-2-yl)acetamide Intermediate 13 (440 mg, 2.29 mmol), 2-Pyridylacetic acid hydrochloride (453 mg, 2.6 mmol), HATU (992 mg, 2.6 mmol), DIPEA (1.1 ml, 6.5 mmol) were taken in DMF (3 ml). This mixture was stirred at rt under inert atmosphere for 12 h. Reaction mass was diluted with water and filtered the solid that formed. Solid was washed with water and dried on high vacuum to obtain the titled compound as an Off-white solid (320 mg). $^1$H-NMR (δ ppm, DMSO-$d_6$, 400 MHz): 10.42 (s, 1H), 8.49 (d, J 4.3, 1H), 8.01 (d, J 1.8, 1H), 7.89 (d, J 9, 1H), 7.73 ((t, J 7.5, 1H), 7.41-7.35 (m, 2H), 7.27-7.21 (m, 1H), 3.87 (s, 2H), 3.35-3.28 (m, 2H), 3.07-2.98 (m, 3H), 2.03-1.94 (m, 2H), 1.86-1.77 (m, 2H).

Intermediate 15: N-(5-(4-(5-amino-1,3,4-thiadiazol-2-yl)piperidin-1-yl)pyridin-2-yl)-2-(pyridin-2-yl)acetamide Intermediate 14 (320 mg, 0.894 mmol), Thiosemicarbazide (162 mg, 1.79 mmol) and trifluoroacetic acid (2 ml) were mixed and heated to 90° C. for 2 h. After 2 h, reaction mixture was cooled to rt and basified to pH 14 to obtain a solid. Solid was triturated with $Et_2O$ to obtain the titled compound (300 mg) as a brown solid. $^1$H-NMR (δ ppm, DMSO-$d_6$, 400 MHz): 10.39 (s, 1H), 8.49 (d, J 3.2, 1H), 8.02 (d, J 2.2, 1H), 7.89 (d, J 8.7, 1H), 7.73 (t, J 7.8, 1H), 7.41-7.35 (m, 2H), 7.28-7.22 (m, 1H), 6.96 (bs, 2H), 3.87 (s, 2H), 3.67 (d, J 12.1, 2H), 3.07-2.98 (m, 1H), 2.80 (t, J 11.9, 2H), 2.03 (d, J 11.3, 2H), 1.82-1.70 (m, 2H).

Intermediate 16: 1-(6-nitropyridin-3-yl)piperidine-3-carboxamide

Intermediate 6 (5 g, 17.9 mmol) was dissolved in MeOH (25 ml) and added aq ammonia (30 ml). This mixture was heated to 50° C. for 12 h. Solid that formed in the reaction mixture was filtered and dried under vacuum to obtain the titled compound (1.4 g) as a yellow solid. $^1$H-NMR (δ ppm, DMSO-$d_6$, 400 MHz): 8.24 (d, J 2.7, 1H), 8.10 (d, J 9.2, 1H), 7.46 (dd, J 2.9, 9.2, 1H), 7.35 (bs, 1H), 6.85 (bs, 1H), 4.09-3.95 (m, 2H), 3.13 (t, J 11, 1H), 3.03 (t, J 10, 1H), 2.45-2.35 (m, 1H), 1.93-1.85 (m, 1H), 1.79-1.61 (m, 2H), 1.55-1.42 (m, 1H). MS (m/z): 251.0 [M+H]$^+$

Intermediate 17: 1-(6-nitropyridin-3-yl)piperidine-3-carbonitrile

Intermediate 16 (1.4 g 5.6 mmol) was dissolved in Chloroform (20 ml) and added TEA (3.9 ml, 28 mmol). This mixture was cooled to −5° C. and added trifluoroacetic anhydride (1.95 ml, 14 mmol) drop-wise. Above mixture was stirred for 1 h at rt under $N_2$ atmosphere. Reaction mass was diluted with water and organic layer was separated. Organic layer dried on anhydrous $Na_2SO_4$. Organic layer was distilled on rotavapour to obtain the titled compound (1 g) as a yellow solid. It was used in the next step without further purification. $^1$H-NMR (δ ppm, DMSO-$d_6$, 400 MHz): 8.30 (d, J 2.9, 1H), 8.13 (d, J 9.2, 1H), 7.54 (dd, J 3, 9.2, 1H), 3.88-3.75 (m, 2H), 3.62-3.45 (m, 2H), 3.17-3.09 (m, 1H), 2.01-1.75 (m, 2H), 1.70-1.58 (m, 2H). MS (m/z): 232.9 [M+H]$^+$.

Intermediate 18: 1-(6-aminopyridin-3-yl)piperidine-3-carbonitrile

Intermediate 17 (1 g, 4.3 mmol) was dissolved in EtOH (30 ml) and H$_2$O (6 ml) mixture. To this mixture added Iron powder (1.20 g, 21.5 mmol) and NH$_4$Cl (460 mg, 8.7 mmol). This mixture was stirred at 90° C. for 16 h. After completion of the reaction, reaction mixture was filtered through celite bed. Cealite bed was washed with DCM. Filtrate was basified with aq NaHCO$_3$ solution. Aqueous layer was extracted with DCM. Combined DCM layers were dried on anhydrous Na$_2$SO$_4$. DCM was removed on rotavapour to obtain crude. Crude was purified by combi-flash using MeOH and DCM (3:97) as eluent to afford the titled compound (880 mg) as a black gel.

Intermediate 19: N-(5-(3-cyanopiperidin-1-yl)pyridin-2-yl)-2-(pyridin-2-yl)acetamide Intermediate 18 (440 mg, 2.2 mmol), 2-Pyridylacetic acid hydrochloride (453 mg, 2.6 mmol), HATU (992 mg, 2.6 mmol), DIPEA (1.1 ml, 6.5 mmol) were taken in DMF (3 ml). This mixture was stirred at rt under inert atmosphere for 12 h. Reaction mass was diluted with water and extracted with DCM. DCM was dried on anhydrous Na$_2$SO$_4$ and DCM was removed on rotavapour to obtain crude. Crude was purified by combi-flash using MeOH and DCM (3:97) as eluent to afford the titled compound (450 mg) as a brown solid. $^1$H-NMR (δ ppm, DMSO-d$_6$, 400 MHz): 10.45 (s, 1H), 8.49 (d, J 4, 1H), 8.03 (d, J 2.5, 1H), 7.90 (d, J 8.4, 1H), 7.73 (t, J 6.3, 1H), 7.44-7.33 (m, 2H), 7.27-7.21 (m, 1H), 3.87 (s, 2H), 3.40-3.31 (m, 2H), 3.20-3.04 (m, 3H), 1.90-1.71 (m, 3H), 1.70-1.59 (m, 1H). MS (m/z): 322.0 [M+H]$^+$.

Intermediate 20: N-(5-(3-(5-amino-1,3,4-thiadiazol-2-yl)piperidin-1-yl)pyridin-2-yl)-2-(pyridin-2-yl)acetamide Intermediate 19 (425 mg, 1.87 mmol), Thiosemicarbazide (216 mg, 2.37 mmol) and trifluoroacetic acid (2 ml) were mixed and heated to 90° C. for 2 h. After 2 h, reaction mixture was cooled to rt and basified to pH 14. Aqueous layer was extracted with MeOH and DCM (1:9) mixture. Organic layer was dried on anhydrous Na$_2$SO$_4$ and removed MeOH and DCM on rotavapour to obtain crude. Crude was purified by combi-flash using MeOH and DCM (7:93) as eluent to afford the titled compound (164 mg) as a pink solid. MS (m/z): 396.1 [M+H]$^+$.

Intermediate 21: Ethyl 1-(6-aminopyridazin-3-yl)piperidine-4-carboxylate

3-Amino-6-chloropyridazine (1 g, 7.72 mmol) and Ethyl isonipecotate (2.4 g, 15.39 mmol) were mixed and heated to 180° C. for 6 h. After 6 h, reaction mass cooled to rt and added satd. Aqueous NaHCO$_3$ solution (50 ml). This mixture was extracted with DCM. DCM removed on rotavapour to obtain crude. Crude was purified by combi-flash using MeOH and DCM (3:97) as eluent to afford the titled compound as a brown solid (1.5 g).

Intermediate 22: Ethyl 1-(6-(2-(3-(trifluoromethoxy)phenyl)acetamido)pyridazin-3-yl)piperidine-4-carboxylate Intermediate 21 (1.5 g, 5.99 mmol), 3-(Trifluoromethoxy)phenylacetic acid (1.58 g, 7.17 mmol), HATU (5 g, 13.14 mmol), DIPEA (3.1 ml, 17.78 mmol) were taken in DMF (4 ml). This mixture was stirred at rt under inert atmosphere for 12 h. Reaction mass was diluted with water and extracted with DCM. DCM layer was dried on anhydrous Na$_2$SO$_4$ and DCM removed on rotavapour to obtain crude. Crude was purified by combi-flash using MeOH and DCM (1:99) as eluent to afford the titled compound as a brown gummy solid (1.1 g). $^1$H-NMR (δ ppm, DMSO-d$_6$, 400 MHz): 10.93 (s, 1H), 7.98 (d, J 9.8, 1H), 7.48-7.42 (m, 1H), 7.38-7.30 (m, 3H), 7.24 (d, J 8, 1H), 4.15 (d, J 13.3, 2H), 4.06 (q, J 7.1, 2H), 3.78 (s, 2H), 2.98 (t, J 11.4, 2H), 2.63-2.55 (m, 1H), 1.89 (d, J 10.6, 2H), 1.62-1.50 (m, 2H), 1.17 (t, J 7.1, 3H).

Intermediate 23: 1-(6-(2-(3-(trifluoromethoxy)phenyl)acetamido)pyridazin-3-yl) piperidine-4-carboxylic acid Intermediate 22 (1.1 g, 2.43 mmol) was dissolved in MeOH and water. To this mixture added NaOH (290 mg, 7.25 mmol). This mixture was stirred at rt for 16 h. Reaction mass was acidified with dil. HCl up to pH~5 to obtain a solid. Solid was filtered and dried to obtain the titled compound as a yellow solid (450 mg). $^1$H-NMR (δ ppm, DMSO-d$_6$, 400 MHz): 12.27 (bs, 1H), 10.92 (s, 1H), 7.97 (d, J 9.8, 1H), 7.47-7.42 (m, 1H), 7.37-7.29 (m, 3H), 7.28-7.20 (m, 1H), 4.14 (d, J 13.2, 2H), 3.78 (s, 2H), 3.40-3.30 (m, 1H), 3.01-2.93 (m, 2H), 1.87 (d, J 10.6, 2H), 1.60-1.49 (m, 2H). MS (m/z): 425.0 [M+H]$^+$.

Intermediate 24: N-(6-(4-(5-amino-1,3,4-thiadiazol-2-yl)piperidin-1-yl)pyridazin-3-yl)-2-(3-(trifluoromethoxy)phenyl)acetamide Intermediate 23 (510 mg, 1.20 mmol), Thiosemicarbazide (330 mg, 3.6 mmol) and POCl$_3$ (5 ml) were mixed and heated to 90° C. for 3 h. After completion of reaction, reaction mass was cooled to rt and quenched into crushed ice (150 g). The resulting mixture was basified to pH 10 with saturated aq. NaOH. Aqueous layer was extracted with DCM and MeOH (9:1) mixture. Organic layer was dried on anhydrous Na$_2$SO$_4$ and evaporated on rotavapour to obtain crude. Crude was purified by combi-flash using MeOH and DCM (6:94) as eluent to afford the titled compound as a pale-yellow solid (100 mg). $^1$H-NMR (δ ppm, DMSO-d$_6$, 400 MHz): 10.93 (s, 1H), 7.98 (d, J 9.8, 1H), 7.48-7.42 (m, 1H), 7.37-7.32 (m, 3H), 7.24 (d, J 8, 1H), 7.00 (s, 2H), 4.27 (d, J 13.3, 2H), 3.78 (s, 2H), 3.20-3.10 (m, 1H), 3.01 (t, J 11.6, 2H), 2.02 (d, J 10.8, 2H), 1.70-1.58 (m, 2H). MS (m/z): 479.8 [M+H]$^+$.

Intermediate 25: ethyl 1-(6-aminopyridazin-3-yl)piperidine-3-carboxylate

3-Amino-6-chloropyridazine (3 g, 23.2 mmol) and Ethyl nipecotate (7.3 g, 46.4) mmol were mixed and heated to 180° C. for 6 h. After 6 h, reaction mass cooled to rt and added satd. Aqueous NaHCO$_3$ solution (50 ml). This mixture was extracted with DCM. DCM removed on rotavapour to obtain crude. Crude was purified by column chromatography on 60-120 mesh silica gel using MeOH and DCM (3:97) as eluent to afford the titled compound as a brown gummy solid (2.9 g). MS (m/z): 250.8 [M+H]$^+$.

Intermediate 26: Ethyl 1-(6-(2-(3-(trifluoromethoxy)phenyl)acetamido)pyridazin-3-yl)piperidine-3-carboxylate Intermediate 25 (2.9 g, 11.6 mmol), 3-(Trifluoromethoxy)phenylacetic acid (3.06 g, 13.9 mmol), HATU (9.7 g, 25.5 mmol), DIPEA (2 ml, 34.75 mmol) were taken in DMF (6 ml). This mixture was stirred at rt under inert atmosphere for 12 h. Reaction mass was diluted with water and extracted with DCM. DCM layer was dried on anhydrous $Na_2SO_4$ and DCM removed on rotavapour to obtain crude. Crude was purified by column chromatography on 60-120 mesh silica gel using MeOH and DCM (1:99) as eluent to afford the titled compound as a brown solid (3.1 g). $^1$H-NMR (δ ppm, DMSO-$d_6$, 400 MHz): 10.91 (s, 1H), 7.97 (d, J 9.8, 1H), 7.47-7.43 (m, 1H), 7.37-7.31 (m, 3H), 7.24 (d, J 8, 1H), 4.25 (d, J 13, 1H), 4.06 (q, J 7, 2H), 3.90 (d, J 12.9, 1H), 3.78 (s, 2H), 3.21-3.05 (m, 2H), 2.60-2.51 (m, 1H), 2.00-1.91 (m, 1H), 1.72-1.53 (m, 2H), 1.52-1.41 (m, 1H), 1.17 (t, J 7.1, 3H).

Intermediate 27: 1-(6-(2-(3-(Trifluoromethoxy)phenyl)acetamido)pyridazin-3-yl) piperidine-3-carboxylic acid Intermediate 26 (3.1 g, 6.85 mmol) was dissolved in MeOH and water. To this mixture added NaOH (1.64 g, 41.1 mmol). This mixture was stirred at rt for 3 h. Reaction mass was acidified with dil. HCl up to pH~5 to obtain a solid. Solid was filtered and dried to obtain the titled compound as a yellow solid (1.4 g). $^1$H-NMR (δ ppm, DMSO-$d_6$, 400 MHz): MS (m/z): 425.0 [M+H]$^+$. 12.33 (bs, 1H), 10.92 (s, 1H), 7.97 (d, J 9.7, 1H), 7.48-7.42 (m, 1H), 7.38-7.31 (m, 3H), 7.24 (d, J 7.6, 1H), 4.25 (d, J 11.3, 1H), 3.95 (d, J 13.3, 1H), 3.78 (s, 2H), 3.15-3.00 (m, 2H), 2.00-1.90 (m, 1H), 1.75-1.60 (m, 2H), 1.55-1.40 (m, 1H). MS (m/z): 425.0 [M+H]$^+$.

Intermediate 28: N-(6-(3-(5-amino-1,3,4-thiadiazol-2-yl)piperidin-1-yl)pyridazin-3-yl)-2-(3-(trifluoromethoxy)phenyl)acetamide Intermediate 27 (1.4 g, 3.3 mmol), Thiosemicarbazide (900 mg, 9.9 mmol) and $POCl_3$ (14 ml) were mixed and heated to 90° C. for 3 h. After completion of reaction, reaction mass was cooled to rt and quenched into crushed ice. The resulting mixture was basified to pH 10 with saturated aq. NaOH. Aqueous layer was extracted with DCM and MeOH (9:1) mixture. Organic layer was dried on anhydrous $Na_2SO_4$ and evaporated on rotavapour to obtain crude. Crude was purified by combi-flash using MeOH and DCM (6:94) as eluent to afford the titled compound as a white solid (180 mg). $^1$H-NMR (δ ppm, DMSO-$d_6$, 400 MHz): 10-94 (s, 1H), 7.98 (d, J 9.5, 1H), 7.48-7.42 (m, 1H), 7.41-7.32 (m, 3H), 7.24 (d, J 7.7, 1H), 7.04 (s, 2H), 4.38 (d, J 12.2, 1H), 4.02 (d, J 12.4, 1H), 3.78 (s, 2H), 3.23-3.05 (m, 3H), 2.11-2.03 (m, 1H), 1.80-1.70 (m, 2H), 1.65-1.53 (m, 1H). MS (m/z): 480.4 [M+H]$^+$.

Intermediate 29: Ethyl 1-(6-(2-(2-chlorophenyl)acetamido)pyridazin-3-yl)piperidine-4-carboxylate Intermediate 21 (1.35 g, 5.4 mmol), 2-Chlorophenylacetic acid (1.11 g, 6.5 mmol), HATU (4.5 g, 11.85 mmol), DIPEA (2.8 ml, 16.2 mmol) were taken in DMF (4 ml). This mixture was stirred at rt under inert atmosphere for 12 h. Reaction mass was diluted with water and extracted with DCM. DCM layer was dried on anhydrous $Na_2SO_4$ and DCM removed on rotavapour to obtain crude. Crude was purified by column chromatography on 60-120 mesh silica gel using MeOH and DCM (1:99) as eluent to afford the titled compound as a brown gummy solid (510 mg). $^1$H-NMR (δ ppm, DMSO-$d_6$, 400 MHz): 10.91 (s, 1H), 7.97 (d, J 9.7, 1H), 7.45-7.38 (m, 2H), 7.36-7.25 (m, 3H), 4.20-4.13 (m, 2H), 4.06 (q, J 7.1, 2H), 3.90 (s, 2H), 2.99 (t, J 11.1, 2H), 2.64-2.56 (m, 1H), 1.93-1.85 (m, 2H), 1.62-1.51 (m, 2H), 1.17 (t, J 7.1, 3H).

Intermediate 30: 1-(6-(2-(2-Chlorophenyl)acetamido)pyridazin-3-yl)piperidine-4-carboxylic acid Intermediate 29 (510 mg, 1.26 mmol) was dissolved in MeOH and water. To this mixture added NaOH (302 mg, 7.6 mmol). This mixture was stirred at rt for 6 h. Reaction mass was acidified with dil. HCl up to pH~5 to obtain a solid. Solid was filtered and dried to obtain the titled compound as a yellow solid (350 mg). $^1$H-NMR (δ ppm, DMSO-$d_6$, 400 MHz): 12.22 (s, 1H), 10.90 (s, 1H), 7.96 (d, J 9.5, 1H), 7.45-7.38 (m, 2H), 7.36-7.25 (m, 3H), 4.14 (d, J 13.2, 2H), 3.90 (s, 2H), 2.98 (t, J 11.4, 2H), 2.55-2.50 (m, 1H), 1.87 (d, J 11.2, 2H), 1.61-1.50 (m, 2H).

Intermediate 31: N-(6-(4-(5-Amino-1,3,4-thiadiazol-2-yl)piperidin-1-yl)pyridazin-3-yl)-2-(2-chlorophenyl)acetamide Intermediate 30 (350 mg, 0.93 mmol), Thiosemicarbazide (255 mg, 2.3 mmol) and $POCl_3$ (3.5 ml) were mixed and heated to 90° C. for 3 h. After completion of reaction, reaction mass was cooled to rt and quenched into crushed ice (150 g). The resulting mixture was basified to pH 10 with saturated aq. NaOH. Aqueous layer was extracted with DCM and MeOH (9:1) mixture. Organic layer was dried on anhydrous $Na_2SO_4$ and evaporated on rotavapour to obtain crude. Crude was purified by combi-flash using MeOH and DCM (6:94) as eluent to afford the titled compound as a brown solid (40 mg). $^1$H-NMR (δ ppm, DMSO-$d_6$, 400 MHz): 10.91 (s, 1H), 7.98 (d, J 9.4, 1H), 7.46-7.35 (m, 3H), 7.31-7.25 (m, 2H), 7.01 (s, 2H), 4.28 (d, J 12.9, 2H), 3.90 (s, 2H), 3.20-3.11 (m, 1H), 3.10 (t, J 11.4, 2H), 2.02 (d, J 11.6, 2H), 1.70-1.59 (m, 2H).

Intermediate 32: 1-(6-aminopyridazin-3-yl)piperidine-4-carbonitrile

3-Amino-6-chloropyridazine (3 g, 23.2 mmol) and 4-Cyanopiperidine (3.8 g, 34.7) mmol were mixed and heated to 180° C. for 4 h. After 4 h, reaction mass cooled to rt and hard reaction mass dissolved in MeOH and DCM (1:9) mixture. MeOH and DCM were removed on rotavapour to obtain crude. Crude was purified by column chromatography on 60-120 mesh silica gel to obtain the titled compound (4.6 g) as a dark red solid.

Intermediate 33: N-(6-(4-cyanopiperidin-1-yl)pyridazin-3-yl)-2-(2-fluorophenyl)acetamide Intermediate 32 (365 mg, 1.8 mmol), 2-Fluorophenylacetic acid (388 mg, 2.5 mmol), HATU (1.5 g, 3.95 mmol), DIPEA (0.9 ml, 5.4 mmol) were taken in DMF (3 ml). This mixture was stirred at rt under inert atmosphere for 1 h. Reaction mass was diluted with water to obtain a solid. Solid was dried on high vacuum to obtain the titled compound (80 mg) as a brown solid. $^1$H-NMR (δ ppm, DMSO-$d_6$, 400 MHz): 10.93 (s, 1H), 7.99 (d, J 9.8, 1H), 7.40-7.25 (m, 3H), 7.19-7.11 (m, 2H), 3.85-3.75 (m, 4H), 3.41-3.35 (m, 2H), 3.16-3.05 (m, 1H), 1.98-1.90 (m, 2H), 1.80-1.70 (m, 2H).

Intermediate 34: N-(6-(4-(5-amino-1,3,4-thiadiazol-2-yl)piperidin-1-yl)pyridazin-3-yl)-2-(2-fluorophenyl)acetamide Intermediate 33 (80 mg, 0.24 mmol), Thiosemicarbazide (43 mg, 0.47 mmol) and trifluoroacetic acid (1 ml) were mixed and heated to 90° C. for 3 h. After completion of reaction, reaction mass was cooled to rt and basified to pH 14 with saturated aq. NaOH to obtain a solid. Solid was filtered and dried on high vacuum to obtain the titled compound (60 mg) as a pale-brown solid. 1H-NMR (δ ppm, DMSO-d6, 400 MHz): 10.91 (s, 1H), 7.98 (d, J 10, 1H), 7.40-7.26 (m, 3H), 7.19-7.12 (m, 2H), 7.01 (s, 2H), 4.28 (d, J 12.6, 2H), 3.80 (s, 2H), 3.20-3.10 (m, 1H), 3.01 (t, J 12.2, 2H), 2.03 (d, J 11.6, 2H), 1.70-1.58 (m, 2H).

Intermediate 35: N-(6-(4-cyanopiperidin-1-yl)pyridazin-3-yl)-2-(pyridin-2-yl)acetamide Intermediate 32 (500 mg, 2.5 mmol), 2-Pyridineacetic acid hydrochloride (500 mg, 2.95 mmol), HATU (2.05 g, 5.41 mmol), DIPEA (1.27 ml, 7.38 mmol) were taken in DMF (3 ml). This mixture was stirred at rt under inert atmosphere for 1 h. Reaction mass was diluted with water to obtain a solid. Solid was dried on high vacuum to obtain the titled compound (370 mg) as a brown solid. MS (m/z): 322.26 [M+H]$^+$.

Intermediate 36: N-(6-(4-(5-amino-1,3,4-thiadiazol-2-yl)piperidin-1-yl)pyridazin-3-yl)-2-(pyridin-2-yl)acetamide Intermediate 35 (360 mg, 1.1 mmol), Thiosemicarbazide (203 mg, 2.22 mmol) and trifluoroacetic acid (4 ml) were mixed and heated to 90° C. for 3 h. After completion of reaction, reaction mass was cooled to rt and basified to pH 14 with saturated aq. NaOH to obtain a solid. Solid was filtered and dried on high vacuum to obtain the titled compound (180 mg) as a pale-brown solid.

Intermediate 37: N-(6-(4-cyanopiperidin-1-yl)pyridazin-3-yl)-2-(pyridin-3-yl)acetamide Intermediate 32 (500 mg, 2.5 mmol), 3-Pyridineacetic acid hydrochloride (500 mg, 2.95 mmol), HATU (2.05 g, 5.41 mmol), DIPEA (1.27 ml, 7.38 mmol) were taken in DMF (3 ml). This mixture was stirred at rt under inert atmosphere for 1 h. Reaction mass was diluted with water to obtain a solid. Solid was purified by combi-flash using MeOH and DCM (5:95) as eluent to afford the titled compound (180 mg) as a brown solid. MS (m/z): 322.8 [M+H]$^+$.

Intermediate 38: N-(6-(4-(5-amino-1,3,4-thiadiazol-2-yl)piperidin-1-yl)pyridazin-3-yl)-2-(pyridin-3-yl)acetamide Intermediate 37 (180 mg, 0.55 mmol), Thiosemicarbazide (101 mg, 1.1 mmol) and trifluoroacetic acid (3 ml) were mixed and heated to 90° C. for 3 h. After completion of reaction, reaction mass was cooled to rt and basified to pH 14 with saturated aq. NaOH to obtain a solid. Solid was filtered and dried on high vacuum to obtain the titled compound (60 mg) as a pale-brown solid.

Intermediate 39: 2-(1-(6-aminopyridazin-3-yl)piperidin-4-yl)acetonitrile

3-Amino-6-chloropyridazine (350 mg, 2.70 mmol) and 2-(piperidin-4-yl)acetonitrile (670 mg, 5.4 mmol) were mixed and heated to 180° C. for 4 h. After 4 h, reaction mass cooled to rt and hard reaction mass dissolved in MeOH and DCM (1:9) mixture. MeOH and DCM were removed on rotavapour to obtain crude. Crude was purified by column chromatography on 60-120 mesh silica gel to obtain the titled compound (300 mg) as a brown gummy solid.

Intermediate 40: N-(6-(4-(cyanomethyl)piperidin-1-yl)pyridazin-3-yl)-2-(3-(trifluoromethoxy)phenyl)acetamide Intermediate 39 (300 mg, 1.38 mmol), 3-(Trifluoromethoxy)phenylacetic acid (360 mg, 1.63 mmol), HATU (1.2 g, 3.16 mmol), DIPEA (0.73 ml, 4.2 mmol) were taken in DMF (3 ml). This mixture was stirred at rt under inert atmosphere for 1 h. Reaction mass was diluted with water to obtain a solid. Solid was purified by column chromatography using MeOH and DCM (2:98) as eluent to afford the titled compound (50 mg) as a brown solid. $^1$H-NMR (δ ppm, DMSO-d$_6$, 400 MHz): 10.91 (s, 1H), 7.96 (d, J 9.7, 1H), 7.48-7.42 (m, 1H), 7.38-7.30 (m, 3H), 7.23 (d, J 8.1, 1H), 4.27 (d, J 13.2, 2H), 2.86 (t, J 11.7, 2H), 2.55-2.50 (m, 2H), 1.95-1.85 (m, 1H), 1.77 (d, J 12.9, 2H), 1.73-1.58 (m, 2H).

Intermediate 41: N-(6-(4-((5-amino-1,3,4-thiadiazol-2-yl)methyl)piperidin-1-yl)pyridazin-3-yl)-2-(3-(trifluoromethoxy)phenyl)acetamide Intermediate 40 (50 mg, 0.12 mmol), Thiosemicarbazide (22 mg, 0.24 mmol) and trifluoroacetic acid (2 ml) were mixed and heated to 90° C. for 12 h. After completion of reaction, reaction mass was cooled to rt and basified to pH 14 with saturated aq. NaOH to obtain a solid. Solid was filtered and dried on high vacuum to obtain the titled compound (34 mg) as a brown solid. MS (m/z): 494.1 [M+H]$^+$.

Example 1

2-(Pyridin-2-yl)-N-(5-(1-(6-(2-(3-(trifluoromethoxy)phenyl)acetamido)pyridin-3-yl)piperidin-4-yl)-1,3,4-thiadiazol-2-yl)acetamide Intermediate 5 (100 mg, 0.21 mmol), 2-Pyridylacetic acid hydrochloride (44 mg, 0.25 mmol), HATU (96 mg, 0.25 mmol), N-Ethyldiisopropyl amine (0.1 ml, 0.62 mmol) were dissolved in DMF (2 ml). This mixture was stirred at rt for 30 mins. Reaction mass was diluted with water and extracted with EtOAc. Organic layer was washed with water. Organic layer was dried on anhydrous Na$_2$SO$_4$. EtOAc was removed on rotavapour to obtain crude. Crude was purified by column chromatography on 60-120 mesh silica gel using Methanol and DCM (3:97) as eluent to afford the titled compound (15 mg) as a brown solid. M.P.: 195-197° C. $^1$H-NMR (δ ppm, DMSO-d$_6$, 400 MHz): 12.64 (s, 1H), 10.44 (s, 1H), 8.47 (d, J 4.2, 1H), 8.03 (d, J 2.7, 1H), 7.87 (d, J 9, 1H), 7.75 (t, J 7.7, 1H), 7.48-7.32 (m, 5H), 7.30-7.20 (m, 2H), 4.00 (s, 2H), 3.73 (s, 2H), 3.72-3.65 (m, 2H), 3.30-3.20 (m, 1H), 2.84 (t, J 11.7, 2H), 2.11 (d, J 11.5, 2H), 1.90-1.78 (m, 2H).

Example 2

(RS)-2-(Pyridin-2-yl)-N-(5-(1-(6-(2-(3-(trifluoromethoxy)phenyl)acetamido)pyridin-3-yl) piperidin-3-yl)-1,3,4-thiadiazol-2-yl)acetamide Intermediate 10 (500 mg, 1.04 mmol), 2-Pyridylacetic acid hydrochloride (220 mg, 1.27 mmol), HATU (480 mg, 1.27 mmol), N-Ethyldiisopropyl amine (0.5 ml, 3.09 mmol) were dissolved in DMF (3 ml). This mixture was stirred at rt for 30 mins. Reaction mass was diluted with water and extracted with DCM. Organic layer was washed with water. Organic layer was dried on anhydrous $Na_2SO_4$. DCM was removed on rotavapour to obtain crude. Crude was purified by column chromatography by combi-flash using Methanol and DCM (4:96) as eluent to afford the titled compound (10 mg) as a brown solid. M.P.: 187-190° C. $^1$H-NMR (δ ppm, DMSO-$d_6$, 400 MHz): 12.63 (s, 1H), 10.46 (s, 1H), 8.48 (d, J 4, 1H), 8.04 (d, J 2.6, 1H), 7.88 (d, J 9, 1H), 7.75 (d, J 7.6, 1H), 7.46-7.30 (m, 5H), 7.29-7.20 (m, 2H), 3.99 (s, 2H), 3.79-3.69 (m, 3H), 3.48-3.40 (m, 1H), 3.15-3.08 (m, 1H), 3.00-2.90 (m, 1H), 2.30-2.20 (m, 1H), 2.15-2.05 (m, 1H), 1.82-1.70 (m, 3H).

Example 2A (R) or (S) 2-(Pyridin-2-yl)-N-(5-(1-(6-(2-(3-(trifluoromethoxy)phenyl)acetamido) pyridin-3-yl)piperidin-3-yl)-1,3,4-thiadiazol-2-yl)acetamide The enantiomerically pure isomer was separated by preparative SFC conditions from 2-(Pyridin-2-yl)-N-(5-(1-(6-(2-(3-(trifluoromethoxy)phenyl)acetamido)pyridin-3-yl)piperidin-3-yl)-1,3,4-thiadiazol-2-yl)acetamide (Example: 2) (0.300 g) on a CHIRALPAK IC 4.6*250, 5 um(Daicel) using n-Hexane(0.1% DEA)/Ethanol(0.1% DEA)=40/60 as the mobile phase at a flow rate of 1.0 ml/min to obtain the titled compound (55 mg) as a brown solid e.e. 100%. Rt: 12.34 min. M.P.: 122-124° C. $^1$H-NMR (δ ppm, DMSO-$d_6$, 400 MHz): 12.63 (s, 1H), 10.46 (s, 1H), 8.48 (d, J 4, 1H), 8.04 (d, J 2.6, 1H), 7.88 (d, J 9, 1H), 7.75 (d, J 7.6, 1H), 7.46-7.30 (m, 5H), 7.29-7.20 (m, 2H), 3.99 (s, 2H), 3.79-3.69 (m, 3H), 3.48-3.40 (m, 1H), 3.15-3.08 (m, 1H), 3.00-2.90 (m, 1H), 2.30-2.20 (m, 1H), 2.15-2.05 (m, 1H), 1.82-1.70 (m, 3H).

Example 2B (S) or (R) 2-(Pyridin-2-yl)-N-(5-(1-(6-(2-(3-(trifluoromethoxy)phenyl)acetamido) pyridin-3-yl)piperidin-3-yl)-1,3,4-thiadiazol-2-yl)acetamide The enantiomerically pure isomer was separated by preparative SFC conditions from 2-(Pyridin-2-yl)-N-(5-(1-(6-(2-(3-(trifluoromethoxy)phenyl)acetamido)pyridin-3-yl)piperidin-3-yl)-1,3,4-thiadiazol-2-yl)acetamide (Example: 2) (0.300 g) on a CHIRALPAK IC 4.6*250, 5 um(Daicel) using n-Hexane(0.1% DEA)/Ethanol(0.1% DEA)=40/60 as the mobile phase at a flow rate of 1.0 ml/min to obtain the titled compound (45 mg) as a brown solid e.e. 100%. Rt: 14.47 min. M.P.: 129-131° C. $^1$H-NMR (δ ppm, DMSO-$d_6$, 400 MHz): 12.63 (s, 1H), 10.46 (s, 1H), 8.48 (d, J 4, 1H), 8.04 (d, J 2.6, 1H), 7.88 (d, J 9, 1H), 7.75 (d, J 7.6, 1H), 7.46-7.30 (m, 5H), 7.29-7.20 (m, 2H), 3.99 (s, 2H), 3.79-3.69 (m, 3H), 3.48-3.40 (m, 1H), 3.15-3.08 (m, 1H), 3.00-2.90 (m, 1H), 2.30-2.20 (m, 1H), 2.15-2.05 (m, 1H), 1.82-1.70 (m, 3H).

Example 3

(RS)-2-(Pyridin-3-yl)-N-(5-(1-(6-(2-(3-(trifluoromethoxy)phenyl)acetamido)pyridin-3-yl) piperidin-3-yl)-1,3,4-thiadiazol-2-yl)acetamide Intermediate 10 (500 mg, 1.04 mmol), 3-Pyridylacetic acid hydrochloride (220 mg, 1.26 mmol), HATU (480 mg, 1.25 mmol), N-Ethyldiisopropyl amine (0.5 ml, 3.1 mmol) were dissolved in DMF (3 ml). This mixture was stirred at rt for 30 mins. Reaction mass was diluted with water and extracted with DCM. Organic layer was washed with water. Organic layer was dried on anhydrous $Na_2SO_4$. DCM was removed on rotavapour to obtain crude. Crude was purified by combi-flash using Methanol and DCM (5:95) as eluent to afford the titled compound (6 mg) as a Pale-Yellow solid. M.P.: 145-147° C. $^1$H-NMR (δ ppm, DMSO-$d_6$, 400 MHz): 12.69 (s, 1H), 10.47 (s, 1H), 8.55-8.51 (m, 2H), 8.03 (s, 1H), 7.90-7.80 (m, 2H), 7.49-7.40 (m, 3H), 7.30-7.27 (m, 2H), 7.22 (d, J 8, 1H), 3.89 (s, 2H), 3.75-3.70 (m, 3H), 3.20-3.10 (m, 2H), 3.05-2.92 (m, 2H), 2.13-2.04 (m, 1H), 1.80-1.60 (m, 3H).

Example 3A (R) or (S) 2-(Pyridin-3-yl)-N-(5-(1-(6-(2-(3-(trifluoromethoxy)phenyl)acetamido) pyridin-3-yl)piperidin-3-yl)-1,3,4-thiadiazol-2-yl)acetamide The enantiomerically pure isomer was separated by preparative SFC conditions from 2-(Pyridin-3-yl)-N-(5-(1-(6-(2-(3-(trifluoromethoxy)phenyl)acetamido)pyridin-3-yl)piperidin-3-yl)-1,3,4-thiadiazol-2-yl)acetamide (Example: 3) (460 mg) on a CHIRALPAK IC 4.6*250, 5 um(Daicel) using n-Hexane(0.1% DEA)/Ethanol(0.1% DEA)=50/50 as the mobile phase at a flow rate of 1.0 ml/min to obtain the titled compound (100 mg) as a brown solid e.e. 100%. Rt: 12.11 min. M.P.: 170-172° C. $^1$H-NMR (δ ppm, DMSO-$d_6$, 400 MHz): 12.69 (s, 1H), 10.47 (s, 1H), 8.55-8.51 (m, 2H), 8.03 (s, 1H), 7.90-7.80 (m, 2H), 7.49-7.40 (m, 3H), 7.30-7.27 (m, 2H), 7.22 (d, J 8, 1H), 3.89 (s, 2H), 3.75-3.70 (m, 3H), 3.20-3.10 (m, 2H), 3.05-2.92 (m, 2H), 2.13-2.04 (m, 1H), 1.80-1.60 (m, 3H).

Example 3B (S) or (R) 2-(Pyridin-3-yl)-N-(5-(1-(6-(2-(3-(trifluoromethoxy)phenyl)acetamido) pyridine-3-yl)piperidin-3-yl)-1,3,4-thiadiazol-2-yl)acetamide The enantiomerically pure isomer was separated by preparative SFC conditions from 2-(Pyridin-3-yl)-N-(5-(1-(6-(2-(3-(trifluoromethoxy)phenyl)acetamido)pyridin-3-yl)piperidin-3-yl)-1,3,4-thiadiazol-2-yl)acetamide (Example: 3) (460 mg) on a CHIRALPAK IC 4.6*250, 5 um(Daicel) using n-Hexane(0.1% DEA)/Ethanol(0.1% DEA)=50/50 as the mobile phase at a flow rate of 1.0 ml/min to obtain the titled compound (100 mg) as a brown solid e.e. 100%. Rt: 14.12 min. M.P.: 141-143° C. $^1$H-NMR (δ ppm, DMSO-$d_6$, 400 MHz): 12.69 (s, 1H), 10.47 (s, 1H), 8.55-8.51 (m, 2H), 8.03 (s, 1H), 7.90-7.80 (m, 2H), 7.49-7.40 (m, 3H), 7.30-7.27 (m, 2H), 7.22 (d, J 8, 1H), 3.89 (s, 2H), 3.75-3.70 (m, 3H), 3.20-3.10 (m, 2H), 3.05-2.92 (m, 2H), 2.13-2.04 (m, 1H), 1.80-1.60 (m, 3H).

Example 4

2-(Pyridin-3-yl)-N-(5-(1-(6-(2-(3-(trifluoromethoxy) phenyl)acetamido)pyridin-3-yl)piperidin-4-yl)-1,3,4-thiadiazol-2-yl)acetamide Intermediate 5 (70 mg, 0.15 mmol), 3-Pyridylacetic acid hydrochloride (31 mg, 0.18 mmol), HATU (67 mg, 0.18 mmol), N-Ethyldiisopropyl amine (0.1 ml, 0.45 mmol) were dissolved in DMF (2 ml). This mixture was stirred at rt for 16 h. Reaction mass was diluted with water and extracted with DCM. Organic layer was washed with water. Organic layer was dried on anhydrous Na$_2$SO$_4$. DCM was removed on rotavapour to obtain crude. Crude was purified by column chromatography on 60-120 mesh silica gel using Methanol and DCM (5:95) as eluent to afford the titled compound (15 mg) as a pale-brown solid. M.P.: 208-210° C. $^1$H-NMR (δ ppm, DMSO-d$_6$, 400 MHz): 12.70 (s, 1H), 10.47 (s, 1H), 8.58 (s, 1H), 8.54 (d, J 4.8, 1H), 8.03 (d, J 2.7, 1H), 7.91-7.85 (m, 2H), 7.51-7.39 (m, 3H), 7.38-7.32 (m, 2H), 7.22 (d, J 7.6, 1H), 3.92 (s, 2H), 3.73 (s, 2H), 3.72-3.65 (m, 2H), 3.31-3.20 (m, 1H), 2.85 (t, J 10.8, 2H), 2.10 (d, J 11.9, 2H), 1.90-1.76 (m, 2H).

Example 5

2-(3-Cyanophenyl)-N-(5-(1-(6-(2-(3-(trifluoromethoxy)phenyl)acetamido)pyridin-3-yl)piperidin-4-yl)-1,3,4-thiadiazol-2-yl)acetamide Intermediate 5 (100 mg, 0.15 mmol), 3-Cyanophenylacetic acid (58 mg, 0.36 mmol), HATU (96 mg, 0.25 mmol), N-Ethyldiisopropyl amine (0.11 ml, 0.63 mmol) were dissolved in DMF (2 ml). This mixture was stirred at rt for 16 h. Reaction mass was diluted with water and extracted with DCM. Organic layer was washed with water. Organic layer was dried on anhydrous Na$_2$SO$_4$. DCM was removed on rotavapour to obtain crude. Crude was purified by combi-flash using Methanol and DCM (5:95) as eluent to afford the titled compound (50 mg) as a pale-yellow solid. M.P.: 211-213° C. $^1$H-NMR (δ ppm, DMSO-d$_6$, 400 MHz): 12.71 (s, 1H), 10.5 (s, 1H), 8.03 (d, J 2.4, 1H), 7.88 (d, J 9, 1H), 7.79-7.73 (m, 2H), 7.65 (d, J 7.9, 1H), 7.57-7.51 (m, 1H), 7.48-7.37 (m, 2H), 7.36-7.31 (m, 2H), 7.23 (d, J 7.9, 1H), 3.90 (s, 2H), 3.75-3.65 (m, 4H), 3.30-3.20 (m, 1H), 2.83 (t, J 11.6, 2H), 2.10 (d, J 12.6, 2H), 1.88-1.78 (m, 2H).

Example 6

2-(Pyridin-2-yl)-N-(5-(4-(5-(2-(3-(trifluoromethoxy)phenyl)acetamido)-1,3,4-thiadiazol-2-yl)piperidin-1-yl)pyridin-2-yl)acetamide Intermediate 15 (100 mg, 0.25 mmol), 3-(Trifluoromethoxy)phenylacetic acid (66 mg, 0.3 mmol), HATU (114 mg, 0.3 mmol), N-Ethyldiisopropyl amine (0.13 ml, 0.76 mmol) were dissolved in DMF (1.5 ml). This mixture was stirred at rt for 16 h. Reaction mass was diluted with water and extracted with DCM. Organic layer was washed with water. Organic layer was dried on anhydrous Na$_2$SO$_4$. DCM was removed on rotavapour to obtain crude. Crude was purified by combi-flash using Methanol and DCM (8:92) as eluent to afford the titled compound (60 mg) as a pale-yellow solid. M.P.: 188-191° C. $^1$H-NMR (δ ppm, DMSO-d$_6$, 400 MHz): 12.65 (s, 1H), 10.40 (s, 1H), 8.49 (d, J 4.8, 1H), 8.03 (d, J 2.8, 1H), 7.89 (d, J 9, 1H), 7.73 (dt, J 1.8, 7.7, 1H), 7.49-7.43 (m, 1H), 7.42-7.31 (m, 4H), 7.28-7.22 (m, 2H), 3.88 (s, 2H), 3.87 (s, 2H), 3.70 (d, J 12.6, 2H), 3.25-3.20 (m, 1H), 2.84 (t, J 11.6, 2H), 2.11 (d, J 11.5, 2H), 1.90-1.77 (m, 2H).

Example 7

2-(Pyridin-2-yl)-N-(5-(3-(5-(2-(3-(trifluoromethoxy)phenyl)acetamido)-1,3,4-thiadiazol-2-yl)piperidin-1-yl)pyridin-2-yl)acetamide Intermediate 20 (100 mg, 0.25 mmol), 3-(Trifluoromethoxy)phenylacetic acid (66 mg, 0.3 mmol), HATU (114 mg, 0.3 mmol), N-Ethyldiisopropyl amine (0.13 ml, 0.76 mmol) were dissolved in DMF (1.5 ml). This mixture was stirred at rt for 16 h. Reaction mass was diluted with water and extracted with DCM. Organic layer was washed with water. Organic layer was dried on anhydrous Na$_2$SO$_4$. DCM was removed on rotavapour to obtain crude. Crude was purified by combi-flash using Methanol and DCM (5:95) as eluent to afford the titled compound (40 mg) as a pale-yellow solid. M.P.: 151-153° C. $^1$H-NMR (δ ppm, DMSO-d$_6$, 400 MHz): 12.69 (s, 1H), 10.47 (s, 1H), 8.48 (d, J 4.0, 1H), 8.04 (d, J 2.8, 1H), 7.90 (d, J 9, 1H), 7.73 (dt, J 1.7, 7.7, 1H), 7.49-7.40 (m, 2H), 7.39-7.32 (m, 3H), 7.28-7.23 (m, 2H), 3.87 (s, 4H), 3.70 (d, J 12.4, 1H), 3.49-3.39 (m, 2H), 3.14-3.06 (m, 1H), 2.99-2.90 (m, 1H), 2.10-2.04 (m, 1H), 1.80-1.65 (m, 3H). MS (m/z): 597.8 [M+H]$^+$ Example 8

2-(pyridin-2-yl)-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (100 mg, 0.2 mmol), 2-Pyridiylacetic acid hydrochloride (44 mg, 0.25 mmol), HATU (170 mg, 0.44 mmol), N-Ethyldiisopropyl amine (0.1 ml, 0.57 mmol) were dissolved in DMF (2 ml). This mixture was stirred at rt for 1 h. Reaction mass was diluted with water and extracted with DCM. Organic layer was washed with water. Organic layer was dried on anhydrous Na$_2$SO$_4$. DCM was removed on rotavapour to obtain crude. Crude was purified on Combi-flash using DCM and MeOH (95:5) as eluent to afford the titled compound (60 mg) as a yellow solid. M.P.: 202-205° C. $^1$H-NMR (δ ppm, DMSO-d$_6$, 400 MHz): 12.68 (bs, 1H), 10.93 (s, 1H), 8.48 (d, J 4.2, 1H), 7.99 (d, J 9.8, 1H), 7.75 (dt, J 1.7, 7.7, 1H), 7.47-7.43 (m, 1H), 7.39-7.32 (m, 4H), 7.29-7.21 (m, 2H), 4.30 (d, J 13.2, 2H), 3.99 (s, 2H), 3.78 (s, 2H), 3.40-3.30 (m, 1H), 3.05 (t, J 11.7, 2H), 2.09 (d, J 10.6, 2H), 1.80-1.65 (m, 2H). MS (m/z): 599.6 [M+H]$^+$.

Example 9

2-(Pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide Intermediate 28 (80 mg, 0.17 mmol), 2-Pyridiylacetic acid hydrochloride (34 mg, 0.2 mmol), HATU (138 mg, 0.37 mmol), N-Ethyldiisopropyl amine (0.08 ml, 0.5 mmol) were dissolved in DMF (1 ml). This mixture was stirred at rt for 1 h. Reaction mass was diluted with water and extracted with DCM:MeOH (9:1). Organic layer was washed with water. Organic layer was dried on anhydrous Na$_2$SO$_4$. DCM and MeOH were removed on rotavapour to obtain crude. Crude was purified on Combi-flash using DCM and MeOH (95:5) as eluent to afford the titled compound (20 mg) as a pale-yellow solid. M.P.: 202-205° C. M.P.: 243-246° C. $^1$H-NMR (δ ppm, DMSO-d$_6$, 400 MHz): 12.71 (s, 1H), 10.95 (s, 1H), 8.47 (d, J 4.4, 1H), 7.99 (d, J 9.5, 1H), 7.75 (t, J 7.4, 1H), 7.48-7.32 (m, 5H), 7.30-7.21 (m, 2H), 4.42 (d, J 10, 1H), 4.05-3.97 (m, 3H), 3.78 (s, 2H), 3.45-3.35 (m, 2H), 3.15 (t, J 11.1, 1H), 2.19-2.10 (m, 1H), 1.90-1.74 (m, 2H), 1.67-1.58 (m, 1H). MS (m/z): 599.5 [M+H]$^+$.

Example 10

2-(Pyridin-3-yl)-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (80 mg, 0.17 mmol), 3-Pyridiylacetic acid hydrochloride (35 mg, 0.2 mmol), HATU (140 mg, 0.37 mmol), N-Ethyldiisopropyl amine (0.08 ml, 0.5 mmol) were dissolved in DMF (2 ml). This mixture was stirred at rt for 1 h. Reaction mass was diluted with water to obtain a solid. Solid was filtered and purified on Combi-flash using DCM and MeOH (94:6) as eluent to afford the titled compound (25 mg) as a pale-yellow solid. M.P.: 222-223° C. $^1$H-NMR ($\delta$ ppm, DMSO-$d_6$, 400 MHz): 12.72 (s, 1H), 10.93 (s, 1H), 8.50 (bs, 1H), 8.46 (bs, 1H), 7.99 (d, J 9.7, 1H), 7.72 (d, J 7.8, 1H), 7.48-7.42 (m, 1H), 7.39-7.32 (m, 4H), 7.24 (d, J 8.1, 1H), 4.30 (d, J 13.3, 2H), 3.85 (s, 2H), 3.78 (s, 2H), 3.40-3.35 (m, 1H), 3.05 (t, J 11.7, 2H), 2.09 (d, J 11.2, 2H), 1.80-1.67 (m, 2H).

Example 11

2-(3-(Methylsulfonamido)phenyl)-N-(5-(1-(6-(2-(3-(trifluoromethoxy)phenyl)acetamido) pyridazin-3-yl) piperidin-4-yl)-1,3,4-thiadiazol-2-yl)acetamide Intermediate 24 (80 mg, 0.17 mmol), 2-(3-(Methylsulfonamido)phenyl)acetic acid (46 mg, 0.2 mmol), HATU (140 mg, 0.37 mmol), N-Ethyldiisopropyl amine (0.08 ml, 0.5 mmol) were dissolved in DMF (2 ml). This mixture was stirred at rt for 1 h. Reaction mass was diluted with water. Aqueous layer was extracted with DCM and MeOH (9:1) mixture. Organic layer was washed with water and aq. NaHCO$_3$ solution. Organic layer dried on anhydrous Na$_2$SO$_4$ and organic layer distilled on rotavapour to obtain crude. Crude was purified on Combi-flash using DCM and MeOH (95:5) as eluent to afford the titled compound (20 mg) as a pale-brown solid. M.P.: 228-231° C. $^1$H-NMR ($\delta$ ppm, DMSO-$d_6$, 400 MHz): 12.69 (s, 1H), 10.93 (s, 1H), 9.72 (s, 1H), 7.99 (d, J 9.8, 1H), 7.49-7.42 (m, 1H), 7.39-7.32 (m, 3H), 7.30-7.22 (m, 2H), 7.16 (s, 1H), 7.10 (d, J 7.9, 1H), 7.04 (d, J 7.5, 1H), 4.30 (d, J 13, 2H), 3.78 (s, 2H), 3.76 (s, 2H), 3.40-3.30 (m, 1H), 3.05 (t, J 11.6, 2H), 2.97 (s, 3H), 2.13-2.05 (m, 2H), 1.80-1.65 (m, 2H).

Example 12

2-(2-Chlorophenyl)-N-(6-(4-(5-(2-(pyridin-2-yl) acetamido)-1,3,4-thiadiazol-2-yl) piperidin-1-yl) pyridazin-3-yl)acetamide Intermediate 31 (38 mg, 0.09 mmol), 2-Pyridiylacetic acid hydrochloride (18 mg, 0.1 mmol), HATU (73 mg, 0.19 mmol), N-Ethyldiisopropyl amine (0.05 ml, 0.26 mmol) were dissolved in DMF (1 ml). This mixture was stirred at rt for 1 h. Reaction mass was diluted with water and extracted with DCM:MeOH (9:1). Organic layer was washed with water. Organic layer was dried on anhydrous Na$_2$SO$_4$. DCM and MeOH were removed on rotavapour to obtain crude. Crude was purified on Combi-flash using DCM and MeOH (95:5) as eluent to afford the titled compound (8 mg) as a pale-brown solid. M.P.: 225-227° C. $^1$H-NMR ($\delta$ ppm, DMSO-$d_6$, 400 MHz): 12.68 (s, 1H), 10.92 (s, 1H), 8.48 (d, J 4.1, 1H), 7.98 (d, J 9.8, 1H), 7.75 (dt, J 1.8, 7.7, 1H), 7.44-7.36 (m, 4H), 7.33-7.25 (m, 3H), 4.31 (d, J 13, 2H), 3.99 (s, 2H), 3.90 (s, 2H), 3.40-3.35 (m, 1H), 3.05 (t, J 11.8, 2H), 2.10 (d, J 11.8, 2H), 1.81-1.69 (m, 2H).

Example 13

2-(2-Chlorophenyl)-N-(5-(1-(6-(2-(3-(trifluoromethoxy)phenyl)acetamido)pyridazin-3-yl)piperidin-3-yl)-1,3,4-thiadiazol-2-yl)acetamide Intermediate 28 (100 mg, 0.2 mmol), 2-Chlorophenylacetic acid (42 mg, 0.25 mmol), HATU (173 mg, 0.46 mmol), N-Ethyldiisopropyl amine (0.1 ml, 0.6 mmol) were dissolved in DMF (1 ml). This mixture was stirred at rt for 1 h. Reaction mass was diluted with water and extracted with DCM:MeOH (9:1). Organic layer was washed with water. Organic layer was dried on anhydrous Na$_2$SO$_4$. DCM and MeOH were removed on rotavapour to obtain crude. Crude was purified on Combi-flash using DCM and MeOH (97:3) as eluent to afford the titled compound (40 mg) as a pale-brown solid. M.P.: 202-205° C. M.P.: 127-130° C. $^1$H-NMR ($\delta$ ppm, DMSO-$d_6$, 400 MHz): 12.75 (s, 1H), 10.94 (s, 1H), 7.98 (d, J 9.7, 1H), 7.48-7.29 (m, 8H), 7.24 (d, J 7.5, 1H), 4.41 (d, J 10.1, 1H), 4.05-3.95 (m, 3H), 3.78 (s, 2H), 3.40-3.35 (m, 2H), 3.20-3.10 (m, 1H), 2.19-2.10 (m, 1H), 1.88-1.71 (m, 2H), 1.68-1.57 (m, 1H).

Example 14

2-(2-Fluorophenyl)-N-(6-(4-(5-(2-(pyridin-2-yl)acetamido)-1,3,4-thiadiazol-2-yl)piperidin-1-yl) pyridazin-3-yl)acetamide Intermediate 34 (60 mg, 0.15 mmol), 2-Pyridylacetic acid hydrochloride (30 mg, 0.17 mmol), HATU (121 mg, 0.32 mmol), N-Ethyldiisopropyl amine (0.08 ml, 0.5 mmol) were dissolved in DMF (1 ml). This mixture was stirred at rt for 1 h. Reaction mass was diluted with water. Aqueous layer was extracted with DCM and MeOH (9:1) mixture. Organic layer was washed with water and aq. NaHCO$_3$ solution. Organic layer dried on anhydrous Na$_2$SO$_4$ and organic layer distilled on rotavapour to obtain crude. Crude was purified on Combi-flash using DCM and MeOH (96:4) as eluent to afford the titled compound (13 mg) as a brown solid. M.P.: 229-231° C. $^1$H-NMR ($\delta$ ppm, DMSO-$d_6$, 400 MHz): 12.69 (s, 1H), 10.92 (s, 1H), 8.48 (d, J, 1H), 7.98 (d, J 9.9, 1H), 7.75 (dt, J 1.8, 7.7, 1H), 7.40-7.25 (m, 5H), 7.19-7.11 (m, 2H), 4.31 (d, J 13.3, 2H), 3.99 (s, 2H), 3.80 (s, 2H), 3.41-3.35 (m, 1H), 3.05 (t, J 11.4, 2H), 2.10 (d, J 11, 2H), 1.80-1.69 (m, 2H).

Example 15

2-(Pyrazin-2-yl)-N-(5-(1-(6-(2-(3-(trifluoromethoxy) phenyl)acetamido)pyridazin-3-yl)piperidin-4-yl)-1,3,4-thiadiazol-2-yl)acetamide Intermediate 24 (80 mg, 0.17 mmol), 2-(pyrazin-2-yl) acetic acid (27 mg, 0.2 mmol), HATU (140 mg, 0.37 mmol), N-Ethyldiisopropyl amine (0.08 ml, 0.5 mmol) were dissolved in DMF (1 ml). This mixture was stirred at rt for 1 h. Reaction mass was diluted with water. Aqueous layer was extracted with DCM and MeOH (9:1) mixture. Organic layer was washed with water and aq. NaHCO$_3$ solution. Organic layer dried on anhydrous Na$_2$SO$_4$ and organic layer distilled on rotavapour to obtain crude. Crude was purified on Combi-flash using DCM and MeOH (94:6) as eluent to afford the titled compound (10 mg) as a pale-yellow solid. M.P.: 216-218° C. $^1$H-NMR ($\delta$ ppm, DMSO-$d_6$, 400 MHz): 12.76 (s, 1H), 10.94 (s, 1H), 8.66 (s, 1H), 8.58-8.53 (m, 2H), 7.99 (d, J 9.6, 1H), 7.48-7.42 (m, 1H), 7.39-7.32 (m, 3H), 7.24 (d, J 8.3, 1H), 4.30 (d, J 12.8, 2H), 4.08 (s, 2H), 3.78 (s, 2H), 3.40-3.35 (m, 1H), 3.05 (t, J 11.9, 2H), 2.10 (d, J 13.4, 2H), 1.80-1.65 (m, 2H).

Example 16

2-(Pyridin-2-yl)-N-(5-(1-(6-(2-(3-(trifluoromethoxy) phenyl)acetamido)pyridazin-3-yl)piperidin-4-yl)-1,3,4-thiadiazol-2-yl)acetamide dihydrochloride Example 8 (50 mg, 0.08 mmol) dissolved in THF (15 ml) and added Et$_2$O.HCl (5 ml). This mixture was stirred under nitrogen atmosphere for 30 mins. After 30 mins, removed THF and diethyl ether on rotavapour to obtain a residue. Residue was triturated with diethyl ether to obtain the titled compound (40 mg) as a brown solid. M.P.: 240-243° C. $^1$H-NMR (δ ppm, DMSO-d$_6$, 400 MHz): 12.95 (bs, 1H), 11.45 (s, 1H), 8.76 (d, J 5, 1H), 8.30 (t, J 6.6, 1H), 8.24 (d, J 10.1, 1H), 7.94 (d, J 10, 1H), 7.83 (d, J 7.7, 1H), 7.76 (t, J 6.4, 1H), 7.48-7.42 (m, 1H), 7.38-7.34 (m, 2H), 7.25 (d, J 8, 1H), 4.35-4.27 (m, 4H), 3.84 (s, 2H), 3.51-3.44 (m, 1H), 3.39-3.29 (m, 2H), 2.20-2.10 (m, 2H), 1.91-1.79 (m, 2H).

Example 17

2-(Pyridin-2-yl)-N-(6-(4-(5-(2-(3-(trifluoromethoxy)phenyl)acetamido)-1,3,4-thiadiazol-2-yl)piperidin-1-yl)pyridazin-3-yl)acetamide Intermediate 36 (150 mg, 0.38 mmol), 3-(Trifluoromethoxy)phenylacetic acid (100 mg, 0.45 mmol), HATU (316 mg, 0.37 mmol), N-Ethyldiisopropyl amine (0.2 ml, 1.134 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (8:92) as eluent to afford the titled compound (30 mg) as a pale-brown solid. M.P.: 220-222° C. $^1$H-NMR (δ ppm, DMSO-d$_6$, 400 MHz): 12.70 (s, 1H), 10.92 (s, 1H), 8.49 (s, 1H), 8.01 (d, J 8.7, 1H), 7.80-7.70 (m, 1H), 7.50-7.20 (m, 7H), 4.30 (d, J 12.2, 2H), 3.92 (s, 2H), 3.87 (s, 2H), 3.50-3.40 (m, 1H), 3.05 (t, J 12.2, 2H), 2.10 (d, J 11.1, 2H), 1.80-1.65 (m, 2H).

Example 18

2-(Pyridin-3-yl)-N-(6-(4-(5-(2-(3-(trifluoromethoxy)phenyl)acetamido)-1,3,4-thiadiazol-2-yl)piperidin-1-yl)pyridazin-3-yl)acetamide Intermediate 38 (75 mg, 0.19 mmol), 3-(Trifluoromethoxy)phenylacetic acid (50 mg, 0.22 mmol), HATU (158 mg, 0.42 mmol), N-Ethyldiisopropyl amine (0.1 ml, 0.5 mmol) were dissolved in DMF (1 ml). This mixture was stirred at rt for 1 h. Reaction mass was poured in to water to obtain a solid. Solid was filtered and purified by column chromatography on 60-120 mesh silica gel using MeOH and DCM (7:93) as eluent to afford the titled compound (15 mg) as a pale-brown solid. M.P.: 125-127° C. $^1$H-NMR (δ ppm, DMSO-d$_6$, 400 MHz): 12.70 (s, 1H), 10.97 (s, 1H), 8.51 (s, 1H), 8.45 (s, 1H), 7.99 (d, J 9.5, 1H), 7.73 (d, J 6.9, 1H), 7.50-7.42 (m, 1H), 7.40-7.30 (m, 4H), 7.26 (d, J 7.4, 1H), 4.30 (d, J 12.2, 2H), 3.87 (s, 2H), 3.76 (s, 2H), 3.40-3.35 (m, 1H), 3.04 (t, J 12, 2H), 2.09 (d, J 12, 2H), 1.80-1.68 (m, 2H).

Example 19

2-(Pyridin-3-yl)-N-(6-(4-(5-(2-(2,3,6-trifluorophenyl)acetamido)-1,3,4-thiadiazol-2-yl)piperidin-1-yl)pyridazin-3-yl)acetamide Intermediate 38 (75 mg, 0.19 mmol), 2,3,6-Trifluorophenylacetic acid (120 mg, 0.30 mmol), HATU (255 mg, 0.67 mmol), N-Ethyldiisopropyl amine (0.15 ml, 0.92 mmol) were dissolved in DMF (1 ml). This mixture was stirred at rt for 1 h. Reaction mass was poured in to water to obtain a solid. Solid was filtered and dried on high vacuum. This solid was triturated with Et$_2$O to obtain the titled compound (70 mg) as a brown solid. M.P.: 252-254° C. $^1$H-NMR (δ ppm, DMSO-d$_6$, 400 MHz): 12.84 (s, 1H), 10.96 (s, 1H), 8.51 (s, 1H), 8.44 (s, 1H), 7.98 (d, J 8.1, 1H), 7.76-7.70 (m, 1H), 7.51-7.29 (m, 3H), 7.20-7.10 (m, 1H), 4.30 (d, J 10.6, 2H), 3.96 (s, 2H), 3.76 (s, 2H), 3.41-3.35 (m, 1H), 3.10-3.00 (m, 2H), 2.10 (d, J 10, 2H), 1.81-1.69 (m, 2H).

Example 20

2-(Pyridin-2-yl)-N-(6-(4-(5-(2-(2,3,6-trifluorophenyl)acetamido)-1,3,4-thiadiazol-2-yl)piperidin-1-yl)pyridazin-3-yl)acetamide Intermediate 36 (100 mg, 0.25 mmol), 2,3,6-Trifluorophenylacetic acid (58 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (40 mg) as a brown solid. M.P.: 214-218° C. $^1$H-NMR (δ ppm, DMSO-d$_6$, 400 MHz): 12.84 (s, 1H), 10.92 (s, 1H), 8.49 (d, J 3.7, 1H), 8.01 (d, J 9.8, 1H), 7.74 (dt, J 1.6, 7.7, 1H), 7.50-7.43 (m, 1H), 7.40-7.35 (m, 2H), 7.28-7.23 (m, 1H), 7.20-7.13 (m, 1H), 4.31 (d, J 13.3, 2H), 3.97 (s, 2H), 3.91 (s, 2H), 3.40-3.30 (m, 1H), 3.05 (t, J 11.8, 2H), 2.10 (d, J 11.2, 2H), 1.80-1.70 (m, 2H).

Example 21

2-(2,3-Difluorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 2,3-Difluorophenylacetic acid (52 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (18 mg) as a brown solid. M.P.: 203-206° C. $^1$H-NMR (δ ppm, DMSO-d$_6$, 400 MHz): 12.76 (s, 1H), 10.92 (s, 1H), 8.49 (d, J 3.7, 1H), 8.01 (d, J 10.1, 1H), 7.75 (t, J 6.4, 1H), 7.40-7.33 (m, 3H), 7.27-7.23 (m, 1H), 7.20-7.15 (m, 2H), 4.30 (d, J 13.2, 2H), 3.95 (s, 2H), 3.91 (s, 2H), 3.40-3.35 (m, 1H), 3.05 (t, J 12.4, 2H), 2.10 (d, J 11.4, 2H), 1.80-1.70 (m, 2H).

Example 22

2-(3,4-Difluorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 3,4-Difluorophenylacetic acid (52 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (37 mg) as a pale-brown solid. M.P.: 211-214° C. $^1$H-NMR (δ ppm, DMSO-d$_6$, 400 MHz): 12.67 (s, 1H), 10.92 (s, 1H), 8.49 (d, J 4, 1H), 8.01 (d, J 9.8, 1H), 7.74 (dt, J 1.7, 7.7, 1H), 7.41-7.33 (m, 4H), 7.29-7.23 (m, 1H), 7.16-7.10 (m, 1H), 4.30 (d, J 13.1, 2H), 3.91 (s, 2H), 3.81 (s, 2H), 3.40-3.35 (m, 1H), 3.05 (t, J 11.4, 2H), 2.09 (d, J 11.2, 2H), 1.80-1.58 (m, 2H).

Example 23

2-(2-Fluorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 2-Fluorophenylacetic acid (47 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (40 mg) as a pale-brown solid. M.P.: 220-223° C. $^1$H-NMR (δ ppm, DMSO-$d_6$, 400 MHz): 12.71 (bs, 1H), 10.92 (s, 1H), 8.49 (d, J 4.1, 1H), 8.01 (d, J 9.5, 1H), 7.74 (t, J 7.8, 1H), 7.41-7.30 (m, 4H), 7.29-7.23 (m, 1H), 7.20-7.13 (m, 2H), 4.30 (d, J 13, 2H), 3.91 (s, 2H), 3.87 (s, 2H), 3.41-3.35 (m, 1H), 3.05 (t, J 11.6, 2H), 2.10 (d, J 11.1, 2H), 1.81-1.67 (m, 2H).

Example 24

2-(3-Fluorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 3-Fluorophenylacetic acid (47 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (7:93) as eluent to afford the titled compound (40 mg) as a brown solid. M.P.: 210-213° C. $^1$H-NMR (δ ppm, DMSO-$d_6$, 400 MHz): 12.69 (bs, 1H), 10.92 (s, 1H), 8.49 (d, J 4, 1H), 8.01 (d, J 9.8, 1H), 7.74 (dt, J 1.7, 7.4, 1H), 7.40-7.33 (m, 3H), 7.27-7.23 (m, 1H), 7.18-7.05 (m, 3H), 4.30 (d, J 13.1, 2H), 3.91 (s, 2H), 3.82 (s, 2H), 3.40-3.35 (m, 1H), 3.05 (t, J 11.8, 2H), 2.09 (d, J 11.4, 2H), 1.80-1.67 (m, 2H).

Example 25

2-(4-Fluorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 4-Fluorophenylacetic acid (47 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (25 mg) as a brown solid. M.P.: 194-197° C. $^1$H-NMR (δ ppm, DMSO-$d_6$, 400 MHz): 12.67 (s, 1H), 10.92 (s, 1H), 8.49 (d, J 4.6, 1H), 8.01 (d, J 9.8, 1H), 7.74 (dt, J 1.7, 7.7, 1H), 7.40-7.31 (m, 4H), 7.28-7.22 (m, 1H), 7.17-7.11 (m, 2H), 4.30 (d, J 13.1, 2H), 3.91 (s, 2H), 3.78 (s, 2H), 3.40-3.35 (m, 1H), 3.05 (t, J 11.8, 2H), 2.09 (d, J 11.6, 2H), 1.80-1.65 (m, 2H).

Example 26

2-(2-Methoxyphenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 2-Methoxyphenylacetic acid (50 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (37 mg) as a yellow solid. M.P.: 160-163° C. $^1$H-NMR (δ ppm, DMSO-$d_6$, 400 MHz): 12.55 (s, 1H), 10.92 (s, 1H), 8.49 (d, J 4.1, 1H), 8.01 (d, J 9.8, 1H), 7.75 (dt, J 1.8, 7.7, 1H), 7.40-7.36 (m, 2H), 7.29-7.23 (m, 2H), 7.21-7.18 (m, 1H), 6.96 (d, J 8.2, 1H), 6.91-6.86 (m, 1H), 4.31 (d, J 13.2, 2H), 3.91 (s, 2H), 3.76 (s, 2H), 3.71 (s, 3H), 3.40-3.33 (m, 1H), 3.05 (t, J 11.6, 2H), 2.10 (d, J 11.2, 2H), 1.80-1.69 (m, 2H).

Example 27

2-(2-Chlorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 2-Chlorophenylacetic acid (52 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (35 mg) as a brown solid. M.P.: 194-196° C. $^1$H-NMR (δ ppm, DMSO-$d_6$, 400 MHz): 12.73 (s, 1H), 10.91 (s, 1H), 8.49 (d, J 3.9, 1H), 8.01 (d, J 8.6, 1H), 7.77-7.71 (m, 1H), 7.47-7.35 (m, 4H), 7.34-7.28 (m, 2H), 7.27-7.22 (m, 1H), 4.30 (d, J 13.1, 2H), 3.98 (s, 2H), 3.91 (s, 2H), 3.41-3.36 (m, 1H), 3.05 (t, J 11.8, 2H), 2.10 (d, J 11.5, 2H), 1.80-1.66 (m, 2H).

Example 28

2-(5-Chloro-2-(trifluoromethyl)phenyl)-N-(5-(1-(6-(2-(pyridin-2-yl)acetamido) pyridazin-3-yl)piperidin-4-yl)-1,3,4-thiadiazol-2-yl)acetamide Intermediate 36 (100 mg, 0.25 mmol), 5-Chloro-2-trifluoromethylphenylacetic acid (72 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (17 mg) as a yellow solid. M.P.: 232-234° C. $^1$H-NMR (δ ppm, DMSO-$d_6$, 400 MHz): 12.74 (s, 1H), 10.91 (s, 1H), 8.49 (d, J 4.5, 1H), 8.01 (d, J 9.6, 1H), 7.77-7.72 (m, 2H), 7.67 (s, 1H), 7.60 (d, J 8.8, 1H), 7.41-7.34 (m, 2H), 7.27-7.23 (m, 1H), 4.30 (d, J 13, 2H), 4.09 (s, 2H), 3.91 (s, 2H), 3.41-3.30 (m, 1H), 3.05 (t, J 12, 2H), 2.10 (d, J 11.2, 2H), 1.80-1.67 (m, 2H).

Example 29

2-(4-Chlorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 4-Chlorophenylacetic acid (52 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (40 mg) as a pale-yellow solid. M.P.: 220-222° C. $^1$H-NMR (δ ppm, DMSO-$d_6$, 400 MHz): 12.68 (s, 1H), 10.91 (s, 1H), 8.49 (d, J 3.5, 1H), 8.01 (d, J 9.7, 1H), 7.75 (dt, J 1.5, 7.7, 1H), 7.41-7.32 (m, 6H), 7.28-7.23 (m, 1H), 4.30 (d, J 13.3, 2H), 3.91 (s, 2H), 3.79 (s, 2H), 3.41-3.35 (m, 1H), 3.05 (t, J 11.8, 2H), 2.09 (d, J 12.7, 2H), 1.80-1.65 (m, 2H).

Example 30

2-(Quinolin-6-yl)-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (100 mg, 0.25 mmol), Quinoline-6-acetic acid (47 mg, 0.25 mmol), HATU (173 mg, 0.46 mmol), N-Ethyldiisopropyl amine (0.11 ml, 0.62 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (35 mg) as an off-white solid. M.P.: 219-221° C. $^1$H-NMR (δ ppm, DMSO-$d_6$, 400 MHz): 12.77 (s, 1H), 10.92 (s, 1H), 8.87-8.85 (m, 1H), 8.33 (d, J 8.6, 1H), 8.01-7.95 (m, 2H), 7.88 (s, 1H), 7.70 (dd, J 1.7, 8.7, 1H), 7.54-7.49 (m, 1H), 7.48-7.42 (m, 1H), 7.37-7.32 (m, 3H), 7.23 (d, J 8, 1H), 4.29 (d, J 13, 2H), 4.02 (s, 2H), 3.78 (s, 2H), 3.40-3.32 (m, 1H), 3.04 (t, J 11.7, 2H), 2.09 (d, J 12.2, 2H), 1.80-1.67 (m, 2H).

Example 31

2-o-Tolyl-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (100 mg, 0.25 mmol), O-Tolylacetic acid (37 mg, 0.25 mmol), HATU (173 mg, 0.46 mmol), N-Ethyldiisopropyl amine (0.11 ml, 0.62 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (5:95) as eluent to afford the titled compound (40 mg) as an off-white solid. M.P.: 198-200° C. $^1$H-NMR (δ ppm, DMSO-$d_6$, 400 MHz): 12.69 (bs, 1H), 10.94 (s, 1H), 7.98 (d, J 9.8, 1H), 7.48-7.42 (m, 1H), 7.38-7.32 (m, 3H), 7.26-7.19 (m, 2H), 7.17-7.09 (m, 3H), 4.29 (d, J 13.1, 2H), 3.79 (s, 2H), 3.77 (s, 2H), 3.40-3.32 (m, 1H), 3.04 (t, J 11.7, 2H), 2.24 (s, 3H), 2.08 (d, J 10.9, 2H), 1.80-1.67 (m, 2H).

Example 32

N-(6-(4-(5-(2-(1H-indol-3-yl)acetamido)-1,3,4-thiadiazol-2-yl)piperidin-1-yl)pyridazin-3-yl)-2-(3-(trifluoromethoxy)phenyl)acetamide Intermediate 24 (100 mg, 0.25 mmol), Indole-3-acetic acid (43 mg, 0.25 mmol), HATU (173 mg, 0.46 mmol), N-Ethyldiisopropyl amine (0.11 ml, 0.62 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (5:95) as eluent to afford the titled compound (35 mg) as a brown solid. M.P.: 220-223° C. $^1$H-NMR (δ ppm, DMSO-$d_6$, 400 MHz): 12.60 (s, 1H), 10.92 (s, 1H), 7.98 (d, J 9.9, 1H), 7.55 (d, J 7.8, 1H), 7.48-7.42 (m, 1H), 7.38-7.32 (m, 4H), 7.28-7.21 (m, 2H), 7.08-7.03 (m, 1H), 6.98-6.94 (m, 1H), 4.29 (d, J 13, 2H), 3.87 (s, 2H), 3.78 (s, 2H), 3.40-3.30 (m, 1H), 3.04 (t, J 11.8, 2H), 1.80-1.66 (m, 2H).

Example 33

2-(2-Fluorophenyl)-N-(6-(4-(5-(2-(pyrazin-2-yl)acetamido)-1,3,4-thiadiazol-2-yl)piperidin-1-yl)pyridazin-3-yl)acetamide Intermediate 34 (300 mg, 0.75 mmol), 2-(pyrazin-2-yl)acetic acid (120 mg, 0.87 mmol), HATU (600 mg, 1.59 mmol), N-Ethyldiisopropyl amine (0.3 ml, 2.17 mmol) were dissolved in DMF (4 ml). This mixture was stirred at rt for 1 h. Reaction mass was poured in to water to obtain a solid. Solid was filtered and purified the solid by column chromatography on 60-120 silica gel using MeOH and DCM (5:95) as eluent to afford the titled compound (13 mg) as a Pale-brown solid. M.P.: 232-234° C. $^1$H-NMR (δ ppm, DMSO-$d_6$, 400 MHz): 12.74 (s, 1H), 10.90 (s, 1H), 8.65 (s, 1H), 8.57-8.52 (m, 2H), 7.98 (d, J 9.8, 1H), 7.40-7.36 (m, 2H), 7.35-7.25 (m, 1H), 7.18-7.12 (m, 2H), 4.30 (d, J 13.3, 2H), 4.06 (s, 2H), 3.79 (s, 2H), 3.40-3.31 (m, 1H), 3.05 (t, J 12, 2H), 2.10 (d, J 10.7, 2H), 1.80-1.66 (m, 2H).

Example 34

2-(3-(Azetidin-1-yl)phenyl)-N-(5-(1-(6-(2-(3-(trifluoromethoxy)phenyl)acetamido) pyridazin-3-yl)piperidin-4-yl)-1,3,4-thiadiazol-2-yl)acetamide Intermediate 24 (100 mg, 0.25 mmol), 2-(3-(azetidin-1-yl)phenyl)acetic acid (45 mg, 0.25 mmol), HATU (170 mg, 0.44 mmol), N-Ethyldiisopropyl amine (0.11 ml, 0.62 mmol) were dissolved in DMF (2 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (40 mg) as an Off-White solid. M.P.: 140-142° C. $^1$H-NMR (δ ppm, DMSO-$d_6$, 400 MHz): 12.60 (s, 1H), 10.93 (s, 1H), 7.99 (d, J 9.8, 1H), 7.48-7.42 (m, 1H), 7.40-7.32 (m, 3H), 7.24 (d, J 7.6, 1H), 7.07 (t, J 7.8, 1H), 6.59 (d, J 7.3, 1H), 6.36 (s, 1H), 6.28 (d, J 7.8, 1H), 4.29 (d, J 12.9, 2H), 3.81-3.73 (m, 6H), 3.66 (s, 2H), 3.40-3.31 (m, 1H), 3.04 (t, J 11.8, 2H), 2.81-2.72 (m, 2H), 2.08 (d, J 11, 2H), 1.80-1.66 (m, 2H).

Example 35

2-(3-Chlorophenyl)-N-(5-(1-(6-(2-(pyridin-2-yl)acetamido)pyridazin-3-yl)piperidin-4-yl)-1,3,4-thiadiazol-2-yl)acetamide Intermediate 36 (100 mg, 0.25 mmol), 3-Chlorophenylacetic acid (52 mg, 0.30 mmol), HATU (211 mg, 0.55 mmol), N-Ethyldiisopropyl amine (0.13 ml, 0.76 mmol) were dissolved in DMF (1 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (35 mg) as a pale-yellow solid. M.P.: 198-201° C. $^1$H-NMR (δ ppm, DMSO-$d_6$, 400 MHz): 12.68 (s, 1H), 10.91 (s, 1H), 8.49 (d, J 4.2, 1H), 8.01 (d, J 9.8, 1H), 7.76-7.72 (m, 1H), 7.40-7.30 (m, 5H), 7.28-7.22 (m, 2H), 4.30 (d, J 13.2, 2H), 3.91 (s, 2H), 3.82 (s, 2H), 3.40-3.29 (m, 1H), 3.05 (t, J 11.8, 2H), 2.10 (d, J 11.7, 2H), 1.80-1.77 (m, 2H).

Example 36

3-Hydroxy-2-phenyl-N-(5-(1-(6-(2-(3-(trifluoromethoxy)phenyl)acetamido)pyridazin-3-yl)piperidin-4-yl)-1,3,4-thiadiazol-2-yl)propanamide Intermediate 24 (100 mg, 0.21 mmol), Tropic acid (42 mg, 0.25 mmol), HATU (173 mg, 0.46 mmol), N-Ethyldiisopropyl amine (0.11 ml, 0.62 mmol) were dissolved in DMF (2 ml). This mixture was stirred at rt for 1 h. Reaction mass was poured in to water to obtain a solid. Solid was filtered and purified the solid by column chromatography on 60-120 silica gel using MeOH and DCM (5:95) as eluent to afford the titled compound (12 mg) as an Off-White solid. M.P.: 212-214° C. $^1$H-NMR (δ ppm, DMSO-$d_6$, 400 MHz): 12.66 (s, 1H), 10.94 (s, 1H), 7.99 (d, J 9.9, 1H), 7.48-7.42 (m, 4H), 7.39-7.22 (m, 9H), 5.06-5.02 (m, 1H), 4.30 (d, J 13.8, 2H), 4.10-4.00 (m, 2H), 3.78 (s, 2H), 3.62-3.57 (m, 1H), 3.40-3.30 (m, 2H), 3.05 (t, J 12.4, 2H), 2.09 (d, J 10.8, 2H), 1.80-1.68 (m, 2H).

Example 37

(R)-2-hydroxy-2-phenyl-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (100 mg, 0.21 mmol), (R)-(−)-Mandelic acid (35 mg, 0.25 mmol), HATU (173 mg, 0.46 mmol), N-Ethyldiisopropyl amine (0.11 ml, 0.62 mmol) were dissolved in DMF (2 ml). This mixture was stirred at rt for 1 h. Reaction mass was poured in to water to obtain a solid. Solid was filtered and purified the solid by column chromatography on 60-120 silica gel using MeOH and DCM (5:95) as eluent to afford the titled compound (15 mg) as a pale-brown solid. $^1$H-NMR (δ ppm, DMSO-$d_6$, 400 MHz): 12.41 (s, 1H), 10.93 (s, 1H), 7.98 (d, J 9.7, 1H), 7.50-7.30 (m, 10H), 6.32 (bs, 1H), 5.30 (s, 1H), 4.29 (d, J 13, 2H), 3.78 (s, 2H), 3.50-3.40 (m, 1H), 3.04 (t, J 11.7, 2H), 2.09 (d, J 11, 2H), 1.80-1.65 (m, 2H).

Example 38

2-(3-(3-Fluoroazetidin-1-yl)phenyl)-N-(5-(1-(6-(2-(3-(trifluoromethoxy)phenyl)acetamido)pyridazin-3-yl)piperidin-4-yl)-1,3,4-thiadiazol-2-yl)acetamide Intermediate 24 (100 mg, 0.21 mmol), 2-(3-(3-Fluoroazetidin-1-yl)phenyl)acetic acid (53 mg, 0.25 mmol), HATU (173 mg, 0.46 mmol), N-Ethyldiisopropyl amine (0.11 ml, 0.62 mmol) were dissolved in DMF (2 ml). This mixture was stirred at rt for 1 h. Reaction mass was poured in to water to obtain a solid. Solid was filtered and purified the solid by column chromatography on 60-120 silica gel using MeOH and DCM (4:96) as eluent to afford the titled compound (40 mg) as an Off-White solid. $^1$H-NMR (δ ppm, DMSO-$d_6$, 400 MHz): 12.62 (s, 1H), 10.93 (s, 1H), 7.99 (d, J 9.7, 1H), 7.48-7.42 (m, 1H), 7.39-7.22 (m, 4H), 7.11 (t, J 5.8, 1H), 6.65 (d, J 7.5, 1H), 6.43 (s, 1H), 6.36 (d, J 8, 1H), 4.29 (d, J 13.2, 2H), 4.18-4.06 (m, 2H), 3.90-3.76 (m, 5H), 3.68 (s, 2H), 3.40-3.30 (m, 1H), 3.04 (t, J 11.8, 2H), 2.07 (d, J 12.2, 2H), 1.80-1.66 (m, 2H).

Example 39

2-(Pyridin-2-yl)-N-(5-((1-(6-(2-(3-(trifluoromethoxy)phenyl)acetamido)pyridazin-3-yl)piperidin-4-yl)methyl)-1,3,4-thiadiazol-2-yl)acetamide Intermediate 41 (34 mg, 0.07 mmol), 2-Pyridylacetic acid hydrochloride (15 mg, 0.086 mmol), HATU (58 mg, 0.15 mmol), N-Ethyldiisopropyl amine (0.04 ml, 0.15 mmol) were dissolved in DMF (2 ml). This mixture was stirred at rt for 1 h. Reaction mass was poured in to water to obtain a solid. Solid was filtered and purified the solid by combi-flash using MeOH and DCM (4:96) as eluent to afford the titled compound (2 mg) as an off-white solid. $^1$H-NMR (δ ppm, DMSO-$d_6$, 400 MHz): 12.67 (s, 1H), 10.90 (s, 1H), 8.48 (d, J 4, 1H), 7.95 (d, J 9.8, 1H), 7.76 (dt, J 2, 7.7, 1H), 7.48-7.22 (m, 7H), 4.23 (d, J 12.9, 2H), 3.99 (s, 2H), 3.77 (s, 2H), 2.93 (d, J 7, 2H), 2.82 (t, J 12, 2H), 2.00-1.90 (m, 1H), 1.72 (d, J 12, 2H), 1.30-1.18 (m, 2H).

Biological Assays

The pharmacological properties of the compounds described herein may be confirmed by a number of pharmacological assays as described below.

Assay 1: Determination of Glutaminase Enzyme Activity

Compounds can be assessed for their ability to inhibit the enzymatic activity of recombinant Glutaminase 1 (GAC) using a biochemical assay in a 2-step procedure: 1. conversion of L-glutamine to glutamate by GAC, and 2. glutamate to alpha-ketoglutarate catalyzed by glutamate dehydrogenase (GDH). Reduction of NAD$^+$ to NADH manifested by a change in absorbance is determined spectrophotometrically. A substrate solution is prepared (50 mM Tris-HCl pH 8.0, 0.2 mM EDTA, 150 mM K$_2$HPO$_4$, 0.1 mg/ml BSA, 1 mM DTT, 20 mM L-glutamine, 2 mM NAD$^+$, and 10 ppm antifoam) and 50 µl of the substrate solution is to be added to a 96-well half area clear plate. The compound is added as a DMSO solution. Enzymatic reaction is started by the addition of 50 µl of enzyme solution (50 mM Tris-HCl pH 8.0, 0.2 mM EDTA, 150 mM K$_2$HPO$_4$, 0.1 mg/ml BSA, 1 mM DTT, 10 ppm antifoam, 4 units/ml GDH, 4 mM adenosine diphosphate, and 4 nM GAC) and read in a Molecular Devices M5 plate reader at 20° C. The plate reader is configured to read absorbance (λ=340 nm) in kinetic mode for 15 minutes. Data is recorded as milli-absorbance units per minute and slopes are compared to a control compound and a DMSO-only control on the same plate. Compounds with slopes less than the DMSO control can be considered as inhibitors and plate variability is assessed using the control compound. Activity of the test compound is reported as % inhibition. The data is analyzed using Graphpad Prism (Graphpad software; San Diego Calif.) for IC$_{50}$ determination.

Assay 2: Determination of Enzyme Activity Through Estimation of Ammonia

L-glutaminase enzyme assay can be performed using a colorimetric method by quantifying ammonia formation in a spectrophotometric analysis using Nessler's Reagent. The procedure is adopted from British Microbiology Research Journal, 4(1), 97-115, 2014, with modification.

For routine assay 0.1 ml of properly diluted enzyme (incubated with or without the test compound) is added to 0.4 ml of 0.025 M L-glutamine solution in 0.1 M boric acid borate buffer (pH 8.0). After incubation for 30 minutes at 37° C., the reaction is stopped by the addition of 0.5 ml of 1N $H_2SO_4$. The precipitated protein is removed by centrifugation and 0.2 ml of supernatant is added to 3.8 ml of distilled water. Thereafter, 0.5 ml of Nessler's reagent is added, and the absorbance measured at 400 nm within 1 to 3 minutes. Enzyme and substrate blanks are included in all assays, and a standard curve is prepared with ammonium chloride. The enzyme activity is expressed as unit (U)/ml. One unit of L-glutaminase is defined as the amount of enzyme that liberates one micromole (µmol) of ammonia per minute under standard conditions. The specific activity (sp. activity) is defined as the units of L-glutaminase per milligram protein. Accordingly, the change in specific activity of glutaminase in the presence and absence of test compound is reported.

Assay 3: Determination of Glutaminase Enzyme Activity Using Glutaminase Enzyme from Mice Brain/Kidney Step 1: Preparation of Tissue Homogenates:

Male Balb/c mice were administered 0.28 M ammonium chloride in drinking water for 7 days. The animals were sacrificed and brain/kidney organs collected on dry ice. These organs were suspended in a homogenization buffer containing 20 mM phosphate buffer-pH 7.4, 0.5 mM EDTA, 5 mM 2-mercaptoethanol, 25% glycerol and 0.02% BSA. The tissue was homogenized and supernatants were stored at −80° C. until the enzyme assay was performed.

Step-2: Enzyme Assay

Aim: Compounds were assessed for their ability to inhibit the enzymatic activity of L-glutaminase present in mice brain/kidney homogenate.

Protocol: The assay was performed using a colorimetric method using Nessler's Reagent by quantifying the amount of ammonia formed as a by product during the enzymatic conversion of L-glutamine to glutamate. In the routine assay, 16 µl of tissue homogenate is added to 33 µl of Tris-Hcl phosphate buffer (pH 8) along with 1 µl of DMSO/test compound containing the desired final concentration and vortexed briefly. 50 µl of 20 mM L-glutamine Tris buffer is added to start the reaction and incubated for 15 minutes at 37° C. The ammonia formed is detected by adding 20 µl of reaction mixture to cold water in a 96 well plate followed by 20 µl of Nessler's reagent. The colour developed is measured at 450 nm. Data Analysis: Activity of the test compound is reported as % inhibition and the data is analyzed using Graphpad Prism (Graphpad software; San Diego Calif.) for $IC_{50}$ determination.

Results for Assay 3:

| | Glutaminase (Brain) activity | | |
|---|---|---|---|
| | % inhibition | | |
| Ex. No. | @1 µM | 0.1 µM | IC50 |
| Example 1 | B | D | E |
| Example 2 | C | D | — |
| Example 2A | D | D | — |
| Example 2B | D | D | — |
| Example 3 | B | C | — |
| Example 3A | D | D | — |
| Example 3B | D | D | — |
| Example-4 | B | C | D |
| Example-5 | C | D | — |
| Example-6 | D | D | — |
| Example-7 | D | D | — |
| Example-8 | A | A | A |
| Example-9 | A | B | B |
| Example-10 | A | B | B |
| Example-11 | B | D | — |
| Example-12 | A | B | B |
| Example-13 | B | D | — |
| Example-14 | A | A | A |
| Example-15 | A | B | A |
| Example-16 | A | A | A |
| Example-17 | A | A | A |
| Example-18 | A | A | A |
| Example-19 | A | B | — |
| Example-20 | B | C | B |
| Example-21 | A | B | B |
| Example-22 | A | B | B |
| Example-23 | A | B | B |
| Example-24 | A | B | B |
| Example-25 | A | B | B |
| Example-26 | A | B | B |
| Example-27 | A | B | — |
| Example-28 | B | B | B |
| Example-29 | A | B | B |
| Example-30 | A | B | B |
| Example-31 | B | C | — |
| Example-32 | B | C | — |
| Example-33 | B | C | — |
| Example-34 | B | C | — |
| Example-35 | A | B | A |
| Example-36 | B | C | — |

For percent (%) inhibition: A is >75% to 100%; B is >50% to ≤75%; C is >25% to ≤50%; and D is ≤25%. For IC50: A is <50 nM; B is ≥50 nM to <200 nM; C is ≥200 nM to <500 nM; D is ≥500 nM to <1000 nM; and E is ≥1000 nM to ≤2000 nM.

Assay 4: In Vitro Cell Proliferation Assay in Cancer Cell Lines

Growth inhibition assays were carried out using 10% FBS supplemented media. Cells were seeded at a concentration of 5000-20,000 cells/well in a 96-well plate. Test compounds at a concentration range from 0.01 to 10000 nM were added after 24 hours. Growth was assessed using the 3-[4,5-dimethylthiazol-2-yl]-2,5-diphenyltetrazolium bromide (MIT) dye reduction test at 0 h (prior to the addition of the test compound) and 72 hours after the addition of test compound. Absorbance was read on a Fluostar Optima (BMG Labtech, Germany) at a wave length of 450 nm. Data were analysed using GraphPad Prism and percent inhibition due to the test compound compared to the control was calculated accordingly. The results are as shown below.

| | GI50 | | | | |
|---|---|---|---|---|---|
| Ex. No. | MDA-MB-231 | A549 | HCT116 | Daudi | Rajii |
| Example 3 | E | — | — | — | — |
| Example-4 | C | — | — | — | — |
| Example-8 | — | B | C | A | A |
| Example-9 | B | — | — | — | — |
| Example-10 | B | — | — | — | — |
| Example-11 | C | — | — | — | — |

-continued

| Ex. No. | GI50 | | | | |
|---|---|---|---|---|---|
| | MDA-MB-231 | A549 | HCT116 | Daudi | Rajii |
| Example-12 | A | — | — | — | — |
| Example-14 | A | — | — | — | — |
| Example-15 | A | — | — | — | — |
| Example-17 | A | — | — | — | — |
| Example-18 | A | — | — | — | — |

GI50: A is <100 nM; B is ≥100 nM to <250 nM; C is ≥250 nM to <500 nM; D is ≥500 nM to <1000 nM and E is ≥1000 nM to ≤3000 nM.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

We claim:
1. A compound selected from:
2-(Pyridin-2-yl)-N-(5-(1-(6-(2-(3-(trifluoromethoxy)phenyl)acetamido)pyridin-3-yl) piperidin-4-yl)-1,3,4-thiadiazol-2-yl)acetamide;
(RS)-2-(Pyridin-2-yl)-N-(5-(1-(6-(2-(3-(trifluoromethoxy)phenyl)acetamido)pyridin-3-yl) piperidin-3-yl)-1,3,4-thiadiazol-2-yl)acetamide;
(R)-2-(Pyridin-2-yl)-N-(5-(1-(6-(2-(3-(trifluoromethoxy)phenyl)acetamido) pyridin-3-yl) piperidin-3-yl)-1,3,4-thiadiazol-2-yl)acetamide;
(S)-2-(Pyridin-2-yl)-N-(5-(1-(6-(2-(3-(trifluoromethoxy)phenyl)acetamido) pyridin-3-yl) piperidin-3-yl)-1,3,4-thiadiazol-2-yl)acetamide;
(RS)-2-(Pyridin-3-yl)-N-(5-(1-(6-(2-(3-(trifluoromethoxy)phenyl)acetamido)pyridin-3-yl) piperidin-3-yl)-1,3,4-thiadiazol-2-yl)acetamide;
(R)-2-(Pyridin-3-yl)-N-(5-(1-(6-(2-(3-(trifluoromethoxy)phenyl)acetamido) pyridin-3-yl) piperidin-3-yl)-1,3,4-thiadiazol-2-yl)acetamide;
(S)-2-(Pyridin-3-yl)-N-(5-(1-(6-(2-(3-(trifluoromethoxy)phenyl)acetamido) pyridin-3-yl) piperidin-3-yl)-1,3,4-thiadiazol-2-yl)acetamide;
2-(Pyridin-3-yl)-N-(5-(1-(6-(2-(3-(trifluoromethoxy)phenyl)acetamido)pyridin-3-yl) piperidin-4-yl)-1,3,4-thiadiazol-2-yl)acetamide;
2-(3-Cyanophenyl)-N-(5-(1-(6-(2-(3-(trifluoromethoxy)phenyl)acetamido)pyridin-3-yl)piperidin-4-yl)-1,3,4-thiadiazol-2-yl)acetamide;
2-(Pyridin-2-yl)-N-(5-(4-(5-(2-(3-(trifluoromethoxy)phenyl)acetamido)-1,3,4-thiadiazol-2-yl)piperidin-1-yl) pyridin-2-yl)acetamide;
2-(Pyridin-2-yl)-N-(5-(3-(5-(2-(3-(trifluoromethoxy)phenyl)acetamido)-1,3,4-thiadiazol-2-yl)piperidin-1-yl) pyridin-2-yl)acetamide;
2-(pyridin-2-yl)-N-(5-(1-(6-(2-(3-(trifluoromethoxy)phenyl)acetamido)pyridazin-3-yl) piperidin-4-yl)-1,3,4-thiadiazol-2-yl)acetamide;
2-(Pyridin-2-yl)-N-(5-(1-(6-(2-(3-(trifluoromethoxy)phenyl)acetamido)pyridazin-3-yl)piperidin-3-yl)-1,3,4-thiadiazol-2-yl)acetamide;
2-(Pyridin-3-yl)-N-(5-(1-(6-(2-(3-(trifluoromethoxy)phenyl)acetamido)pyridazin-3-yl)piperidin-4-yl)-1,3,4-thiadiazol-2-yl)acetamide;
2-(3-(Methylsulfonamido)phenyl)-N-(5-(1-(6-(2-(3-(trifluoromethoxy)phenyl) acetamido)pyridazin-3-yl)piperidin-4-yl)-1,3,4-thiadiazol-2-yl)acetamide;
2-(2-Chlorophenyl)-N-(6-(4-(5-(2-(pyridin-2-yl)acetamido)-1,3,4-thiadiazol-2-yl) piperidin-1-yl)pyridazin-3-yl)acetamide;
2-(2-Chlorophenyl)-N-(5-(1-(6-(2-(3-(trifluoromethoxy)phenyl)acetamido)pyridazin-3-yl)piperidin-3-yl)-1,3,4-thiadiazol-2-yl)acetamide;
2-(2-Fluorophenyl)-N-(6-(4-(5-(2-(pyridin-2-yl)acetamido)-1,3,4-thiadiazol-2-yl) piperidin-1-yl)pyridazin-3-yl)acetamide;
2-(Pyrazin-2-yl)-N-(5-(1-(6-(2-(3-(trifluoromethoxy)phenyl)acetamido)pyridazin-3-yl)piperidin-4-yl)-1,3,4-thiadiazol-2-yl)acetamide;
2-(Pyridin-2-yl)-N-(5-(1-(6-(2-(3-(trifluoromethoxy)phenyl)acetamido)pyridazin-3-yl)piperidin-4-yl)-1,3,4-thiadiazol-2-yl)acetamide dihydrochloride;
2-(Pyridin-2-yl)-N-(6-(4-(5-(2-(3-(trifluoromethoxy)phenyl)acetamido)-1,3,4-thiadiazol-2-yl)piperidin-1-yl) pyridazin-3-yl)acetamide;
2-(Pyridin-3-yl)-N-(6-(4-(5-(2-(3-(trifluoromethoxy)phenyl)acetamido)-1,3,4-thiadiazol-2-yl)piperidin-1-yl) pyridazin-3-yl)acetamide;
2-(Pyridin-3-yl)-N-(6-(4-(5-(2-(2,3,6-trifluorophenyl)acetamido)-1,3,4-thiadiazol-2-yl)piperidin-1-yl) pyridazin-3-yl)acetamide;
2-(Pyridin-2-yl)-N-(6-(4-(5-(2-(2,3,6-trifluorophenyl)acetamido)-1,3,4-thiadiazol-2-yl)piperidin-1-yl) pyridazin-3-yl)acetamide;
2-(2,3-Difluorophenyl)-N-(5-(1-(6-(2-(pyridin-2-yl)acetamido)pyridazin-3-yl)piperidin-4-yl)-1,3,4-thiadiazol-2-yl)acetamide;
2-(3,4-Difluorophenyl)-N-(5-(1-(6-(2-(pyridin-2-yl)acetamido)pyridazin-3-yl)piperidin-4-yl)-1,3,4-thiadiazol-2-yl)acetamide;
2-(2-Fluorophenyl)-N-(5-(1-(6-(2-(pyridin-2-yl)acetamido)pyridazin-3-yl)piperidin-4-yl)-1,3,4-thiadiazol-2-yl)acetamide;
2-(3-Fluorophenyl)-N-(5-(1-(6-(2-(pyridin-2-yl)acetamido)pyridazin-3-yl)piperidin-4-yl)-1,3,4-thiadiazol-2-yl)acetamide;
2-(4-Fluorophenyl)-N-(5-(1-(6-(2-(pyridin-2-yl)acetamido)pyridazin-3-yl)piperidin-4-yl)-1,3,4-thiadiazol-2-yl)acetamide;
2-(3-Chlorophenyl)-N-(5-(1-(6-(2-(pyridin-2-yl)acetamido)pyridazin-3-yl)piperidin-4-yl)-1,3,4-thiadiazol-2-yl)acetamide;
3-Hydroxy-2-phenyl-N-(5-(1-(6-(2-(3-(trifluoromethoxy)phenyl)acetamido) pyridazin-3-yl)piperidin-4-yl)-1,3,4-thiadiazol-2-yl)propanamide;
(R)-2-hydroxy-2-phenyl-N-(5-(1-(6-(2-(3-(trifluoromethoxy)phenyl)acetamido) pyridazin-3-yl)piperidin-4-yl)-1,3,4-thiadiazol-2-yl)acetamide;
2-(3-(3-Fluoroazetidin-1-yl)phenyl)-N-(5-(1-(6-(2-(3-(trifluoromethoxy)phenyl) acetamido)pyridazin-3-yl) piperidin-4-yl)-1,3,4-thiadiazol-2-yl)acetamide;
2-(Pyridin-2-yl)-N-(5-((1-(6-(2-(3-(trifluoromethoxy)phenyl)acetamido)pyridazin-3-yl) piperidin-4-yl)methyl)-1,3,4-thiadiazol-2-yl)acetamide;
and pharmaceutically acceptable salts thereof.

2. A pharmaceutical composition comprising a compound of claim 1 and a pharmaceutically acceptable carrier.

3. The pharmaceutical composition of claim 2, further comprising one or more additional therapeutic agents selected from anti-cancer agents, anti-inflammatory agents, immunosuppressive agents, steroids, non-steroidal anti-inflammatory agents, antihistamines, analgesics, and mixtures thereof.

4. A method for the treatment of carcinoma of the kidney, carcinoma of the liver, or carcinoma of the lung, comprising the step of administering to a subject in need thereof an effective amount of compound of claim 1.

5. The method of claim 4, further comprising the step of administering simultaneously or sequentially to a subject in need thereof at least one other anti-cancer agent, anti-inflammatory agent, immunosuppressive agent, steroid, non-steroidal anti-inflammatory agent, antihistamine, analgesic, or a mixture thereof.

6. A compound selected from 2-(pyridin-2-yl)-N-(5-((1-(6-(2-(3-(trifluoromethoxy)phenyl)acetamido)pyridazin-3-yl)piperidin-4-yl)methyl)-1,3,4-thiadiazol-2-yl)acetamide and pharmaceutically acceptable salts thereof.

7. The method of claim 4, wherein the subject suffers from carcinoma of the kidney.

8. The method of claim 4, wherein the subject suffers from carcinoma of the liver.

9. The method of claim 4, wherein the subject suffers from carcinoma of the lung.

10. A method for the treatment of carcinoma of the kidney, carcinoma of the liver, or carcinoma of the lung, comprising the step of administering to a subject in need thereof an effective amount of compound of claim 6.

11. The method of claim 10, wherein the subject suffers from carcinoma of the kidney.

12. The method of claim 10, wherein the subject suffers from carcinoma of the liver.

13. The method of claim 10, wherein the subject suffers from carcinoma of the lung.

\* \* \* \* \*